(12) United States Patent
Mann

(10) Patent No.: US 12,245,967 B2
(45) Date of Patent: Mar. 11, 2025

(54) FLUID COLLECTION ASSEMBLIES INCLUDING AN ADJUSTABLE SPINE

(71) Applicant: PureWick Corporation, El Cajon, CA (US)

(72) Inventor: Gregory Mann, Covington, GA (US)

(73) Assignee: PureWick Corporation, Covington, GA (US)

( * ) Notice: Subject to any disclaimer, the term of this patent is extended or adjusted under 35 U.S.C. 154(b) by 633 days.

(21) Appl. No.: 17/527,769

(22) Filed: Nov. 16, 2021

(65) Prior Publication Data

US 2022/0151817 A1    May 19, 2022

Related U.S. Application Data

(60) Provisional application No. 63/115,410, filed on Nov. 18, 2020.

(51) Int. Cl.
   *A61F 5/48*    (2006.01)
   *A61F 5/455*   (2006.01)

(52) U.S. Cl.
   CPC .............. *A61F 5/485* (2013.01); *A61F 5/455* (2013.01)

(58) Field of Classification Search
   CPC .. A61F 5/451; A61F 5/455; A61F 5/44; A61F 5/4405; A61F 5/453; A61F 5/4408
   See application file for complete search history.

(56) References Cited

U.S. PATENT DOCUMENTS

| 737,443 A | 8/1903 | Mooers |
|---|---|---|
| 1,032,841 A | 7/1912 | Koenig |
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |

(Continued)

FOREIGN PATENT DOCUMENTS

| AU | 2018216821 A1 | 8/2019 |
|---|---|---|
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Andrew J Mensh
*Assistant Examiner* — Meagan Ngo
(74) *Attorney, Agent, or Firm* — Dorsey & Whitney LLP

(57) ABSTRACT

An example fluid collection assembly includes a fluid impermeable barrier defining at least a chamber, at least one opening, and a fluid outlet. The fluid collection assembly also includes at least one porous material disposed in the chamber and an adjustable spine. The adjustable spine is configured to selectively change the shape of at least a portion of the fluid collection assembly. For example, the adjustable spine includes a first strip and a second strip. The second strip is configured to switch from at least a relaxed configuration to a stressed configuration. The fluid collection assembly may exhibit a first shape when the second strip is in the relaxed configuration and a second shape that is different than the first shape when the second strip is in the stressed configuration.

26 Claims, 16 Drawing Sheets

(56) References Cited

U.S. PATENT DOCUMENTS

| | | |
|---|---|---|
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |

(56) References Cited

U.S. PATENT DOCUMENTS

| | | |
|---|---|---|
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |

(56) References Cited

U.S. PATENT DOCUMENTS

| | | |
|---|---|---|
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |

(56) References Cited

U.S. PATENT DOCUMENTS

| | | |
|---|---|---|
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,226,376 B2 | 1/2022 | Yamauchi et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 12,023,457 B2 | 7/2024 | Mann et al. |
| 12,042,422 B2 | 7/2024 | Davis et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |

(56) References Cited

U.S. PATENT DOCUMENTS

| | | |
|---|---|---|
| 2007/0137718 A1 | 6/2007 | Rushlander et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0160882 A1 | 6/2010 | Lowe |
| 2010/0174250 A1 | 7/2010 | Hu et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0138064 A1 | 5/2013 | Stroebech et al. |
| 2013/0150813 A1 | 6/2013 | Gordon et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |

(56) References Cited

U.S. PATENT DOCUMENTS

| | | |
|---|---|---|
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez .................. A61F 5/443 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ...................... A61F 5/455 |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1* | 3/2021 | Blabas .................. A61F 5/455 |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |

(56) References Cited

U.S. PATENT DOCUMENTS

| | | | |
|---|---|---|---|
| 2022/0257407 A1 | 8/2022 | Johannes et al. | |
| 2022/0265460 A1 | 8/2022 | Coker | |
| 2022/0265462 A1 | 8/2022 | Alder et al. | |
| 2022/0270711 A1 | 8/2022 | Feala et al. | |
| 2022/0273482 A1 | 9/2022 | Johannes et al. | |
| 2022/0280357 A1 | 9/2022 | Jagannathan et al. | |
| 2022/0287689 A1 | 9/2022 | Johannes | |
| 2022/0296408 A1 | 9/2022 | Evans et al. | |
| 2022/0305191 A1 | 9/2022 | Joseph et al. | |
| 2022/0313222 A1* | 10/2022 | Austermann ........ A61B 10/007 |
| 2022/0313474 A1 | 10/2022 | Kriscovich et al. | |
| 2022/0331170 A1 | 10/2022 | Erdem et al. | |
| 2022/0339024 A1 | 10/2022 | Johannes et al. | |
| 2022/0354685 A1 | 11/2022 | Davis et al. | |
| 2022/0362049 A1 | 11/2022 | Austermann et al. | |
| 2022/0370231 A1 | 11/2022 | Wang et al. | |
| 2022/0370234 A1 | 11/2022 | Hughett et al. | |
| 2022/0370235 A1 | 11/2022 | Johannes et al. | |
| 2022/0370237 A1 | 11/2022 | Parmar et al. | |
| 2022/0387001 A1 | 12/2022 | Askenazi et al. | |
| 2022/0395390 A1 | 12/2022 | Brooks | |
| 2022/0395391 A1 | 12/2022 | Saunders et al. | |
| 2023/0018845 A1 | 1/2023 | Lee | |
| 2023/0020563 A1 | 1/2023 | Sharma et al. | |
| 2023/0031640 A1 | 2/2023 | Hughett et al. | |
| 2023/0037159 A1 | 2/2023 | Brennan et al. | |
| 2023/0052238 A1 | 2/2023 | Oluwasogo | |
| 2023/0062994 A1 | 3/2023 | Ecklund et al. | |
| 2023/0070347 A1 | 3/2023 | Watson et al. | |
| 2023/0073708 A1 | 3/2023 | Xu et al. | |
| 2023/0089032 A1 | 3/2023 | Hughett et al. | |
| 2023/0099821 A1 | 3/2023 | Radl et al. | |
| 2023/0099991 A1 | 3/2023 | Bianchi et al. | |
| 2023/0105001 A1 | 4/2023 | Whittome et al. | |
| 2023/0110577 A1 | 4/2023 | Choi | |
| 2023/0138269 A1 | 5/2023 | Abdelal et al. | |
| 2023/0145365 A1 | 5/2023 | Martin et al. | |
| 2023/0155253 A1 | 5/2023 | Yin et al. | |
| 2023/0210504 A1 | 7/2023 | Kuroda et al. | |
| 2023/0210685 A1 | 7/2023 | Fallows et al. | |
| 2023/0218426 A1 | 7/2023 | Hughett | |
| 2023/0240884 A1 | 8/2023 | Davis et al. | |
| 2023/0248562 A1 | 8/2023 | Sanchez et al. | |
| 2023/0248564 A1 | 8/2023 | Mann et al. | |
| 2023/0255812 A1 | 8/2023 | Sanchez et al. | |
| 2023/0255813 A1 | 8/2023 | Sanchez et al. | |
| 2023/0255815 A1 | 8/2023 | Newton | |
| 2023/0263650 A1 | 8/2023 | Sanchez et al. | |
| 2023/0263655 A1 | 8/2023 | Johannes et al. | |
| 2023/0277362 A1 | 9/2023 | Davis et al. | |
| 2023/0285178 A1 | 9/2023 | Sanchez et al. | |
| 2023/0293339 A1 | 9/2023 | James | |
| 2023/0301846 A1 | 9/2023 | Greenwood | |
| 2023/0355423 A1 | 11/2023 | Stevenson et al. | |
| 2023/0404791 A1 | 12/2023 | Ecklund et al. | |
| 2024/0008444 A1 | 1/2024 | Su et al. | |
| 2024/0009023 A1 | 1/2024 | Johannes et al. | |
| 2024/0024170 A1 | 1/2024 | Scott | |
| 2024/0041638 A1 | 2/2024 | Johannes et al. | |
| 2024/0058161 A1 | 2/2024 | Ulreich et al. | |
| 2024/0065881 A1 | 2/2024 | Kuroda et al. | |
| 2024/0099874 A1 | 3/2024 | Sanchez et al. | |
| 2024/0110318 A1 | 4/2024 | Bendt et al. | |
| 2024/0123134 A1 | 4/2024 | Kharkar et al. | |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |

(56) References Cited

FOREIGN PATENT DOCUMENTS

| | | |
|---|---|---|
| EP | 4025163 A1 | 7/2022 |
| EP | 3463180 B1 | 3/2023 |
| EP | 4382082 A2 | 6/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003126242 A | 5/2003 |
| JP | 2003180722 A | 7/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2010504150 A | 2/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2016521191 A | 7/2016 |
| JP | 2017014698 A | 1/2017 |
| JP | 2019525811 A | 9/2019 |
| JP | 2019170942 A | 10/2019 |
| JP | 2019533492 A | 11/2019 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A1 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |

(56) References Cited

FOREIGN PATENT DOCUMENTS

| | | |
|---|---|---|
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |

(56) References Cited

FOREIGN PATENT DOCUMENTS

| | | |
|---|---|---|
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

"" Advisory Action for U.S. Appl. No. 14/952,591 mailed Jun. 1, 2018.
"" Advisory Action for U.S. Appl. No. 15/238,427 mailed Apr. 10, 2019.
"" Advisory Action for U.S. Appl. No. 16/245,726 mailed Apr. 19, 2023.
"" Advisory Action for U.S. Appl. No. 16/369,676 mailed Mar. 24, 2023.
"" Advisory Action for U.S. Appl. No. 16/433,773 mailed Feb. 15, 2023.
"" Advisory Action for U.S. Appl. No. 16/452,258 mailed Oct. 26, 2022.
"" Advisory Action for U.S. Appl. No. 16/478,180 mailed Sep. 21, 2022.
"" Advisory Action for U.S. Appl. No. 16/478,180 mailed Sep. 7, 2023.
"" Advisory Action for U.S. Appl. No. 16/899,956 mailed Jul. 9, 2021.
"" Advisory Action for U.S. Appl. No. 16/904,868 mailed Jul. 2, 2021.
"" Advisory Action for U.S. Appl. No. 16/904,868 mailed Jun. 15, 2022.
"" Advisory Action for U.S. Appl. No. 16/905,400 mailed Feb. 16, 2022.
"" Advisory Action for U.S. Appl. No. 16/905,400 mailed Jun. 9, 2021.
"" Advisory Action for U.S. Appl. No. 17/051,550 mailed Sep. 8, 2023.
"" Advisory Action for U.S. Appl. No. 17/051,585 mailed Oct. 17, 2023.
"" Advisory Action for U.S. Appl. No. 17/444,792 mailed Aug. 25, 2023.
"" Advisory Action for U.S. Appl. No. 17/451,345 mailed Oct. 20, 2023.
"" Advisory Action for U.S. Appl. No. 17/662,700 mailed Jan. 30, 2023.
"" Corrected International Search Report and Written Opinion for International Application No. PCT/US2017/043025 mailed Jan. 11, 2018.
"" Corrected Notice of Allowability for U.S. Appl. No. 15/221,106 mailed Jul. 2, 2019.
"" Corrected Notice of Allowability for U.S. Appl. No. 15/612,325 mailed Mar. 17, 2021.
"" Corrected Notice of Allowability for U.S. Appl. No. 17/330,657 mailed Dec. 9, 2021.
"" Final Office Action for U.S. Appl. No. 14/947,759 mailed Apr. 8, 2016.
"" Final Office Action for U.S. Appl. No. 14/952,591 mailed Feb. 23, 2018.
"" Final Office Action for U.S. Appl. No. 14/952,591 mailed Nov. 1, 2019.
"" Final Office Action for U.S. Appl. No. 14/952,591 mailed Nov. 27, 2020.
"" Final Office Action for U.S. Appl. No. 15/171,968 mailed Feb. 14, 2020.
"" Final Office Action for U.S. Appl. No. 15/171,968 mailed Mar. 19, 2019.
"" Final Office Action for U.S. Appl. No. 15/221,106 mailed Jan. 23, 2019.
"" Final Office Action for U.S. Appl. No. 15/238,427 mailed Jan. 2, 2019.
"" Final Office Action for U.S. Appl. No. 15/260,103 mailed Feb. 14, 2019.
"" Final Office Action for U.S. Appl. No. 15/612,325 mailed Sep. 17, 2020.
"" Final Office Action for U.S. Appl. No. 16/245,726 mailed Nov. 25, 2022.
"" Final Office Action for U.S. Appl. No. 16/369,676 mailed Aug. 31, 2023.
"" Final Office Action for U.S. Appl. No. 16/369,676 mailed Dec. 5, 2022.
"" Final Office Action for U.S. Appl. No. 16/433,773 mailed Oct. 10, 2023.
"" Final Office Action for U.S. Appl. No. 16/433,773 mailed Oct. 25, 2022.
"" Final Office Action for U.S. Appl. No. 16/449,039 mailed Aug. 1, 2022.
"" Final Office Action for U.S. Appl. No. 16/452,145 mailed Mar. 25, 2022.
"" Final Office Action for U.S. Appl. No. 16/452,258 mailed Jun. 14, 2022.
"" Final Office Action for U.S. Appl. No. 16/478,180 mailed Jun. 22, 2022.
"" Final Office Action for U.S. Appl. No. 16/478,180 mailed May 31, 2023.
"" Final Office Action for U.S. Appl. No. 16/899,956 mailed Apr. 19, 2021.
"" Final Office Action for U.S. Appl. No. 16/904,868 mailed Mar. 10, 2022.
"" Final Office Action for U.S. Appl. No. 16/904,868 mailed Mar. 26, 2021.
"" Final Office Action for U.S. Appl. No. 16/905,400 mailed Apr. 6, 2021.
"" Final Office Action for U.S. Appl. No. 16/905,400 mailed Dec. 9, 2021.
"" Final Office Action for U.S. Appl. No. 17/051,399 mailed Mar. 9, 2023.
"" Final Office Action for U.S. Appl. No. 17/051,550 mailed May 23, 2023.

(56) References Cited

OTHER PUBLICATIONS

"" Final Office Action for U.S. Appl. No. 17/051,585 mailed Jul. 27, 2023.
"" Final Office Action for U.S. Appl. No. 17/088,272 mailed May 25, 2021.
"" Final Office Action for U.S. Appl. No. 17/444,792 mailed Jun. 15, 2023.
"" Final Office Action for U.S. Appl. No. 17/446,256 mailed Sep. 19, 2023.
"" Final Office Action for U.S. Appl. No. 17/448,811 mailed Aug. 3, 2023.
"" Final Office Action for U.S. Appl. No. 17/451,345 mailed May 3, 2023.
"" Final Office Action for U.S. Appl. No. 17/451,354 mailed Oct. 30, 2023.
"" Final Office Action for U.S. Appl. No. 17/453,260 mailed Oct. 5, 2023.
"" Final Office Action for U.S. Appl. No. 17/653,137 mailed Sep. 21, 2023.
"" Final Office Action for U.S. Appl. No. 17/655,464 mailed Sep. 1, 2023.
"" Final Office Action for U.S. Appl. No. 17/662,700 mailed Sep. 30, 2022.
"" Final Office Action for U.S. Appl. No. 29/624,661 mailed Feb. 18, 2020.
"" International Search Report and Written Opinion from International Application No. PCT/IB2021/057173 mailed Nov. 5, 2021.
"" International Search Report and Written Opinion from International Application No. PCT/US2016/049274 mailed Dec. 1, 2016.
"" International Search Report and Written Opinion from International Application No. PCT/US2017/035625 mailed Aug. 15, 2017.
"" International Search Report and Written Opinion from International Application No. PCT/US2017/043025 mailed Oct. 18, 2017.
"" International Search Report and Written Opinion from International Application No. PCT/US2018/015968 mailed Apr. 6, 2018.
"" International Search Report and Written Opinion from International Application No. PCT/US2019/029608 mailed Sep. 3, 2019.
"" International Search Report and Written Opinion from International Application No. PCT/US2019/029609 mailed Sep. 3, 2019.
"" International Search Report and Written Opinion from International Application No. PCT/US2019/029610 mailed Sep. 3, 2019.
"" International Search Report and Written Opinion from International Application No. PCT/US2019/029611 mailed Jul. 3, 2019.
"" International Search Report and Written Opinion from International Application No. PCT/US2019/029613 mailed Jul. 3, 2019.
"" International Search Report and Written Opinion from International Application No. PCT/US2019/029614 mailed Sep. 26, 2019.
"" International Search Report and Written Opinion from International Application No. PCT/US2019/029616 mailed Aug. 30, 2019.
"" International Search Report and Written Opinion from International Application No. PCT/US2020/023572 mailed Jul. 6, 2020.
"" International Search Report and Written Opinion from International Application No. PCT/US2020/033064 mailed Aug. 31, 2020.
"" International Search Report and Written Opinion from International Application No. PCT/US2020/033122 mailed Aug. 31, 2020.
"" International Search Report and Written Opinion from International Application No. PCT/US2020/040860 mailed Oct. 2, 2020.
"" International Search Report and Written Opinion from International Application No. PCT/US2020/041242 mailed Nov. 17, 2020.
"" International Search Report and Written Opinion from International Application No. PCT/US2020/041249 mailed Oct. 2, 2020.
"" International Search Report and Written Opinion from International Application No. PCT/US2020/042262 mailed Oct. 14, 2020.
"" International Search Report and Written Opinion from International Application No. PCT/US2020/043059 mailed Oct. 6, 2020.
"" International Search Report and Written Opinion from International Application No. PCT/US2020/044024 mailed Nov. 12, 2020.
"" International Search Report and Written Opinion from International Application No. PCT/US2020/046914 mailed Dec. 1, 2020.
"" International Search Report and Written Opinion from International Application No. PCT/US2020/055680 mailed Dec. 15, 2020.
"" International Search Report and Written Opinion from International Application No. PCT/US2020/057562 mailed Jan. 27, 2021.
"" International Search Report and Written Opinion from International Application No. PCT/US2020/061563 mailed Feb. 19, 2021.
"" International Search Report and Written Opinion from International Application No. PCT/US2020/065234 mailed Apr. 12, 2021.
"" International Search Report and Written Opinion from International Application No. PCT/US2020/067451 mailed Mar. 25, 2021.
"" International Search Report and Written Opinion from International Application No. PCT/US2020/067454 mailed Mar. 29, 2021.
"" International Search Report and Written Opinion from International Application No. PCT/US2020/067455 mailed Mar. 26, 2021.
"" International Search Report and Written Opinion from International Application No. PCT/US2021/015024 mailed May 18, 2021.
"" International Search Report and Written Opinion from International Application No. PCT/US2021/015787 mailed May 27, 2021.
"" International Search Report and Written Opinion from International Application No. PCT/US2021/023001 mailed Jun. 21, 2021.
"" International Search Report and Written Opinion from International Application No. PCT/US2021/024162 mailed Jul. 8, 2021.
"" International Search Report and Written Opinion from International Application No. PCT/US2021/026607 mailed Jul. 29, 2021.
"" International Search Report and Written Opinion from International Application No. PCT/US2021/027061 mailed Jul. 19, 2021.
"" International Search Report and Written Opinion from International Application No. PCT/US2021/027104 mailed Jul. 6, 2021.
"" International Search Report and Written Opinion from International Application No. PCT/US2021/027314 mailed Jul. 6, 2021.
"" International Search Report and Written Opinion from International Application No. PCT/US2021/027422 mailed Aug. 12, 2021.
"" International Search Report and Written Opinion from International Application No. PCT/US2021/027425 mailed Aug. 11, 2021.
"" International Search Report and Written Opinion from International Application No. PCT/US2021/027913 mailed Jul. 12, 2021.
"" International Search Report and Written Opinion from International Application No. PCT/US2021/027917 mailed Aug. 19, 2021.
"" International Search Report and Written Opinion from International Application No. PCT/US2021/039866 mailed Oct. 7, 2021.
"" International Search Report and Written Opinion from International Application No. PCT/US2021/043893 mailed Nov. 22, 2021.
"" International Search Report and Written Opinion from International Application No. PCT/US2021/044699 mailed Nov. 22, 2021.
"" International Search Report and Written Opinion from International Application No. PCT/US2021/045188 mailed Jan. 26, 2022.
"" International Search Report and Written Opinion from International Application No. PCT/US2021/047536 mailed Dec. 23, 2021.
"" International Search Report and Written Opinion from International Application No. PCT/US2021/048211 mailed Dec. 22, 2021.
"" International Search Report and Written Opinion from International Application No. PCT/US2021/048661 mailed Feb. 14, 2022.
"" International Search Report and Written Opinion from International Application No. PCT/US2021/049404 mailed Jan. 18, 2022.
"" International Search Report and Written Opinion from International Application No. PCT/US2021/051456 mailed Jan. 19, 2022.
"" International Search Report and Written Opinion from International Application No. PCT/US2021/053593 mailed Apr. 11, 2022.
"" International Search Report and Written Opinion from International Application No. PCT/US2021/055515 mailed Jan. 28, 2022.
"" International Search Report and Written Opinion from International Application No. PCT/US2021/056566 mailed Feb. 11, 2022.
"" International Search Report and Written Opinion from International Application No. PCT/US2021/060993 mailed Mar. 18, 2022.
"" International Search Report and Written Opinion from International Application No. PCT/US2021/062440 mailed Mar. 28, 2022.
"" International Search Report and Written Opinion from International Application No. PCT/US2022/011108 mailed Apr. 22, 2022.
"" International Search Report and Written Opinion from International Application No. PCT/US2022/011281 mailed Apr. 25, 2022.
"" International Search Report and Written Opinion from International Application No. PCT/US2022/011419 mailed Jun. 7, 2022.

(56) References Cited

OTHER PUBLICATIONS

"" International Search Report and Written Opinion from International Application No. PCT/US2022/011421 mailed Jun. 13, 2022.
"" International Search Report and Written Opinion from International Application No. PCT/US2022/012794 mailed May 3, 2022.
"" International Search Report and Written Opinion from International Application No. PCT/US2022/014285 mailed Sep. 28, 2022.
"" International Search Report and Written Opinion from International Application No. PCT/US2022/014749 mailed Sep. 28, 2022.
"" International Search Report and Written Opinion from International Application No. PCT/US2022/015026 mailed Oct. 31, 2022.
"" International Search Report and Written Opinion from International Application No. PCT/US2022/015045 mailed Sep. 9, 2022.
"" International Search Report and Written Opinion from International Application No. PCT/US2022/015073 mailed Sep. 8, 2022.
"" International Search Report and Written Opinion from International Application No. PCT/US2022/015418 mailed Nov. 11, 2022.
"" International Search Report and Written Opinion from International Application No. PCT/US2022/015420 mailed Nov. 18, 2022.
"" International Search Report and Written Opinion from International Application No. PCT/US2022/015471 mailed May 16, 2022.
"" International Search Report and Written Opinion from International Application No. PCT/US2022/015492 mailed Apr. 26, 2022.
"" International Search Report and Written Opinion from International Application No. PCT/US2022/015781 mailed May 6, 2022.
"" International Search Report and Written Opinion from International Application No. PCT/US2022/016942 mailed Jun. 8, 2022.
"" International Search Report and Written Opinion from International Application No. PCT/US2022/018159 mailed Dec. 12, 2022.
"" International Search Report and Written Opinion from International Application No. PCT/US2022/018170 mailed May 31, 2022.
"" International Search Report and Written Opinion from International Application No. PCT/US2022/019254 mailed Jun. 7, 2022.
"" International Search Report and Written Opinion from International Application No. PCT/US2022/019480 mailed Jun. 13, 2022.
"" International Search Report and Written Opinion from International Application No. PCT/US2022/021103 mailed Jun. 23, 2022.
"" International Search Report and Written Opinion from International Application No. PCT/US2022/022111 mailed Oct. 26, 2022.
"" International Search Report and Written Opinion from International Application No. PCT/US2022/023594 mailed Jul. 12, 2022.
"" International Search Report and Written Opinion from International Application No. PCT/US2022/026667 mailed Aug. 22, 2022.
"" International Search Report and Written Opinion from International Application No. PCT/US2022/030685 mailed Oct. 31, 2022.
"" International Search Report and Written Opinion from International Application No. PCT/US2022/031032 mailed Sep. 9, 2022.
"" International Search Report and Written Opinion from International Application No. PCT/US2022/032424 mailed Oct. 11, 2022.
"" International Search Report and Written Opinion from International Application No. PCT/US2022/034457 mailed Oct. 12, 2022.
"" International Search Report and Written Opinion from International Application No. PCT/US2022/034744 mailed Dec. 9, 2022.
"" International Search Report and Written Opinion from International Application No. PCT/US2022/039018 mailed Jan. 10, 2023.
"" International Search Report and Written Opinion from International Application No. PCT/US2022/039022 mailed Jan. 10, 2023.
"" International Search Report and Written Opinion from International Application No. PCT/US2022/039711 mailed Jan. 12, 2023.
"" International Search Report and Written Opinion from International Application No. PCT/US2022/039714 mailed Nov. 22, 2022.
"" International Search Report and Written Opinion from International Application No. PCT/US2022/041085 mailed Mar. 16, 2023.
"" International Search Report and Written Opinion from International Application No. PCT/US2022/041688 mailed Nov. 21, 2022.
"" International Search Report and Written Opinion from International Application No. PCT/US2022/042719 mailed Dec. 5, 2022.
"" International Search Report and Written Opinion from International Application No. PCT/US2022/042725 mailed Dec. 19, 2022.
"" International Search Report and Written Opinion from International Application No. PCT/US2022/043818 mailed Mar. 24, 2023.
"" International Search Report and Written Opinion from International Application No. PCT/US2022/044107 mailed Dec. 23, 2022.
"" International Search Report and Written Opinion from International Application No. PCT/US2022/044208 mailed May 8, 2023.
"" International Search Report and Written Opinion from International Application No. PCT/US2022/044212 mailed Jan. 20, 2023.
"" International Search Report and Written Opinion from International Application No. PCT/US2022/044243 mailed Feb. 24, 2023.
"" International Search Report and Written Opinion from International Application No. PCT/US2022/049300 mailed Jun. 6, 2023.
"" International Search Report and Written Opinion from International Application No. PCT/US2022/050909 mailed Jul. 24, 2023.
"" International Search Report and Written Opinion from International Application No. PCT/US2023/012696 mailed Jul. 6, 2023.
"" International Search Report and Written Opinion from International Application No. PCT/US2023/018474 mailed Sep. 11, 2023.
"" Issue Notification for U.S. Appl. No. 14/952,591 mailed Jul. 28, 2021.
"" Issue Notification for U.S. Appl. No. 15/171,968 mailed Mar. 3, 2021.
"" Issue Notification for U.S. Appl. No. 15/221,106 mailed Jul. 24, 2019.
"" Issue Notification for U.S. Appl. No. 15/238,427 mailed Jul. 24, 2019.
"" Issue Notification for U.S. Appl. No. 15/260,103 mailed Aug. 7, 2019.
"" Issue Notification for U.S. Appl. No. 15/611,587 mailed Feb. 20, 2019.
"" Issue Notification for U.S. Appl. No. 15/612,325 mailed Mar. 24, 2021.
"" Issue Notification for U.S. Appl. No. 16/245,726 mailed Oct. 18, 2023.
"" Issue Notification for U.S. Appl. No. 16/899,956 mailed Mar. 29, 2023.
"" Issue Notification for U.S. Appl. No. 16/905,400 mailed Nov. 30, 2022.
"" Issue Notification for U.S. Appl. No. 17/088,272 mailed Jun. 15, 2022.
"" Issue Notification for U.S. Appl. No. 17/330,657 mailed Jun. 22, 2022.
"" Issue Notification for U.S. Appl. No. 17/461,036 mailed Oct. 11, 2023.
"" Issue Notification for U.S. Appl. No. 29/624,661 mailed Aug. 4, 2021.
"" Non-Final Office Action for U.S. Appl. No. 14/947,759 mailed Mar. 17, 2016.
"" Non-Final Office Action for U.S. Appl. No. 14/952,591 mailed Aug. 1, 2017.
"" Non-Final Office Action for U.S. Appl. No. 14/952,591 mailed Mar. 20, 2020.
"" Non-Final Office Action for U.S. Appl. No. 14/952,591 mailed Mar. 21, 2019.
"" Non-Final Office Action for U.S. Appl. No. 14/952,591 mailed Sep. 28, 2018.
"" Non-Final Office Action for U.S. Appl. No. 15/171,968 mailed May 11, 2020.
"" Non-Final Office Action for U.S. Appl. No. 15/171,968 mailed Aug. 20, 2019.
"" Non-Final Office Action for U.S. Appl. No. 15/171,968 mailed Jun. 12, 2018.
"" Non-Final Office Action for U.S. Appl. No. 15/221,106 mailed Jun. 5, 2018.
"" Non-Final Office Action for U.S. Appl. No. 15/238,427 mailed Aug. 8, 2018.
"" Non-Final Office Action for U.S. Appl. No. 15/260,103 mailed Sep. 26, 2018.
"" Non-Final Office Action for U.S. Appl. No. 15/611,587 mailed Dec. 29, 2017.
"" Non-Final Office Action for U.S. Appl. No. 15/611,587 mailed Jul. 13, 2018.

(56) References Cited

OTHER PUBLICATIONS

"" Non-Final Office Action for U.S. Appl. No. 15/612,325 mailed Mar. 19, 2020.
"" Non-Final Office Action for U.S. Appl. No. 16/245,726 mailed Jan. 21, 2022.
"" Non-Final Office Action for U.S. Appl. No. 16/369,676 mailed Mar. 31, 2022.
"" Non-Final Office Action for U.S. Appl. No. 16/433,773 mailed Apr. 11, 2023.
"" Non-Final Office Action for U.S. Appl. No. 16/433,773 mailed Apr. 21, 2022.
"" Non-Final Office Action for U.S. Appl. No. 16/449,039 mailed Apr. 27, 2023.
"" Non-Final Office Action for U.S. Appl. No. 16/449,039 mailed Dec. 8, 2021.
"" Non-Final Office Action for U.S. Appl. No. 16/452,145 mailed Mar. 28, 2023.
"" Non-Final Office Action for U.S. Appl. No. 16/452,145 mailed Sep. 28, 2021.
"" Non-Final Office Action for U.S. Appl. No. 16/452,258 mailed Apr. 26, 2023.
"" Non-Final Office Action for U.S. Appl. No. 16/452,258 mailed Sep. 28, 2021.
"" Non-Final Office Action for U.S. Appl. No. 16/478,180 mailed Dec. 20, 2022.
"" Non-Final Office Action for U.S. Appl. No. 16/478,180 mailed Oct. 22, 2021.
"" Non-Final Office Action for U.S. Appl. No. 16/899,956 mailed Oct. 16, 2020.
"" Non-Final Office Action for U.S. Appl. No. 16/899,956 mailed Sep. 2, 2021.
"" Non-Final Office Action for U.S. Appl. No. 16/904,868 mailed Mar. 15, 2023.
"" Non-Final Office Action for U.S. Appl. No. 16/904,868 mailed Nov. 25, 2020.
"" Non-Final Office Action for U.S. Appl. No. 16/904,868 mailed Oct. 5, 2021.
"" Non-Final Office Action for U.S. Appl. No. 16/905,400 mailed Apr. 27, 2022.
"" Non-Final Office Action for U.S. Appl. No. 16/905,400 mailed Dec. 2, 2020.
"" Non-Final Office Action for U.S. Appl. No. 16/905,400 mailed Jul. 22, 2021.
"" Non-Final Office Action for U.S. Appl. No. 17/051,399 mailed Aug. 18, 2023.
"" Non-Final Office Action for U.S. Appl. No. 17/051,550 mailed Dec. 15, 2022.
"" Non-Final Office Action for U.S. Appl. No. 17/051,550 mailed Oct. 24, 2023.
"" Non-Final Office Action for U.S. Appl. No. 17/051,585 mailed Mar. 29, 2023.
"" Non-Final Office Action for U.S. Appl. No. 17/088,272 mailed Jan. 25, 2021.
"" Non-Final Office Action for U.S. Appl. No. 17/179,116 mailed Mar. 24, 2023.
"" Non-Final Office Action for U.S. Appl. No. 17/326,980 mailed Jul. 11, 2023.
"" Non-Final Office Action for U.S. Appl. No. 17/330,657 mailed Aug. 11, 2021.
"" Non-Final Office Action for U.S. Appl. No. 17/444,792 mailed Feb. 10, 2023.
"" Non-Final Office Action for U.S. Appl. No. 17/446,256 mailed Apr. 13, 2023.
"" Non-Final Office Action for U.S. Appl. No. 17/446,654 mailed Sep. 8, 2023.
"" Non-Final Office Action for U.S. Appl. No. 17/448,811 mailed Mar. 1, 2023.
"" Non-Final Office Action for U.S. Appl. No. 17/450,864 mailed May 10, 2023.
"" Non-Final Office Action for U.S. Appl. No. 17/451,345 mailed Dec. 7, 2022.
"" Non-Final Office Action for U.S. Appl. No. 17/451,354 mailed May 3, 2023.
"" Non-Final Office Action for U.S. Appl. No. 17/453,260 mailed Mar. 14, 2023.
"" Non-Final Office Action for U.S. Appl. No. 17/453,560 mailed Oct. 16, 2023.
"" Non-Final Office Action for U.S. Appl. No. 17/501,591 mailed Apr. 25, 2023.
"" Non-Final Office Action for U.S. Appl. No. 17/645,821 mailed Oct. 25, 2023.
"" Non-Final Office Action for U.S. Appl. No. 17/646,771 mailed Jul. 5, 2023.
"" Non-Final Office Action for U.S. Appl. No. 17/653,137 mailed Apr. 7, 2023.
"" Non-Final Office Action for U.S. Appl. No. 17/655,464 mailed Mar. 14, 2023.
"" Non-Final Office Action for U.S. Appl. No. 17/657,474 mailed Sep. 12, 2023.
"" Non-Final Office Action for U.S. Appl. No. 17/661,090 mailed Jul. 6, 2023.
"" Non-Final Office Action for U.S. Appl. No. 17/662,700 mailed Jul. 22, 2022.
"" Non-Final Office Action for U.S. Appl. No. 17/663,330 mailed Jun. 29, 2023.
"" Non-Final Office Action for U.S. Appl. No. 17/664,487 mailed Jun. 8, 2023.
"" Non-Final Office Action for U.S. Appl. No. 18/139,523 mailed Aug. 17, 2023.
"" Non-Final Office Action for U.S. Appl. No. 18/140,751 mailed Sep. 14, 2023.
"" Non-Final Office Action for U.S. Appl. No. 29/624,661 mailed Jul. 18, 2019.
"" Non-Final Office Action for U.S. Appl. No. 29/694,002 mailed Jun. 24, 2020.
"" Non-Final Office Action for U.S. Appl. No. 29/741,751 mailed Jan. 18, 2022.
"" Notice of Allowance for U.S. Appl. No. 14/952,591 mailed Apr. 5, 2021.
"" Notice of Allowance for U.S. Appl. No. 14/952,591 mailed Jul. 8, 2021.
"" Notice of Allowance for U.S. Appl. No. 15/171,968 mailed Feb. 16, 2021.
"" Notice of Allowance for U.S. Appl. No. 15/171,968 mailed Nov. 6, 2020.
"" Notice of Allowance for U.S. Appl. No. 15/221,106 mailed May 1, 2019.
"" Notice of Allowance for U.S. Appl. No. 15/238,427 mailed May 23, 2019.
"" Notice of Allowance for U.S. Appl. No. 15/260,103 mailed Jun. 7, 2019.
"" Notice of Allowance for U.S. Appl. No. 15/611,587 mailed Dec. 21, 2018.
"" Notice of Allowance for U.S. Appl. No. 15/612,325 mailed Feb. 19, 2021.
"" Notice of Allowance for U.S. Appl. No. 15/612,325 mailed Jan. 21, 2021.
"" Notice of Allowance for U.S. Appl. No. 16/245,726 mailed Jul. 6, 2023.
"" Notice of Allowance for U.S. Appl. No. 16/449,039 mailed Dec. 15, 2022.
"" Notice of Allowance for U.S. Appl. No. 16/899,956 mailed Apr. 19, 2022.
"" Notice of Allowance for U.S. Appl. No. 16/899,956 mailed Aug. 10, 2022.
"" Notice of Allowance for U.S. Appl. No. 16/899,956 mailed Dec. 1, 2022.
"" Notice of Allowance for U.S. Appl. No. 16/899,956 mailed Dec. 29, 2021.
"" Notice of Allowance for U.S. Appl. No. 16/905,400 mailed Aug. 17, 2022.

(56) References Cited

OTHER PUBLICATIONS

"" Notice of Allowance for U.S. Appl. No. 17/051,554 mailed Jul. 6, 2023.
"" Notice of Allowance for U.S. Appl. No. 17/051,554 mailed Oct. 18, 2023.
"" Notice of Allowance for U.S. Appl. No. 17/088,272 mailed Aug. 5, 2021.
"" Notice of Allowance for U.S. Appl. No. 17/088,272 mailed Mar. 4, 2022.
"" Notice of Allowance for U.S. Appl. No. 17/088,272 mailed Nov. 24, 2021.
"" Notice of Allowance for U.S. Appl. No. 17/330,657 mailed Mar. 16, 2022.
"" Notice of Allowance for U.S. Appl. No. 17/330,657 mailed Nov. 26, 2021.
"" Notice of Allowance for U.S. Appl. No. 17/461,036 mailed Feb. 22, 2023.
"" Notice of Allowance for U.S. Appl. No. 17/461,036 mailed Jun. 30, 2023.
"" Notice of Allowance for U.S. Appl. No. 17/461,036 mailed Oct. 6, 2022.
"" Notice of Allowance for U.S. Appl. No. 17/662,700 mailed Jul. 28, 2023.
"" Notice of Allowance for U.S. Appl. No. 17/662,700 mailed Mar. 28, 2023.
"" Notice of Allowance for U.S. Appl. No. 17/663,046 mailed Jan. 30, 2023.
"" Notice of Allowance for U.S. Appl. No. 18/299,788 mailed Jul. 24, 2023.
"" Notice of Allowance for U.S. Appl. No. 29/624,661 mailed Apr. 28, 2021.
"" Notice of Allowance for U.S. Appl. No. 29/624,661 mailed Jul. 10, 2020.
"" Notice of Allowance for U.S. Appl. No. 29/624,661 mailed May 14, 2020.
"" Notice of Allowance for U.S. Appl. No. 29/624,661 mailed Sep. 29, 2020.
"" Notice of Allowance for U.S. Appl. No. 29/694,002 mailed Apr. 29, 2021.
"" Notice of Allowance for U.S. Appl. No. 29/694,002 mailed Jan. 29, 2021.
"" Notice of Allowance for U.S. Appl. No. 29/694,002 mailed Oct. 16, 2020.
"" Notice of Allowance for U.S. Appl. No. 29/741,751 mailed Jun. 9, 2022.
"" Notice to File Missing Parts for U.S. Appl. No. 17/179,116 mailed Mar. 3, 2021.
"" Restriction Requirement for U.S. Appl. No. 16/433,773 mailed Dec. 7, 2021.
"" Restriction Requirement for U.S. Appl. No. 16/478,180 mailed May 25, 2021.
"" Restriction Requirement for U.S. Appl. No. 17/051,600 mailed Sep. 21, 2023.
"" Restriction Requirement for U.S. Appl. No. 17/326,980 mailed Mar. 20, 2023.
"" Restriction Requirement for U.S. Appl. No. 17/446,256 mailed Jan. 23, 2023.
"" Restriction Requirement for U.S. Appl. No. 17/645,821 mailed Jul. 12, 2023.
"" Restriction Requirement for U.S. Appl. No. 17/646,771 mailed Apr. 6, 2023.
"" Restriction Requirement for U.S. Appl. No. 17/657,474 mailed Jun. 30, 2023.
"" Restriction Requirement for U.S. Appl. No. 18/134,857 mailed Oct. 23, 2023.
"" Text Messages to Lorena Eckert Re Prototype PureWick Holder dated Apr. 16, 2022.
"" U.S. Appl. No. 14/625,469, filed Feb. 28, 2015.
"" U.S. Appl. No. 14/947,759, filed Nov. 20, 2015.
"" U.S. Appl. No. 14/952,591, filed Nov. 25, 2015.
"" U.S. Appl. No. 15/171,968, filed Jun. 2, 2016.
"" U.S. Appl. No. 15/221,106, filed Jul. 27, 2016.
"" U.S. Appl. No. 15/260,103, filed Sep. 8, 2016.
"" U.S. Appl. No. 15/384,196, filed Dec. 19, 2016.
"" U.S. Appl. No. 15/611,587, filed Jun. 1, 2017.
"" U.S. Appl. No. 15/612,325, filed Jun. 2, 2017.
"" U.S. Appl. No. 16/245,726, filed Jan. 11, 2019.
"" U.S. Appl. No. 16/369,676, filed Mar. 29, 2019.
"" U.S. Appl. No. 16/433,773, filed Jun. 6, 2019.
"" U.S. Appl. No. 16/449,039, filed Jun. 21, 2019.
"" U.S. Appl. No. 16/452,145, filed Jun. 25, 2019.
"" U.S. Appl. No. 16/452,258, filed Jun. 25, 2019.
"" U.S. Appl. No. 16/478,180, filed Jul. 16, 2019.
"" U.S. Appl. No. 16/904,868, filed Jun. 18, 2020.
"" U.S. Appl. No. 16/905,400, filed Jun. 18, 2020.
"" U.S. Appl. No. 17/051,550, filed Oct. 29, 2020.
"" U.S. Appl. No. 17/051,554, filed Oct. 29, 2020.
"" U.S. Appl. No. 17/051,585, filed Oct. 29, 2020.
"" U.S. Appl. No. 17/051,600, filed Oct. 29, 2020.
"" U.S. Appl. No. 17/088,272, filed Nov. 3, 2020.
"" U.S. Appl. No. 17/179,116, filed Feb. 18, 2021.
"" U.S. Appl. No. 17/330,657, filed May 26, 2021.
"" U.S. Appl. No. 17/378,015, filed Jul. 16, 2021.
"" U.S. Appl. No. 17/394,055, filed Aug. 4, 2021.
"" U.S. Appl. No. 17/444,825, filed Aug. 10, 2021.
"" U.S. Appl. No. 17/446,256, filed Aug. 27, 2021.
"" U.S. Appl. No. 17/446,654, filed Sep. 1, 2021.
"" U.S. Appl. No. 17/447,123, filed Sep. 8, 2021.
"" U.S. Appl. No. 17/450,864, filed Oct. 14, 2021.
"" U.S. Appl. No. 17/451,345, filed Oct. 19, 2021.
"" U.S. Appl. No. 17/451,354, filed Oct. 19, 2021.
"" U.S. Appl. No. 17/453,260, filed Nov. 2, 2021.
"" U.S. Appl. No. 17/453,560, filed Nov. 4, 2021.
"" U.S. Appl. No. 17/461,036 mailed Aug. 30, 2021.
"" U.S. Appl. No. 17/501,591, filed Oct. 14, 2021.
"" U.S. Appl. No. 17/595,747, filed Nov. 23, 2021.
"" U.S. Appl. No. 17/597,408, filed Jan. 5, 2022.
"" U.S. Appl. No. 17/597,673, filed Jan. 18, 2022.
"" U.S. Appl. No. 17/614,173, filed Nov. 24, 2021.
"" U.S. Appl. No. 17/631,619, filed Jan. 31, 2022.
"" U.S. Appl. No. 17/645,821, filed Dec. 23, 2021.
"" U.S. Appl. No. 17/646,771, filed Jan. 3, 2022.
"" U.S. Appl. No. 17/653,314, filed Mar. 3, 2022.
"" U.S. Appl. No. 17/653,920, filed Mar. 8, 2022.
"" U.S. Appl. No. 17/655,464, filed Mar. 18, 2022.
"" U.S. Appl. No. 17/657,474, filed Mar. 31, 2022.
"" U.S. Appl. No. 17/661,090, filed Apr. 28, 2022.
"" U.S. Appl. No. 17/662,700, filed May 10, 2022.
"" U.S. Appl. No. 17/663,046, filed May 12, 2022.
"" U.S. Appl. No. 17/664,487, filed May 23, 2022.
"" U.S. Appl. No. 17/664,914, filed May 25, 2022.
"" U.S. Appl. No. 17/749,340, filed May 20, 2022.
"" U.S. Appl. No. 17/754,736, filed Apr. 11, 2022.
"" U.S. Appl. No. 17/756,201, filed May 19, 2022.
"" U.S. Appl. No. 17/758,152, filed Jun. 29, 2022.
"" U.S. Appl. No. 17/758,316, filed Jul. 1, 2022.
"" U.S. Appl. No. 17/759,697, filed Jul. 28, 2022.
"" U.S. Appl. No. 17/878,268, filed Aug. 1, 2022.
"" U.S. Appl. No. 17/907,125, filed Sep. 23, 2022.
"" U.S. Appl. No. 17/912,147, filed Sep. 16, 2022.
"" U.S. Appl. No. 17/929,887, filed Sep. 6, 2022.
"" U.S. Appl. No. 17/930,238, filed Sep. 7, 2022.
"" U.S. Appl. No. 17/933,590, filed Sep. 20, 2022.
"" U.S. Appl. No. 17/996,064, filed Oct. 12, 2022.
"" U.S. Appl. No. 17/996,155, filed Oct. 13, 2022.
"" U.S. Appl. No. 17/996,253, filed Oct. 14, 2022.
"" U.S. Appl. No. 17/996,468, filed Oct. 18, 2022.
"" U.S. Appl. No. 17/996,556, filed Oct. 19, 2022.
"" U.S. Appl. No. 18/003,029, filed Dec. 22, 2022.
"" U.S. Appl. No. 18/006,807, filed Jan. 25, 2023.
"" U.S. Appl. No. 18/007,105, filed Jan. 27, 2023.
"" U.S. Appl. No. 18/041,109, filed Feb. 9, 2023.
"" U.S. Appl. No. 18/042,842, filed Feb. 24, 2023.

(56) References Cited

OTHER PUBLICATIONS

"" U.S. Appl. No. 18/043,618, filed Mar. 1, 2023.
"" U.S. Appl. No. 18/115,444, filed Feb. 28, 2023.
"" U.S. Appl. No. 18/134,857, filed Apr. 14, 2023.
"" U.S. Appl. No. 18/140,163, filed Apr. 27, 2023.
"" U.S. Appl. No. 18/140,751, filed Apr. 28, 2023.
"" U.S. Appl. No. 18/164,800, filed Feb. 6, 2023.
"" U.S. Appl. No. 18/198,464, filed May 17, 2023.
"" U.S. Appl. No. 18/246,121, filed Mar. 21, 2023.
"" U.S. Appl. No. 18/247,986, filed Apr. 5, 2023.
"" U.S. Appl. No. 18/259,626, filed Jun. 28, 2023.
"" U.S. Appl. No. 18/260,122, filed Jun. 30, 2023.
"" U.S. Appl. No. 18/260,391, filed Jul. 5, 2023.
"" U.S. Appl. No. 18/260,394, filed Jul. 5, 2023.
"" U.S. Appl. No. 18/263,800, filed Aug. 1, 2023.
"" U.S. Appl. No. 18/264,004, filed Aug. 2, 2023.
"" U.S. Appl. No. 18/265,736, filed Jun. 7, 2023.
"" U.S. Appl. No. 18/299,788, filed Apr. 13, 2023.
"" U.S. Appl. No. 18/335,579, filed Jun. 15, 2023.
"" U.S. Appl. No. 18/373,424, filed Sep. 27, 2023.
"" U.S. Appl. No. 18/376,274, filed Oct. 3, 2023.
"" U.S. Appl. No. 18/548,152, filed Aug. 28, 2023.
"" U.S. Appl. No. 18/549,387, filed Sep. 7, 2023.
"" U.S. Appl. No. 18/549,658, filed Sep. 8, 2023.
"" U.S. Appl. No. 18/553,625, filed Oct. 2, 2023.
"" U.S. Appl. No. 18/556,945, filed Oct. 24, 2023.
"" U.S. Appl. No. 29/741,751, filed Jul. 15, 2020.
"" U.S. Appl. No. 61/955,537, filed Mar. 19, 2014.
"" U.S. Appl. No. 62/082,279, filed Nov. 20, 2014.
"" U.S. Appl. No. 62/084,078, filed Nov. 25, 2014.
"" U.S. Appl. No. 62/414,963, filed Oct. 31, 2016.
"" U.S. Appl. No. 62/452,437, filed Jan. 31, 2017.
"" U.S. Appl. No. 62/485,578, filed Apr. 14, 2017.
"" U.S. Appl. No. 62/665,297, filed May 1, 2018.
"" U.S. Appl. No. 62/665,302, filed May 1, 2018.
"" U.S. Appl. No. 62/665,317, filed May 1, 2018.
"" U.S. Appl. No. 62/665,321, filed May 1, 2018.
"" U.S. Appl. No. 62/665,331, filed May 1, 2018.
"" U.S. Appl. No. 62/665,335, filed May 1, 2018.
"" U.S. Appl. No. 62/853,279, filed May 28, 2019.
"" U.S. Appl. No. 62/853,889 filed May 29, 2019.
"" U.S. Appl. No. 62/864,656, filed Jun. 21, 2019.
"" U.S. Appl. No. 62/873,045, filed Jul. 11, 2019.
"" U.S. Appl. No. 62/873,048, filed Jul. 11, 2019.
"" U.S. Appl. No. 62/876,500, filed Jul. 19, 2019.
"" U.S. Appl. No. 62/877,558, filed Jul. 23, 2019.
"" U.S. Appl. No. 62/883,172, filed Aug. 6, 2019.
"" U.S. Appl. No. 62/889,149, filed Aug. 20, 2019.
"" U.S. Appl. No. 62/923,279, filed Oct. 18, 2019.
"" U.S. Appl. No. 62/926,767, filed Oct. 28, 2019.
"" U.S. Appl. No. 62/935,337, filed Nov. 14, 2019.
"" U.S. Appl. No. 62/938,447, filed Nov. 21, 2019.
"" U.S. Appl. No. 62/949,187, filed Dec. 17, 2019.
"" U.S. Appl. No. 62/956,756, filed Jan. 3, 2020.
"" U.S. Appl. No. 62/956,767, filed Jan. 3, 2020.
"" U.S. Appl. No. 62/956,770, filed Jan. 3, 2020.
"" U.S. Appl. No. 62/967,158, filed Jan. 26, 2020.
"" U.S. Appl. No. 62/967,977, filed Jan. 30, 2020.
"" U.S. Appl. No. 62/991,754, filed Mar. 19, 2020.
"" U.S. Appl. No. 62/994,912, filed Mar. 26, 2020.
"" U.S. Appl. No. 63/008,112, filed Apr. 10, 2020.
"" U.S. Appl. No. 63/011,445, filed Apr. 17, 2020.
"" U.S. Appl. No. 63/011,487, filed Apr. 17, 2020.
"" U.S. Appl. No. 63/011,571, filed Apr. 17, 2020.
"" U.S. Appl. No. 63/011,657, filed Apr. 17, 2020.
"" U.S. Appl. No. 63/011,760, filed Apr. 17, 2020.
"" U.S. Appl. No. 63/012,347, filed Apr. 20, 2020.
"" U.S. Appl. No. 63/012,384, filed Apr. 20, 2020.
"" U.S. Appl. No. 63/030,685, filed May 27, 2020.
"" U.S. Appl. No. 63/047,374, filed Jul. 2, 2020.
"" U.S. Appl. No. 63/061,241, filed Aug. 5, 2020.
"" U.S. Appl. No. 63/061,244, filed Aug. 5, 2020.
"" U.S. Appl. No. 63/061,834, filed Aug. 6, 2020.
"" U.S. Appl. No. 63/064,017, filed Aug. 11, 2020.
"" U.S. Appl. No. 63/064,126, filed Aug. 11, 2020.
"" U.S. Appl. No. 63/067,542, filed Aug. 19, 2020.
"" U.S. Appl. No. 63/071,438, filed Aug. 28, 2020.
"" U.S. Appl. No. 63/073,545, filed Sep. 2, 2020.
"" U.S. Appl. No. 63/073,553, filed Sep. 2, 2020.
"" U.S. Appl. No. 63/074,051, filed Sep. 3, 2020.
"" U.S. Appl. No. 63/074,066, filed Sep. 3, 2020.
"" U.S. Appl. No. 63/076,032, filed Sep. 9, 2020.
"" U.S. Appl. No. 63/076,474, filed Sep. 10, 2020.
"" U.S. Appl. No. 63/076,477, filed Sep. 10, 2020.
"" U.S. Appl. No. 63/082,261, filed Sep. 23, 2020.
"" U.S. Appl. No. 63/088,506, filed Oct. 7, 2020.
"" U.S. Appl. No. 63/088,511, filed Oct. 7, 2020.
"" U.S. Appl. No. 63/094,464, filed Oct. 21, 2020.
"" U.S. Appl. No. 63/094,498, filed Oct. 21, 2020.
"" U.S. Appl. No. 63/094,594, filed Oct. 21, 2020.
"" U.S. Appl. No. 63/094,608, filed Oct. 21, 2020.
"" U.S. Appl. No. 63/094,626, filed Oct. 21, 2020.
"" U.S. Appl. No. 63/094,646, filed Oct. 21, 2020.
"" U.S. Appl. No. 63/109,066, filed Nov. 3, 2020.
"" U.S. Appl. No. 63/109,084, filed Nov. 3, 2020.
"" U.S. Appl. No. 63/112,417, filed Nov. 11, 2020.
"" U.S. Appl. No. 63/119,161, filed Nov. 30, 2020.
"" U.S. Appl. No. 63/124,271, filed Dec. 11, 2020.
"" U.S. Appl. No. 63/133,892, filed Jan. 5, 2021.
"" U.S. Appl. No. 63/134,287, filed Jan. 6, 2021.
"" U.S. Appl. No. 63/134,450, filed Jan. 6, 2021.
"" U.S. Appl. No. 63/134,631, filed Jan. 7, 2021.
"" U.S. Appl. No. 63/134,632, filed Jan. 7, 2021.
"" U.S. Appl. No. 63/134,754, filed Jan. 7, 2021.
"" U.S. Appl. No. 63/138,878, filed Jan. 19, 2021.
"" U.S. Appl. No. 63/146,946, filed Feb. 8, 2021.
"" U.S. Appl. No. 63/147,013, filed Feb. 8, 2021.
"" U.S. Appl. No. 63/147,299, filed Feb. 9, 2021.
"" U.S. Appl. No. 63/148,723, filed Feb. 12, 2021.
"" U.S. Appl. No. 63/150,640, filed Feb. 18, 2021.
"" U.S. Appl. No. 63/154,248, filed Feb. 26, 2021.
"" U.S. Appl. No. 63/155,395, filed Mar. 2, 2021.
"" U.S. Appl. No. 63/157,007, filed Mar. 5, 2021.
"" U.S. Appl. No. 63/157,014, filed Mar. 5, 2021.
"" U.S. Appl. No. 63/159,142, filed Mar. 10, 2021.
"" U.S. Appl. No. 63/159,186, filed Mar. 10, 2021.
"" U.S. Appl. No. 63/159,210, filed Mar. 10, 2021.
"" U.S. Appl. No. 63/165,273, filed Mar. 24, 2021.
"" U.S. Appl. No. 63/165,384, filed Mar. 24, 2021.
"" U.S. Appl. No. 63/171,165, filed Apr. 6, 2021.
"" U.S. Appl. No. 63/172,975, filed Apr. 9, 2021.
"" U.S. Appl. No. 63/181,695, filed Apr. 29, 2021.
"" U.S. Appl. No. 63/191,558, filed May 21, 2021.
"" U.S. Appl. No. 63/192,274, filed May 24, 2021.
"" U.S. Appl. No. 63/192,289, filed May 24, 2021.
"" U.S. Appl. No. 63/193,235, filed May 26, 2021.
"" U.S. Appl. No. 63/193,406, filed May 26, 2021.
"" U.S. Appl. No. 63/193,891, filed May 27, 2021.
"" U.S. Appl. No. 63/208,262, filed Jun. 8, 2021.
"" U.S. Appl. No. 63/214,551, filed Jun. 24, 2021.
"" U.S. Appl. No. 63/214,570, filed Jun. 24, 2021.
"" U.S. Appl. No. 63/215,017, filed Jun. 25, 2021.
"" U.S. Appl. No. 63/228,244, filed Aug. 2, 2021.
"" U.S. Appl. No. 63/228,252, filed Aug. 2, 2021.
"" U.S. Appl. No. 63/228,258, filed Aug. 2, 2021.
"" U.S. Appl. No. 63/230,894, filed Aug. 9, 2021.
"" U.S. Appl. No. 63/230,897, filed Aug. 9, 2021.
"" U.S. Appl. No. 63/238,457, filed Aug. 30, 2021.
"" U.S. Appl. No. 63/238,477, filed Aug. 30, 2021.
"" U.S. Appl. No. 63/241,328, filed Sep. 7, 2021.
"" U.S. Appl. No. 63/241,562, filed Sep. 8, 2021.
"" U.S. Appl. No. 63/241,564, filed Sep. 8, 2021.
"" U.S. Appl. No. 63/241,575, filed Sep. 8, 2021.

(56) References Cited

OTHER PUBLICATIONS

"" U.S. Appl. No. 63/246,972, filed Sep. 22, 2021.
"" U.S. Appl. No. 63/247,375, filed Sep. 23, 2021.
"" U.S. Appl. No. 63/247,478, filed Sep. 23, 2021.
"" U.S. Appl. No. 63/247,491, filed Sep. 23, 2021.
"" U.S. Appl. No. 63/299,208, filed Jan. 13, 2022.
"" U.S. Appl. No. 63/308,190, filed Feb. 9, 2022.
"" Defendant and Counterclaim Plaintiff Sage Products, LLC's Answer, Defenses, and Counterclaims to Plaintiff's Amended Complaint , Nov. 1, 2019.
"" *PureWick Corporation v. Sage Products, LLC* Transcripts vol. 2 , Mar. 29, 2022.
"" *PureWick Corporation v. Sage Products, LLC* Transcripts vol. 3 , Mar. 30, 2022.
"" *PureWick Corporation v. Sage Products, LLC* Transcripts vol. 4 , Mar. 31, 2022.
"" Memorandum Order , Feb. 2021.
"" Sage's Initial Invalidity Contentions Regarding U.S. Pat. No. 8,287,508; U.S. Pat. No. 10,226,375; and U.S. Pat. No. 10,390,989 , May 29, 2020.
"" Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407 , Aug. 21, 2020.
"" Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407.
"" Boehringer CareDry System—Second Generation for Non-Invasive Urinary Management for Females , Mar. 2021.
"" *PureWick Corporation v. Sage Products, LLC* Transcripts vol. 5 , Apr. 1, 2022.
"" Excerpts from the 508 (U.S. Pat. No. 8,278,508) Patent's Prosecution History , 2020.
"" *PureWick Corporation v. Sage Products, LLC* Transcripts vol. 1 , Mar. 28, 2022.
"" Plaintiff's Opening Claim Construction Brief , Oct. 16, 2020.
"" Plaintiff's Identification of Claim Terms and Proposed Constructions.
"" PureWick's Response to Interrogatory No. 9 in *PureWick, LLC v. Sage Products, LLC* , Mar. 23, 2020.
"" Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407.
"" Decision Granting Institution of Inter Partes Review for U.S. Pat. No. 8,287,508 , Feb. 17, 2021.
"" Corrected Certificate of Service , 2020.
"" Declaration of Diane K. Newman Curriculum Vitae , 2020.
"3 Devices Take Top Honors in Dare-to-Dream Medtech Design Contest", R+D Digest , Nov. 2013 , 1 page.
"Advanced Mission Extender Device (AMDX) Products", Omni Medical Systems, Inc. , 15 pages.
"AMXD Control Starter Kit", Omni Medical Systems, Inc. , 1 page.
"AMXD Control Starter Kit Brochure", https://www.omnimedicalsys.com/index.php?page=products , 8 pages.
"AMXDmax Advanced Mission Extender Device User & Maintenance Guide", Omni Medical , Jan. 11, 2010 , 10 pages.
"AMXDmax Development History 2002-2014", Omni Medical Systems, Inc. , 2 pages.
"AMXDmax In-Flight Bladder Relief", Omni Medical; Omni Medical Systems, Inc. , 2015.
"AMXDX—Advanced Mission Extender Device Brochure", Omni Medical , 2 pages.
"Combat Force Multiplier in Flight Bladder Relief Cockpit Essential Equipment Brochure", Omni Medical , 20 pages.
"External Urine Management for Female Anatomy", https://www.stryker.com/us/en/sage/products/sage-primafit.html , Jul. 2020 , 4 pages.
"GSA Price List", Omni Medical , Apr. 2011 , 2 pages.
"High Absorbancy Cellulose Acetate Electrospun Nanofibers for Feminine Hygiene Application", https://www.sciencedirect.com/science/article/abs/pii/S2352940716300701?via%3Dihub , Jul. 2016 , 3 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020 , 3 pages.
"How Period Panties Work", www.shethinx.com/pages/thinx-itworks , 2020 , 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract , 2015 , 5 pages.
"In Flight Bladder Relief", Omni Medical , 14 pages.
"Letter to Mark Harvie of Omni Measurement Systems", Department of Veterans Affairs , Nov. 1, 2007 , 11 pages.
"Making Women's Sanitary Products Safer and Cheaper", https://www.elsevier.com/connect/making-womens-sanitary-products-safer-and-cheaper , Sep. 2016 , 10 pages.
"Novel Nanofibers Make Safe and Effective Absorbent for Sanitary Products", https://www.materialstoday.com/nanomaterials/news/nanofibers-make-safe-and-effective-absorbent/ , Oct. 2016 , 3 pages.
"Research and Development Work Relating to Assistive Technology Jun. 2005", British Department of Health , Nov. 2006 , 40 pages.
"Revised AMXDmax Advanced Mission Extender Device User & Maintenance Guide", Omni Medical Systems , Oct. 8, 2019 , 52 pages.
"Rising Warrior Insulated Gallon Jug Cover", https://www.amazon.com/Rising-Warrior-Insulated-Sleeve , 2021 , 2 pages.
"Step by Step How Ur24 WorksHome", http://medicalpatentur24.com , Aug. 30, 2017 , 4 pages.
"Underwear that absorbs your period", Thinx! , 7 pages.
"Urine Bag Cover—Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000 , 2022 , 1 page.
"User & Maintenance Guide", Omni Medical , 2007 , 16 pages.
"Vinyl Dust Cover, Janome #741811000, Janome, Sewing Parts Online", https://www.sewingpartsonline.com/vinyl-dust-cover-janome-74181000 , 2020 , 2 pages.
"Winners Announced for Dare-to-Dream Medtech Design Challenge", https://www.mddionline.com/design-engineering/winners-announced-dare-dream-medtech-design-challenge , 2014 , 4 pages.
Ali , "Sustainability Assessment: Seventh Generation Diapers versus gDiapers", The University of Vermont , Dec. 6, 2011 , pp. 1-31.
Autumn , et al. , "Frictional adhesion: a new angle on gecko attachment", The Journal of Experimental Biology , 2006 , pp. 3569-3579.
Cañas , et al. , "Effect of nano- and micro-roughness on adhesion of bioinspired micropatterned surfaces", Acta Biomaterialia 8 , 2012 , pp. 282-288.
Chaudhary , et al. , "Bioinspired dry adhesive: Poly(dimethylsiloxane) grafted with poly(2-ethylhexyl acrylate) brushes", European Polymer Journal , 2015 , pp. 432-440.
Dai , et al. , "Non-sticky and Non-slippery Biomimetic Patterned Surfaces", Journal of Bionic Engineering , Mar. 2020 , pp. 326-334.
Espinoza-Ramirez , "Nanobiodiversity and Biomimetic Adhesives Development: From Nature to Production and Application", Journal of Biomaterials and Nanobiotechnology , pp. 78-101 , 2019.
Hollister , "Female Urinary and Pouch and Male Urinary Pouch Brochure", www.hollister.com , 2011 , 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com.
Hwang , et al. , "Multifunctional Smart Skin Adhesive Patches for Advanced Health Care", Adv. Healthcare Mater , 2018 , pp. 1-20.
Jagota , et al. , "Adhesion, friction, and compliance of bio-mimetic and bio-inspired structured interfaces", Materials Science and Engineering , 2011 , pp. 253-292.

(56) References Cited

OTHER PUBLICATIONS

Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Merriam-Webster Dictionary, , "Embed Definition & Meaning", https://www.merriam-webster.com/dictionary/embed last accessed Aug. 3, 2023, 2003.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", , 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
PUREWICK, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of The Royal Society—Interface, 2014, pp. 1-6.
Vinas, "A Solution for an Awkward—But Serious—Subject", http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/904,868 mailed Jan. 2, 2024.
Advisory Action for U.S. Appl. No. 17/179,116 mailed Jan. 8, 2024.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Aug. 7, 2024.
Final Office Action for U.S. Appl. No. 17/661,090 mailed Dec. 11, 2023.
Final Office Action for U.S. Appl. No. 17/663,330 mailed Dec. 12, 2023.

(56) References Cited

OTHER PUBLICATIONS

Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/134,857 mailed Jul. 25, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,145 mailed Nov. 2, 2023.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Notice of Allowance for U.S. Appl. No. 16/369,676 mailed Jun. 17, 2024.
Notice of Allowance for U.S. Appl. No. 16/369,676 mailed Nov. 14, 2023.

(56) References Cited

OTHER PUBLICATIONS

Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/051,550 mailed Feb. 7, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/664,914 mailed Jul. 26, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/299,788 mailed Nov. 6, 2023.
Restriction Requirement for U.S. Appl. No. 17/625,941 mailed Aug. 7, 2024.
Restriction Requirement for U.S. Appl. No. 17/667,097 mailed Mar. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 17/451,719, filed Oct. 19, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.

\* cited by examiner

FLUID COLLECTION ASSEMBLIES INCLUDING AN ADJUSTABLE SPINE

BACKGROUND

An patient may have limited or impaired mobility such that typical urination processes are challenging or impossible. For example, the patient may have surgery or a disability that impairs mobility. In another example, the patient may have restricted travel conditions such as those experience by pilots, drivers, and workers in hazardous areas. Additionally, fluid collection from the patient may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection assemblies continue to seek new and improved devices, systems, and methods to collect urine.

SUMMARY

Embodiments disclosed herein include fluid collection assemblies having an adjustable spine, fluid collection systems including the same, and methods of using the same. In an embodiment, a fluid collection assembly is disclosed. The fluid collection assembly includes a fluid impermeable barrier including at least one outer surface and at least one inner surface opposite the at least one outer surface. The fluid impermeable barrier defines at least a chamber, at least one opening, and a fluid outlet. The fluid collection assembly also includes at least one porous material disposed in the chamber and an adjustable spine disposed in the chamber or attached to the at least one outer surface of the fluid impermeable barrier. The adjustable spine includes a first strip and a second strip configured to switch at least from a relaxed configuration to a stressed configuration. At least one of the first strip or the second strip includes one or more steps, the one or more steps configured to inhibit relaxation of the second strip when the second strip exhibits the stressed configuration. At least a portion of the fluid collection assembly exhibits a first shape when the second strip exhibits the relaxed configuration and a second shape when the second strip exhibits the stressed configuration. The first shape is different than the second shape.

In an embodiment, a fluid collection system is disclosed. The fluid collection system includes a fluid storage container configured to hold one or more bodily fluids therein. The fluid collection system also includes a fluid collection assembly. The fluid collection assembly includes a fluid impermeable barrier including at least one outer surface and at least one inner surface opposite the at least one outer surface. The fluid impermeable barrier defines at least a chamber, at least one opening, and a fluid outlet. The fluid collection assembly also includes at least one porous material disposed in the chamber and an adjustable spine disposed in the chamber or attached to the at least one outer surface of the fluid impermeable barrier. The adjustable spine includes a first strip and a second strip configured to switch at least from a relaxed configuration to a stressed configuration. At least one of the first strip or the second strip includes one or more steps, the one or more steps configured to inhibit relaxation of the second strip when the second strip exhibits the stressed configuration. At least a portion of the fluid collection assembly exhibits a first shape when the second strip exhibits the relaxed configuration and a second shape when the second strip exhibits the stressed configuration. The first shape is different than the second shape. The fluid collection system further includes a vacuum source in fluid communication with the fluid storage container and the fluid collection assembly. The vacuum source is configured to draw the one or more bodily fluids from the fluid collection assembly and deposit the one or more bodily fluids in the fluid storage container via one or more conduits.

In an embodiment, a method to collection one or more bodily fluids is disclosed. The method includes positioning at least one opening of a fluid collection assembly adjacent to a female urethral opening that exhibits a first shape. The fluid collection assembly includes a fluid impermeable barrier including at least one outer surface and at least one inner surface opposite the at least one outer surface. The fluid impermeable barrier defines at least a chamber, at least one opening, and a fluid outlet. The fluid collection assembly also includes at least one porous material disposed in the chamber and an adjustable spine disposed in the chamber or attached to the at least one outer surface of the fluid impermeable barrier. The adjustable spine includes a first strip and a second strip in a relaxed configuration. At least one of the first strip or the second strip includes one or more steps. The method also includes shaping the fluid collection assembly from the first shape to a second shape that is different than the first shape by switching the second strip from the relaxed configuration to a stressed configuration. The method further includes engaging the one or more steps to inhibit relaxation of the second strip.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
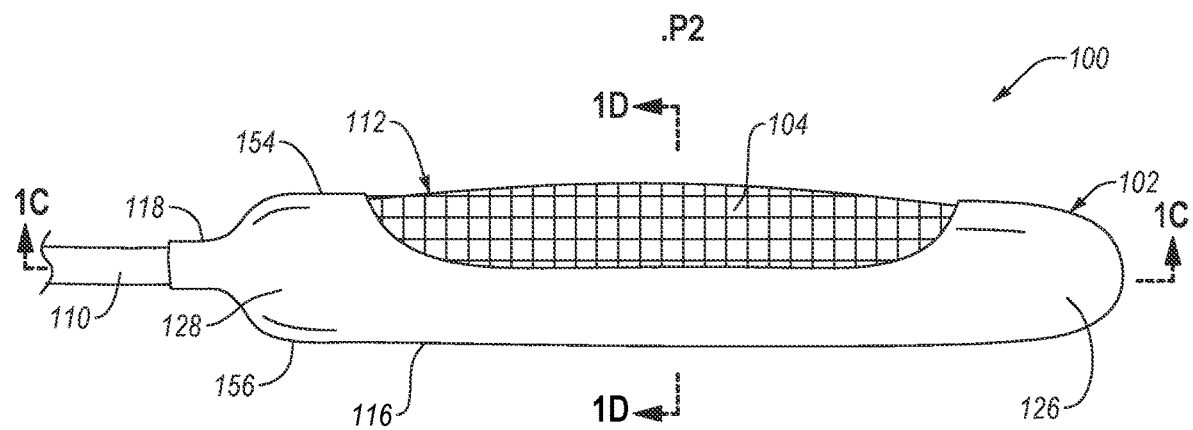
FIGS. 1A and 1B are isometric views of fluid collection assembly exhibiting a first shape and a second shape, respectively, according to an embodiment.

Embodiments disclosed herein include fluid collection assemblies having an adjustable spine, fluid collection systems including the same, and methods of using the same. An example fluid collection assembly includes a fluid impermeable barrier defining at least a chamber, at least one opening, and a fluid outlet. The fluid collection assembly also includes at least one porous material disposed in the chamber and an adjustable spine. The adjustable spine is configured to selectively change the shape of at least a portion of the fluid collection assembly. For example, the adjustable spine includes a first strip and a second strip. The second strip is configured to switch from at least a relaxed configuration to a stressed configuration. The fluid collection assembly may exhibit a first shape when the second strip is in the relaxed configuration and a second shape that is different than the first shape when the second strip is in the stressed configuration. At least one of the first or second strip includes one or more steps that are configured to engage with the other of the first or second strip. Once engaged and when the second strip is in a stressed configuration, the one or more steps may inhibit switching the second strip to a more relaxed configuration, such as from the stressed configuration to the relaxed configuration.

The adjustable spine may decrease the likelihood that the fluid collection assembly leaks one or more bodily fluids during use than at least some conventional fluid collection assemblies. For example, the fluid collection assemblies disclosed herein may be provided while exhibiting the first shape. The opening of the fluid collection assembly may be positioned adjacent to a urethral opening of a patient (i.e., an individual using the fluid collection assembly). Similar to some conventional fluid collection assemblies, there may exist gaps between the fluid collection assembly and the region about the urethral opening when the fluid collection assembly exhibits the first shape. The gaps between the fluid collection assembly and the region about the urethral opening may allow the one or more bodily fluids discharged from the patient (e.g., urine, blood, sweat, etc.) to leak from the fluid collection assembly. The leaked bodily fluids may create unsanitary conditions, require cleaning, make the patient embarrassed, and cause the patient to remain in contact with the bodily fluids which may cause skin degradation. Unlike some conventional fluid collection assemblies, the shape of the fluid collection assemblies disclosed herein may be controllably changed to eliminate or at least reduce the gaps between the fluid collection assembly and the region about the urethral opening. For example, as previously discussed, the second strip of the adjustable spine may be switched from the relaxed configuration to the stressed configuration which, in turn, changes the shape of the fluid collection assembly from the first shape to the second shape. The second shape of the fluid collection assembly may eliminate or at least decrease the size and/or quantity of gaps that are present between the fluid collection assembly and the urethral opening of the patient. As such, changing the shape of the fluid collection assembly from the first shape to the second shape may reduce the likelihood that the fluid collection assembly leaks than if the shape of the fluid collection assembly was not changeable.

After positioning the fluid collection assembly adjacent to the female urethral opening and shaping the fluid collection assembly, the fluid collection assembly may receive one or more bodily fluids from the patient. The bodily fluids may flow through the opening and into the chamber. Such bodily fluids may be received by the porous material which moves the bodily fluids away from the opening to minimize the likelihood that the bodily fluids leak from the fluid collection assembly and to maintain the patient dry. The bodily fluids may then be removed from the chamber through the fluid outlet. For example, the fluid collection assembly may include a conduit positioned through the fluid outlet and the conduit may include an inlet that is positioned within the chamber. The conduit may be in fluid communication with a vacuum source that applies a suction force to the chamber. The suction force may remove the bodily fluids from the chamber and flow the bodily fluids into and through the conduit. The conduit may be in fluid communication with a fluid storage container and the bodily fluids may be deposited in to the fluid storage container.

Figure 1B:
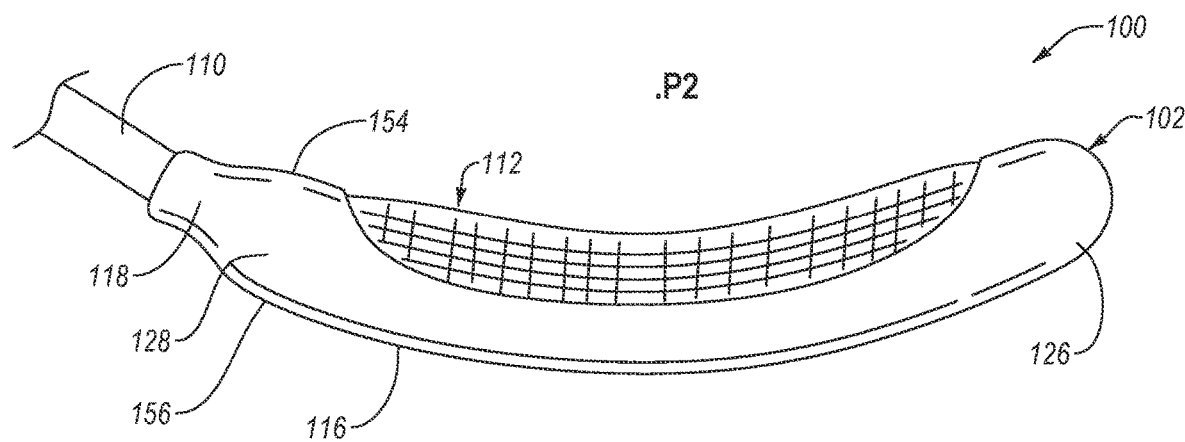
Figure 1C:
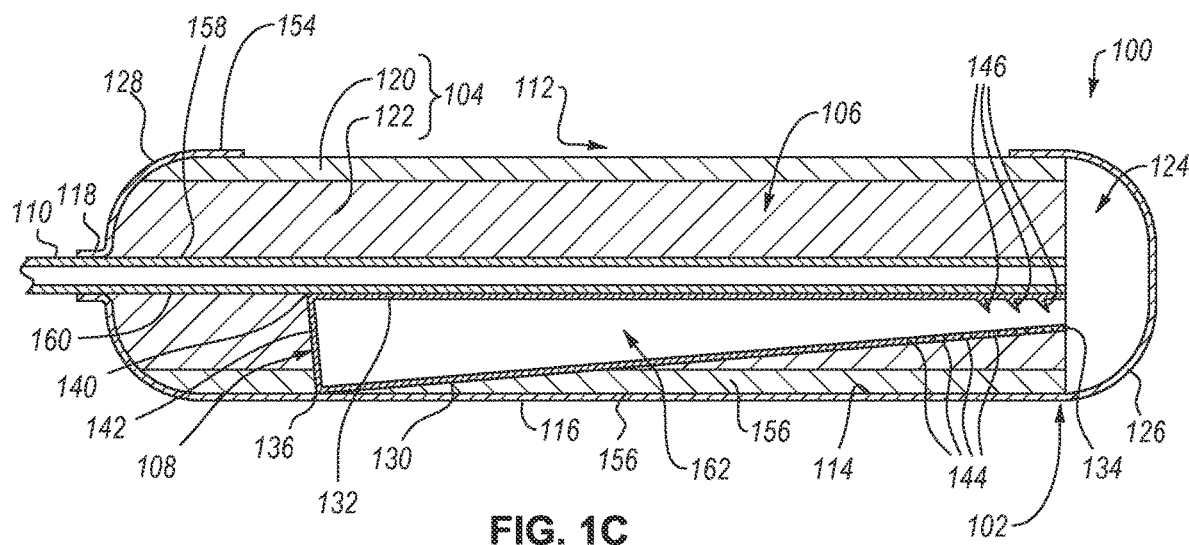
FIGS. 1C and 1D are cross-sectional schematics of the fluid collection assembly taken along planes 1C-1C and 1D-1D as shown in FIG. 1A, according to an embodiment.
Figure 1D:
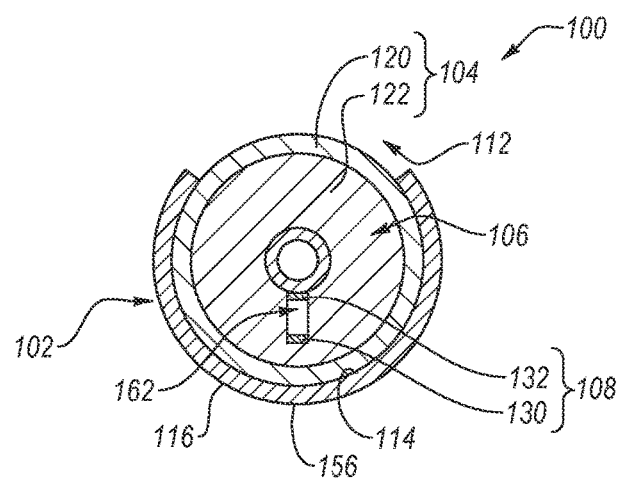

FIGS. 1A and 1B are isometric views of fluid collection assembly 100 exhibiting a first shape and a second shape, respectively, according to an embodiment. FIGS. 1C and 1D are cross-sectional schematics of the fluid collection assembly 100 taken along planes 1C-1C and 1D-1D as shown in FIG. 1A, according to an embodiment. The fluid collection assembly 100 is an example of a female fluid collection assembly that is configured to received one or more bodily fluids from a female patient. The fluid collection assembly 100 includes a fluid impermeable barrier 102, a porous material 104 disposed in a chamber 106 defined by the fluid impermeable barrier 102, an adjustable spine 108, and an optional conduit 110 disposed within the chamber 106.

The fluid impermeable barrier 102 at least partially defines a chamber 106 (e.g., interior region) and an opening 112. For example, at least one inner surface 114 of the fluid impermeable barrier 102 at least partially defines the chamber 106 within the fluid collection assembly 100. The fluid impermeable barrier 102 temporarily stores the bodily fluids in the chamber 106. The fluid impermeable barrier 102 may be formed of any suitable fluid impermeable material(s), such as a fluid impermeable polymer (e.g., silicone, polypropylene, polyethylene, polyethylene terephthalate, neoprene, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface 116 of the fluid impermeable barrier 102 may be formed from a soft and/or smooth material, thereby reducing chaffing.

In some examples, the fluid impermeable barrier 102 may be tubular (ignoring the opening), such as substantially cylindrical (as shown), oblong, prismatic, or flattened tubes. During use, the outer surface 116 of the fluid impermeable barrier 102 may contact the patient. The fluid impermeable barrier 102 may be sized and shaped to fit in the gluteal cleft between the legs of a female user.

The opening 112 provides an ingress route for fluids to enter the chamber 106. The opening 112 may be defined by the fluid impermeable barrier 102 such as by an inner edge of the fluid impermeable barrier 102. For example, the opening 112 is formed in and extends through the fluid impermeable barrier 102, from the outer surface 116 to the inner surface 114, thereby enabling bodily fluids to enter the chamber 106 from outside of the fluid collection assembly 100. The opening 112 may be an elongated hole in the fluid impermeable barrier 102. For example, the opening 112 may be defined as a cut-out in the fluid impermeable barrier 102. The opening 112 may be located and shaped to be positioned adjacent to a female urethra.

The fluid collection assembly 100 may be positioned proximate to the female urethral opening and the bodily fluids may enter the chamber 106 of the fluid collection assembly 100 via the opening 112. The fluid collection assembly 100 is configured to receive the bodily fluids into the chamber 106 via the opening 112. When in use, the opening 112 may have an elongated shape that extends from a first location below the urethral opening (e.g., at or near the anus or the vaginal opening) to a second location above the urethral opening (e.g., at or near the top of the vaginal opening or the pubic hair).

The opening 112 may have an elongated shape because the space between the legs of a female is relatively small when the legs of the female are closed, thereby only permitting the flow of the bodily fluids along a path that corresponds to the elongated shape of the opening 112 (e.g., longitudinally extending opening). The opening 112 in the fluid impermeable barrier 102 may exhibit a length that is measured along the longitudinal axis of the fluid collection assembly 100 that may be at least about 10% of the length of the fluid collection assembly 100, such as about 25% to about 50%, about 40% to about 60%, about 50% to about 75%, about 65% to about 85%, or about 75% to about 95% of the length of the fluid collection assembly 100.

The opening 112 in the fluid impermeable barrier 102 may exhibit a width that is measured transverse to the longitudinal axis of the fluid collection assembly 100 that may be at least about 10% of the circumference of the fluid collection assembly 100, such as about 25% to about 50%, about 40% to about 60%, about 50% to about 75%, about 65% to about 85%, or about 75% to about 100% of the circumference of the fluid collection assembly 100. The opening 112 may exhibit a width that is greater than 50% of the circumference of the fluid collection assembly 100 since the vacuum (e.g., suction) through the conduit 110 pulls the fluid through the porous material 104 and into the conduit 110. In some examples, the opening 112 may be vertically oriented (e.g., having a major axis parallel to the longitudinal axis of the fluid collection assembly 100). In some examples (not shown), the opening 112 may be horizontally oriented (e.g., having a major axis perpendicular to the longitudinal axis of the fluid collection assembly 100). In an example, the fluid impermeable barrier 102 may be configured to be attached to the patient, such as adhesively attached (e.g., with a hydrogel adhesive) to the patient. According to an example, a suitable adhesive is a hydrogel layer.

In some examples, the fluid impermeable barrier 102 may define an fluid outlet 118 sized to receive the conduit 110. The at least one conduit 110 may be disposed in the chamber 106 via the fluid outlet 118. The fluid outlet 118 may be sized and shaped to form an at least substantially fluid tight seal against the conduit 110 or the at least one tube thereby substantially preventing the bodily fluids from escaping the chamber 106.

The fluid impermeable barrier 102 may include markings thereon, such as one or more markings to aid a user in aligning the fluid collection assembly 100 on the patient. For example, a line on the fluid impermeable barrier 102 (e.g., opposite the opening 112) may allow a healthcare professional to align the opening 112 over the urethra of the patient. In examples, the markings may include one or more of alignment guide or an orientation indicator, such as a stripe or hashes. Such markings may be positioned to align the fluid collection assembly 100 to one or more anatomical features such as a pubic bone, etc.

The fluid collection assembly 100 includes porous material 104 disposed at least partially in the chamber 106. The porous material 104 may cover at least a portion (e.g., all) of the opening 112. The porous material 104 is exposed to the environment outside of the chamber 106 through the opening 112. In an embodiment, the porous material 104 may be configured to wick any bodily fluids away from the opening 112, thereby preventing the bodily fluids from escaping the chamber 106. The permeable properties referred to herein may be wicking, capillary action, diffusion, or other similar properties or processes, and are referred to herein as "permeable" and/or "wicking." Such "wicking" may not include absorption of the bodily fluids into the wicking material. Put another way, substantially no absorption of the bodily fluids into the material may take place after the material is exposed to the bodily fluids and removed from the bodily fluids for a time. While no absorption is desired, the term "substantially no absorption" may allow for nominal amounts of absorption of the bodily fluids into the wicking material (e.g., absorbency), such as less than about 30 wt % of the dry weight of the wicking material, less than about 20 wt %, less than about 15 wt %, less than about 10 wt %, less than about 7 wt %, less than about 5 wt %, less than about 3 wt %, less than about 2 wt %, less than about 1 wt %, or less than about 0.5 wt % of the dry weight of the wicking material. The wicking material may also wick the bodily fluids generally towards an interior of the chamber 106, as discussed in more detail below. In an embodiment, the porous material 104 may include at least one absorbent or adsorbent material.

The porous material 104 may include the fluid permeable membrane 120 disposed in the chamber 106. The fluid permeable membrane 120 may cover at least a portion (e.g., all) of the opening 112. The fluid permeable membrane 120 may be composed to wick the bodily fluids away from the opening 112, thereby preventing the bodily fluids from escaping the chamber 106.

In an embodiment, the fluid permeable membrane 120 may include any material that may wick the bodily fluids. For example, the fluid permeable membrane 120 may include fabric, such as a gauze (e.g., a silk, linen, or cotton gauze), another soft fabric, or another smooth fabric. Forming the fluid permeable membrane 120 from gauze, soft fabric, and/or smooth fabric may reduce chaffing caused by the fluid collection assembly 100.

The fluid collection assembly 100 may include the fluid permeable support 122 disposed in the chamber 106. The fluid permeable support 122 is configured to support the fluid permeable membrane 120 since the fluid permeable membrane 120 may be formed from a relatively foldable, flimsy, or otherwise easily deformable material. For example, the fluid permeable support 122 may be positioned such that the fluid permeable membrane 120 is disposed between the fluid permeable support 122 and the fluid impermeable barrier 102. As such, the fluid permeable support 122 may support and maintain the position of the fluid permeable membrane 120. The fluid permeable support 122 may include any material that may wick the bodily fluids, such as any of the fluid permeable membrane materials disclosed herein above. For example, the fluid permeable membrane material(s) may be utilized in a more dense or rigid form than in the fluid permeable membrane 120 when used as the fluid permeable support 122. The fluid permeable support 122 may be formed from any fluid permeable material that is less deformable than the fluid permeable membrane 120. For example, the fluid permeable support 122 may include a porous polymer (e.g., spun nylon fibers, polyester, polyurethane, polyethylene, polypropylene, etc.) structure or an open cell foam, such as spun nylon fibers. In some examples, the fluid permeable support 122 may be formed from a natural material, such as cotton, wool, silk, or combinations thereof. In such examples, the material may have a coating to prevent or limit absorption of fluid into the material, such as a water repellent coating. In some examples, the fluid permeable support 122 may be formed from fabric, felt, gauze, or combinations thereof.

In some examples, the fluid permeable membrane 120 may be optional. For example, the porous material 104 may include only the fluid permeable support 122. In some examples, the fluid permeable support 122 may be optionally omitted from the fluid collection assembly 100. For example, the porous material 104 may only include the fluid permeable membrane 120.

The fluid permeable support 122 may have a greater ability to wick the bodily fluids than the fluid permeable membrane 120, such as to move the bodily fluids inwardly from the outer surface 116 of the fluid collection assembly 100. In some examples, the porous ability of the fluid permeable support 122 and the fluid permeable membrane 120 may be substantially the same.

The fluid permeable membrane 120 and the fluid permeable support 122 may at least substantially completely fill the portions of the chamber 106 that are not occupied by the conduit 110 and, optionally, the adjustable spine 108. In some examples, the fluid permeable membrane 120 and the fluid permeable support 122 may not substantially completely fill the portions of the chamber 106 that are not occupied by the conduit 110 and, optionally, the adjustable spine 108. In such an example, the fluid collection assembly 100 includes the reservoir 124 (FIG. 1C) disposed in the chamber 106.

The reservoir 124 is a substantially unoccupied portion of the chamber 106. The reservoir 124 may be defined between the fluid impermeable barrier 102 and one or both of the fluid permeable membrane 120 and fluid permeable support 122. The bodily fluids that are in the chamber 106 may flow through the fluid permeable membrane 120 and/or fluid permeable support 122 to the reservoir 124. The reservoir 124 may retain of the bodily fluids therein.

The bodily fluids that are in the chamber 106 may flow through the fluid permeable membrane 120 and/or fluid permeable support 122 to the reservoir 124. The fluid impermeable barrier 102 may retain the bodily fluids in the reservoir 124. While depicted in the distal end region 126, the reservoir 124 may be located in any portion of the chamber 106 such as the proximal end region 128. The reservoir 124 may be located in a portion of the chamber 106 that is designed to be located in a gravimetrically low point of the fluid collection assembly when the fluid collection assembly is worn.

In some examples (not shown), the fluid collection assembly 100 may include multiple reservoirs, such as a first reservoir that is located at the portion of the chamber 106 closest to the inlet of the conduit 110 (e.g., distal end region 126) and a second reservoir that is located at the portion of the of the chamber 106 that is at or near the proximal end region 128. In another example, the fluid permeable support 122 is spaced from at least a portion of the conduit 110, and the reservoir 124 may be the space between the fluid permeable support 122 and the conduit 110.

The conduit 110 may be at least partially disposed in the chamber 106. The conduit 110 may be used to remove the bodily fluids from the chamber 106. The conduit 110 (e.g., a tube) includes an inlet of the conduit 110 and an outlet of the conduit 110 positioned downstream from the inlet of the conduit 110. The outlet of the conduit 110 may be operably coupled to a suction source, such as a vacuum pump for withdrawing fluid form the chamber through the conduit 110. For example, the conduit 110 may extend into the fluid impermeable barrier 102 from the proximal end region 128 and may extend to the distal end region 126 to a point proximate to the reservoir 124 therein such that the inlet of the conduit 110 is in fluid communication with the reservoir 124. The conduit 110 fluidly couples the chamber 106 with the fluid storage container (not shown) or the vacuum source (not shown).

The conduit 110 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 110 may include silicon or latex. In some examples, the conduit 110 may include one or more portions that are resilient, such as to by having one or more of a diameter or wall thickness that allows the conduit to be flexible.

The conduit 110 may extend through a bore in the fluid permeable membrane 120 and/or fluid permeable support 122, such as into the reservoir 124. For example, the inlet of the conduit 110 may be extend into or be positioned in the reservoir 124. In the illustrated embodiment, the conduit 110 is at least partially disposed in the reservoir 124. In some examples (not shown), the conduit 110 may enter the chamber 106 in the distal end region and the inlet of the conduit 110 of the conduit 110 may be disposed in the distal end region (e.g., in the reservoir 124). The bodily fluids collected in the fluid collection assembly 100 may be removed from the chamber 106 via the conduit 110.

In some examples, the inlet of the conduit 110 may not extend into the reservoir 124. In such examples, the inlet of the conduit 110 may be disposed within the porous material 104 (fluid permeable membrane 120 and/or fluid permeable support 122) or at a terminal end thereof. For example, an end of the conduit 110 may be coextensive with or recessed within the fluid permeable membrane 120 and/or fluid permeable support 122.

Locating the inlet of the conduit 110 at or near a location expected to be the gravimetrically low point of the chamber 106 when worn by a patient enables the conduit 110 to receive more of the bodily fluids than if inlet of the conduit 110 was located elsewhere and reduce the likelihood of pooling (e.g., pooling of the bodily fluids may cause microbe growth and foul odors). For instance, the bodily fluids in the fluid permeable membrane 120 and the fluid permeable support 122 may flow in any direction due to capillary forces. However, the bodily fluids may exhibit a preference to flow in the direction of gravity, especially when at least a portion of the fluid permeable membrane 120 and/or the fluid permeable support 122 is saturated with the bodily fluids. Accordingly, one or more of the inlet of the conduit 110 or the reservoir 124 may be located in the fluid collection assembly 100 in a position expected to be the gravimetrically low point in the fluid collection assembly 100 when worn by a patient, such as the distal end region 127.

In an example, the conduit 110 is configured to be at least insertable into the chamber 106. In such an example, the conduit 110 may include one or more markers (not shown) on an exterior thereof that are located to facilitate insertion of the conduit 110 into the chamber 106. For example, the conduit 110 may include one or more markings thereon that are configured to prevent over or under insertion of the conduit 110, such as when the conduit 110 defines an inlet of the conduit 110 that is configured to be disposed in or adjacent to the reservoir 124. In another example, the conduit 110 may include one or more markings thereon that are configured to facilitate correct rotation of the conduit 110 relative to the chamber 106. The one or more markings may include a line, a dot, a sticker, or any other suitable marking.

As described in more detail below, the conduit 110 is configured to be coupled to, and at least partially extend between, one or more of the fluid storage container (not shown) and the vacuum source (not shown). In an example, the conduit 110 is configured to be directly connected to the vacuum source (not shown). In such an example, the conduit 110 may extend from the fluid impermeable barrier 102 by at least one foot, at least two feet, at least three feet, or at least six feet. In another example, the conduit 110 is configured to be indirectly connected to at least one of the fluid storage container (not shown) and the vacuum source (not shown). In some examples, the conduit is secured to a patient's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet of the conduit 110 and the outlet of the conduit 110 are configured to fluidly couple (e.g., directly or indirectly) the vacuum source (not shown) to the chamber 106 (e.g., the reservoir 124). As the vacuum source (FIG. 14) applies a vacuum/suction in the conduit 110, the bodily fluids in the chamber 106 (e.g., at the distal end region such as in the reservoir 124) may be drawn into the inlet of the conduit 110 and out of the fluid collection assembly 100 via the conduit 110. In some examples, the conduit may be frosted or opaque (e.g., black) to obscure visibility of the bodily fluids therein.

Figure 1E:
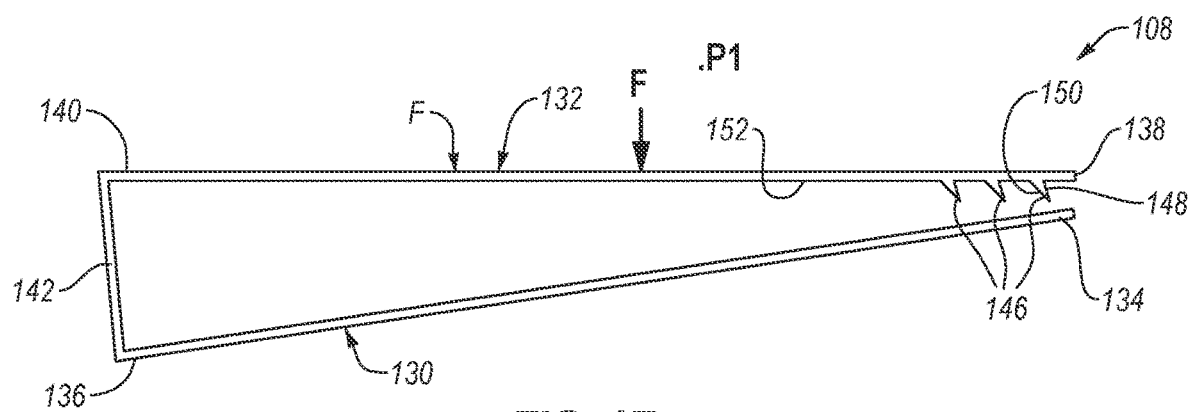
FIGS. 1E and 1F are side views of the adjustable spine in a different states, respectively, according to an embodiment.
Figure 1F:
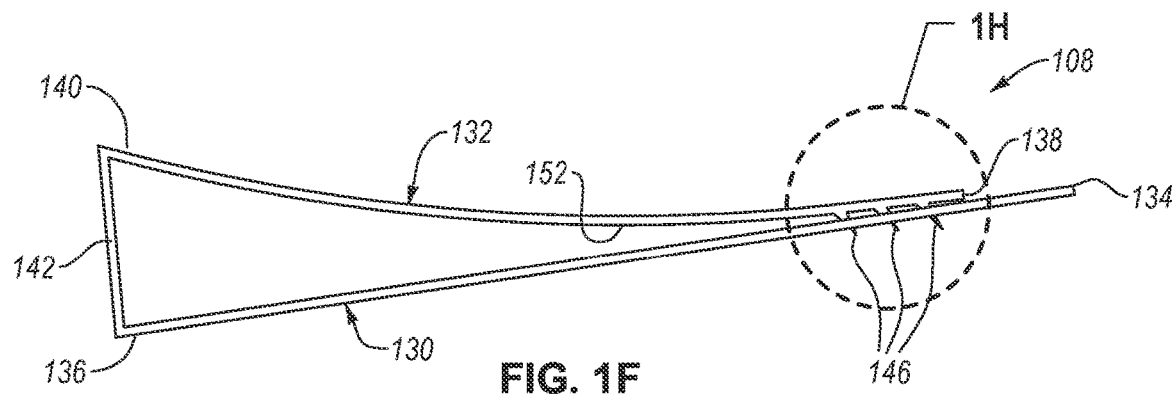
Figure 1G:
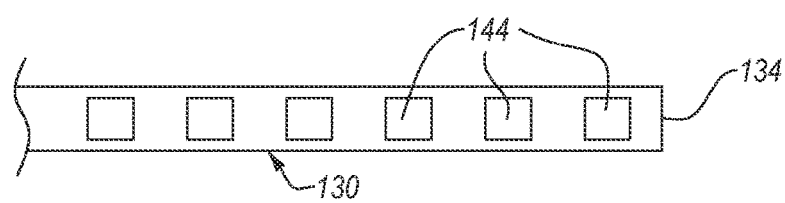
FIG. 1G is a top plan view of a portion of the first strip, according to an embodiment.
Figure 1H:
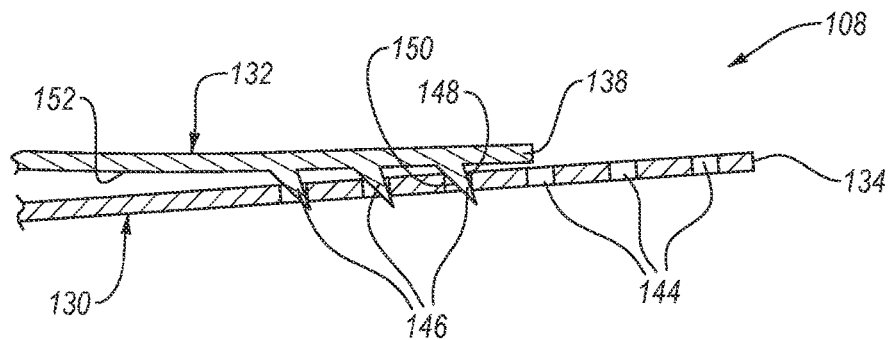
FIG. 1H is an enlarged view of the portion of the adjustable spine within the circle 1H shown in FIG. 1F, according to an embodiment.

The fluid collection assembly 100 includes at least one adjustable spine 108. The adjustable spine 108 is illustrated in more detail in FIGS. 1E-1H. FIGS. 1E and 1F are side views of the adjustable spine 108 in a different states, respectively, according to an embodiment. FIG. 1G is a top plan view of a portion of the first strip 130, according to an embodiment. FIG. 1H is an enlarged view of the portion of the adjustable spine 108 within the circle 1H shown in FIG. 1F, according to an embodiment. The adjustable spine 108 is configured to selectively change the shape of the fluid collection assembly 100, for example, such that the fluid collection assembly 100 better conforms to the shape of the region about the urethral opening. For example, the adjustable spine 108 may exhibit a first, relaxed state (FIG. 1E) and a second, stressed state (FIG. 1F). The fluid collection assembly 100 may exhibit a first shape (FIG. 1A) when the adjustable spine 108 exhibits the first state and a second shape (FIG. 1B) that is different than the first shape when the adjustable spine 108 exhibits the second state thereof. As such, the shape of the fluid collection assembly 100 may be at least partially controlled by the adjustable spine 108.

The adjustable spine 108 includes a first strip 130 and a second strip 132. At least the second strip 132 is configured to change a configuration thereof when a force is applied to the adjustable spine 108. For example, the second strip 132 may exhibit a relaxed configuration (FIG. 1E) and a stressed configuration (FIG. 1F). The adjustable spine 108 may exhibit a first state and a second state when the second strip 132 exhibits the relaxed configuration and the stressed configuration, respectively. In an embodiment, the adjustable spine 108 and the second strip 132 are provided in the first state and relaxed configuration thereof, respectively. In an embodiment, the adjustable spine 108 and the second strip 132 are provide in the second state and stressed configuration thereof, respectively.

The shape of the second strip 132 may change when the second strip 132 switches between the relaxed configuration to the stressed configuration. In an example, as shown, the second strip 132 may switch from a generally straight shape to a curved (e.g., concavely curved) shape when switching from the relaxed configuration to the stressed configuration. In an example, the second strip 132 may switch from a curved shape to a generally straight shape when switching from the relaxed configuration to the stressed configuration. In an example, the second strip 132 may switch from a first curved shape to a second curved shape that is different than the first curved shape when switching the second strip 132 from the relaxed to the stressed configuration. The second curved shape may be a more curved shape (e.g., exhibits an average radius of curvature that is less than) the first curved shape or the second curved shape may exhibit a different curvature (e.g., the first curved shape is a concave or convex curve and the second curved shape is the other of a concave or convex curve). As used herein, the concavity or convexity of the second strip 132 and any of the other second strips disclosed herein is relative to a point P1 above the second strip 132 (e.g., a location that is closer to the second strip 132 than the first strip 130, generally in the same plane as at least three of the terminal ends of the first and second strips 130, 132, and not between the first and second strips 130, 132). In other words, the second strip 132 is concavely curved when the second strip 132 bends towards the first strip 130 and convexly curved when the second strip 132 bends away from the first strip 130.

The first and second strips 130, 132 may be longitudinally extending pieces of material. For example, the first strip 130 includes a first terminal end 134 and a second terminal end 136 opposite the first terminal end 134. The first strip 130 extends longitudinally between the first and second terminal ends 134, 136 thereof. Similarly, the second strip 132 includes a third terminal end 138 and a fourth terminal end 140 opposite the third terminal end 138. The second strip 132 extends longitudinally between the third and fourth terminal ends 138, 140. The first and second strips 130, 132 may be positioned such that the first terminal end 134 of the first strip 130 and the third terminal end 138 of the second strip 132 are positioned proximate to each other and/or the second terminal end 136 of the first strip 130 and the fourth terminal end 140 of the second strip 132 are positioned proximate to each other. Positioning the first and third terminal ends 134, 138 proximate to each other may allow may allow the steps of the adjustable spine 108 to become engaged, as discussed in more detail below. Positioning the second and fourth terminal ends 136, 140 proximate to each other allows the first and second strips 130, 132 to be attached together using the crossbeam 142.

In an embodiment, as shown, the first strip 130 substantially does not bend when the force F is applied to the adjustable spine 108 or after the steps of the adjustable spine 108 are engaged. In such an embodiment, the first strip 130 may exhibit a rigidity that is greater than the second strip 132 which may cause the second strip 132 to bend while the first strip 130 remains substantially unchanged (e.g., substantially straight). The first strip 130 may exhibit a rigidity that is significantly greater (e.g., at least about 2 times greater, at least about 5 times greater, or at least about 10 times greater) than the second strip 132 because the first strip 130 is formed from a material exhibiting a larger Young's modulus (i.e., modulus of elasticity) that is greater than the second strip 132 or the first strip 130 exhibits a thickness and/or cross-sectional area that is greater than the second strip 132. Configuring the first strip 130 to remain substantially straight may minimize the force F that needs to be applied to the adjustable spine 108 since the force F substantially only needs to deform the second strip 132 and not both the first and second strips 130, 132. In an embodiment, the first strip 130 is configured to bend along with the second strip 132 when the force F is applied to the adjustable spine 108. In such an embodiment, the first strip 130 may exhibit a rigidity that is equal to or only slightly greater (e.g., at most about 5 times greater, at most about 2 times greater, or at most about 1.5 times greater) than the rigidity of the second strip 132. Allowing the first strip 130 to bend when the force F is applied to the adjustable spine 108 may facilitate manufacturing of the adjustable spine 108 (e.g., the adjustable spine 108 may be formed from the same material, exhibits single piece construction, and/or exhibit the same thickness) since the manufacturing of the first strip 130 does not need to significantly more rigid than the second strip 132.

The adjustable spine 108 may be formed from any suitable material. For example, the adjustable spine 108 may be formed from steel, copper, aluminum, another metal, one or more polymers (e.g., polyvinyl chloride, polyethylene, polypropylene, etc.), a composite, or combinations thereof. In an embodiment, the adjustable spine 108 is formed from the same material and exhibits single piece construction. In an embodiment, the adjustable spine 108 is formed from a plurality of different materials and/or does not exhibit single piece construction. For example, the first strip 130 and/or the crossbeam 142 may be formed from a first material and the second strip 132 may be formed from a second material. The first material may exhibit a Young's modulus (i.e., modulus of elasticity) that is greater than the Young's modulus than the second material. The smaller Young's modulus of the second material may allow the second strip 132 to bend more than the first strip 130 and the crossbeam 142.

In an embodiment, as illustrated, the adjustable spine 108 includes a crossbeam 142 connected to and extending between the first and second strips 130, 132. For example, the crossbeam 142 may be attached to a portion of the first strip 130 at or near the second terminal end 136 thereof and attached to a portion of the second strip 132 at or near the fourth terminal end 140 thereof. The crossbeam 142 allows at least a portion of the first strip 130 to be spaced from at least a portion of the second strip 132. The crossbeam 142 may allow a force applied to the adjustable spine 108 to change the second strip 132 to a more stressed configuration (e.g., from the relaxed configuration to a stressed configuration) instead of merely moving the first and second strips 130, 132 closer together. In some embodiments, the crossbeam 142 is formed from a relatively rigid material such that the crossbeam 142 substantially does not change a shape thereof (e.g., bend) when the configuration of the second strip 132 changes.

At least one of the first strip 130 or the second strip 132 may include one or more steps. The steps may include any feature that is configured to become engaged. As used herein, the steps become engaged when the steps come in contact with the strip that does not include the particular step in a manner than inhibits the second strip 132 from switching to a more relaxed state, such as from the stressed configuration to the relaxed configuration. For example, when the first strip 130 includes the steps, the steps of the first strip 130 are configured to come in contact with the second strip 132 (e.g., come in contact with steps of the second strip 132) in a manner that inhibits the second strip 132 from switching to a more relaxed state. When the second strip 132 includes the steps, the steps of the second strip 132 are configured to come in contact with the first strip 130 (e.g., come in contact with the steps of the first strip 130) in a manner that inhibits the second strip 132 from switching to a more relaxed state. It is noted that the steps merely inhibit (i.e., do not prevent) the second strip 132 from switching to a more relaxed configuration since, as will be discussed in more detail below, the steps may become disengaged in certain embodiments. It is also noted that the steps may only become engaged after the second strip 132 becomes stressed.

In an example, the steps may include at least one of one or more protrusions (e.g., teeth) that extend from the strip, define one or more recesses therebetween, include one or more magnets, include one or more magnetically attracted materials (e.g., a metal), include a pressure adhesive, or any other feature that may engage the other of the first or second strip 132, 132. The steps may be integrally formed with or distinct from and attached to the first strip 130 and/or the second strip 132.

Figure 6A:
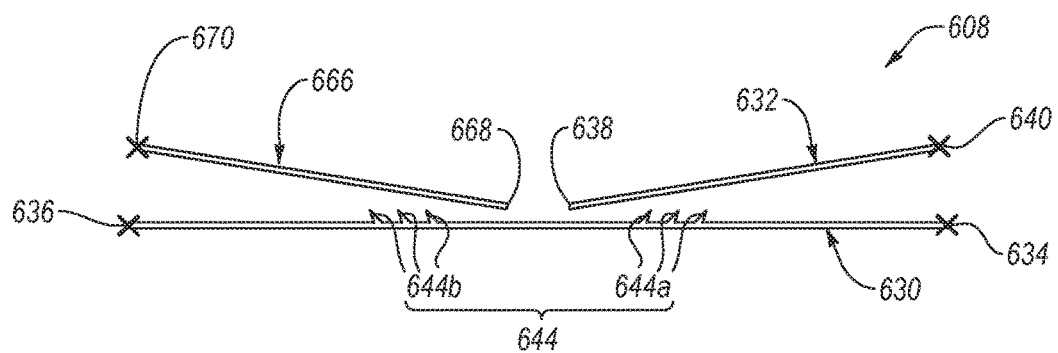
FIG. 6A is a side view of an adjustable spine, according to an embodiment.
Figure 6B:
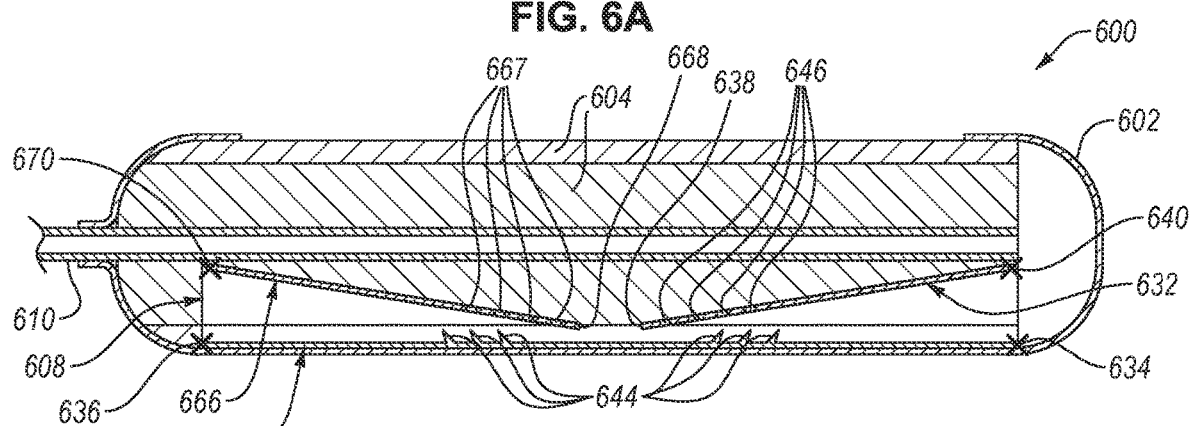
FIG. 6B is a cross-sectional schematic of a fluid collection assembly that includes the adjustable spine shown in FIG. 6A, according to an embodiment.

In an embodiment, only one of the first or second strip 132, 132 includes one or more steps (as shown in FIGS. 6A and 6B). In an embodiment, as shown, both of the first and second strips 130, 132 includes steps. In such an example, the first strip 130 may include one or more first steps 144 (shown in FIGS. 1G and 1H) and the second strip 132 may include one or more second steps 146. The first and second steps 144, 146 may be configured to engage with each other. In an example, the first steps 144 may define one or more recesses therebetween (e.g., formed in the first strip 130, as shown in FIG. 1H) and the second steps 146 may include one or more protrusion extending outwardly from the second strip 132. The first steps 144 and the second steps 146 may be configured such that at least one of the protrusions of the second steps 146 are disposed in at least one of the recesses of the first steps 144 when the first and second steps 144, 146 are engaged (e.g., when the second strip 132 is in the stressed configuration).

Figure 3A:
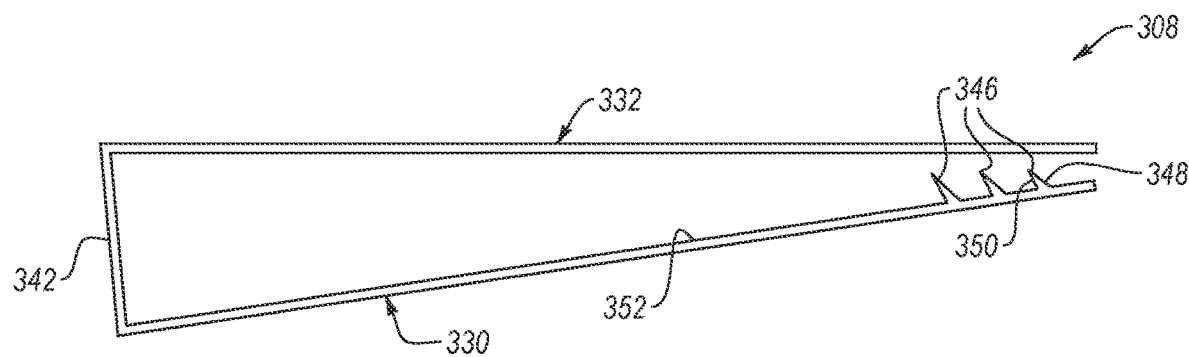
FIGS. 3A and 3B are side views of an adjustable spine that includes one or more protrusions formed on the first strip thereof and one or more recesses formed in the second strip thereof, according to an embodiment.
Figure 3B:
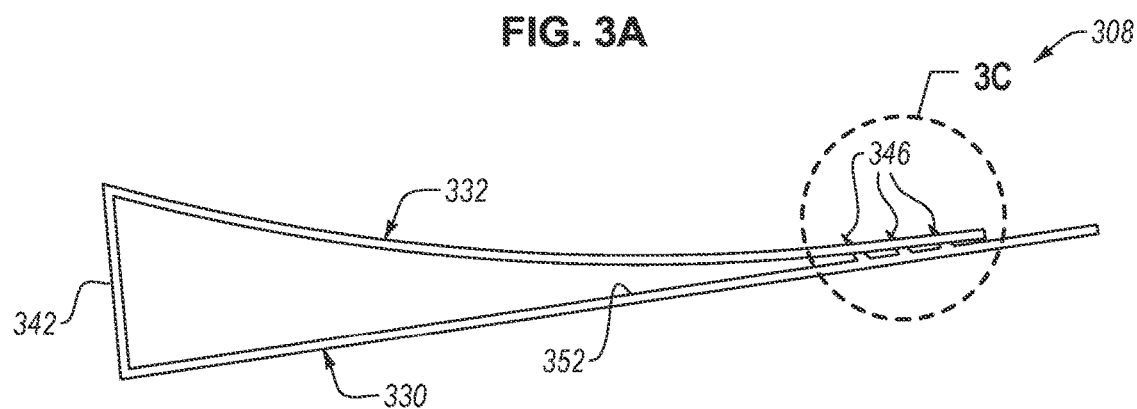
Figure 3C:
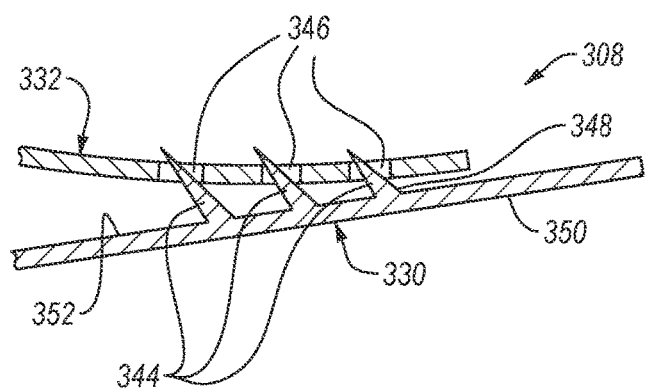
FIG. 3C is an enlarged cross-sectional schematic of the portion of the adjustable spine shown in the circle 3C of FIG. 3B, according to an embodiment.

When the steps includes one or more protrusions, the protrusions may include a first surface 148 and a second surface 150 extending from of near at least one main surface 152. As used herein, the first surface 148 is closer to the terminal end of the strip than the second surface 150. The main surface 152 is generally parallel to a longitudinal axis of the strip. The angles of the first and second surfaces 148, 150 relative to a main surface 152 may be selected to allow the protrusions to become engaged. In an example, when the one or more protrusions are formed on the second strip 132 (as shown in FIGS. 1C, 1E, 1F, and 1H), the angle formed between the second and main surfaces 150, 152 is an obtuse angle and the angle formed between the first and main surfaces 148, 152 is an acute angle, a perpendicular angle, or an obtuse angle that is less than the obtuse angle between the second and main surfaces 150, 152. However, preferably, the angle between the first and main surfaces 148, 152 is an acute or substantially perpendicular angle. The angle between the second and main surfaces 150, 152 prevents the protrusions from engaging the first strip 130 as the second strip 132 is further stressed while the angle between the first and main surfaces 148, 152 may cause the protrusion to engage the first strip 130 when the second strip 132 tries to relax. In an example, when the one or more protrusions are formed on the first strip 130 (as shown in FIGS. 3A-3C), the angle formed between the first and main surfaces 148, 152 is an obtuse angle and the angle formed between the second and main surfaces 150, 152 is preferably one of an acute angle, a perpendicular angle, or an obtuse angle that is less than the obtuse angle between the first surface 148 and the main surface 152. However, preferably, the angle between the second and main surfaces 150, 152 is an acute or substantially perpendicular angle. The angle between the first and main surfaces 148, 152 prevents the protrusions from engaging the second strip 132 as the second strip 132 is further stressed (e.g., more bent) while the angle between the second and main surfaces 150, 152 may cause the protrusion to engage the second strip 132 when the second strip 132 tries to relax (e.g., straighten).

The operation of the adjustable spine 108 will be discussed with regards to FIGS. 1E to 1H. Referring to FIG. 1E, the adjustable spine 108 exhibits the first state. The adjustable spine 108 may be provided in the first state such that the first state is in the initial state thereof. The adjustable spine 108 may exhibit the first state when the second strip 132 exhibits the relaxed configuration thereof. The second strip 132 may be in the relaxed state when the steps of the adjustable spine 108 are not engaged. The fluid collection assembly 100 may exhibit the first shape illustrated in FIG. 1A when the adjustable spine 108 is in the first state.

As shown in FIG. 1E, a force F may be applied to the adjustable spine 108 which stresses the adjustable spine 108. In particular, the force F is applied to at least the second strip 132. The crossbeam 142 substantially maintains the position of the second and fourth terminal ends 136, 140 of the first and second strips 130, 132 when the force F is applied to the adjustable spine 108. As such, as shown in FIG. 1F, the force F causes the second strip 132 to bend instead of merely moving the second strip 132 closer to the first strip 130. In other words, the force F changes the second strip 132 from the relaxed configuration to the stressed configuration. As illustrated, the force F causes the second strip 132 to form a concave curvature.

Referring to FIG. 1H, as the second strip 132 bends, the steps of the adjustable spine 108 engages the strip that does not include the particular step. As previously discussed, as illustrated, the first strip 130 includes one or more first steps 144 that define recesses therebetween and the second strip 132 includes one or more second steps 146 that are protrusions that extend therefrom. As the second strip 132 is stressed, the protrusions of the second strip 132 engage (e.g., are at least partially positioned through) the recesses formed in the first strip 130. For example, when the first and third terminal ends 134, 138 are adjacent to each other, stressing the second strip 132 moves the third terminal end 138 closer to from the second terminal end 136. The obtuse angle between the second and main surfaces 150, 152 of the protrusions allows the protrusions to easily move from one recess to the next recess as the second strip 132 is further stressed. Meanwhile, the smaller angle between the first and main surfaces 148, 152 of the protrusions inhibits the protrusions from moving from one recess to the next recess when the second strip 132 relaxes.

FIGS. 1F and 1H illustrate the second strip 132 in a first stressed configuration. However, the second strip 132 may exhibit one or more stressed configurations other than the first stressed configuration shown in FIGS. 1F and 1H. For example, the second strip 132 may exhibit one or more second stressed configurations or one or more third configurations. As used herein, the one or more second stressed configurations and the one or more third configurations includes configurations where the second strip 132 is stressed less and more, respectively than when the second strip 132 is in the first stressed configuration. When the second strip 132 exhibits the one or more second configurations and the one or more third configurations, the adjustable spine 108 may exhibit a third state and a fourth state, respectively. When the adjustable spine 108 exhibits the third and fourth states, the fluid collection assembly 100 may exhibit a third and fourth shape, respectively, wherein each of the first, second, third, and fourth shapes of the fluid collection assembly 100 are different. For example, when the fluid collection assembly 100 is substantially straight when exhibiting the first shape and curved when exhibiting the second shape, the third shape of the fluid collection assembly 100 may be less curved (e.g., exhibit an average radius of curvature that is less than) than the second shape and more curved (e.g., exhibit an average radius of curvature that is greater than) the second shape.

The force F applied to the second strip 132 may dictate whether the second strip 132 exhibits the first, second, or third stressed configurations. In an example, a force F that disposes the second strip 132 in the second stressed configuration may be less (e.g., in time and/or magnitude) than a force F that disposes the second strip 132 in the second stressed configuration. In an example, the force F that disposes the second strip 132 in the second stressed configuration may be less (e.g., in time and/or magnitude) than a force F that disposes the second strip 132 in the third stressed configuration.

The steps of the adjustable spine 108 are configured to inhibit the second strip 132 from at least partially relaxing after the second strip 132 is in the first, second, and third stressed configurations. For example, the steps of the adjustable spine 108 may be configured to inhibit the second strip 132 from switching from the first stressed configuration to the second stressed configuration or the relaxed configuration; the second stressed configuration to the relaxed configuration; or the third stressed configuration to the first stressed configuration, the second stressed configuration, or the relaxed configuration.

It is noted that a disengagement force may be applied to the adjustable spine 108 such that the steps thereof become disengaged and the second strip 132 is allowed to at least partially relax. In an embodiment, the disengagement required to disengage the first and second steps 144, 146 may be relatively difficult since the protrusions are disposed in the recesses and the adjustable spine 108 is disposed in the chamber 106 (e.g., cannot be seen and/or directly manipulated). For example, referring to FIG. 1H, the disengagement force would need be applied to the adjustable spine 108 (e.g., to the protrusions of the second steps 146) such that the protrusions of the second steps 146 are not disposed in the recesses defined by the first steps 144. Such a disengagement force may need to be applied to selective portions of the adjustable spine 108 and/or to multiple portions of the adjustable spine 108.

As shown in FIGS. 1E and 1F, the second strip 132 may exhibit a more concave curvature when in the stressed configuration than when in the relaxed configuration. For example, the second strip 132 may be substantially straight when the second strip 132 exhibits the relaxed configuration and a concave curvature when the second strip 132 is in the stressed configuration. The second strip 132 at least partially controls the shape of the fluid collection assembly 100. As such, the second strip 132 is attached to a surface of the fluid collection assembly 100 that is more convex than when the fluid collection assembly 100 exhibits the second shape than when the fluid collection exhibits the first shape. For example, switching the second strip 132 from the relaxed configuration to the stressed configuration causes the surface of the component to which the second strip 132 is attached to exhibit a corresponding shape. In the illustrated embodiment, switching the second strip 132 from the relaxed configuration to the stressed configuration causes the surface to which the second strip 132 is attached to change from a generally straight shape to a convex shape. Changing the shape of the surface to which the second strip 132 is attached changes the shape of that component that include the surface which, in turn, changes the shape of the rest of the fluid collection assembly 100 to generally match the shape change of the component. It is noted that the shape change in the second strip 132 and in the fluid collection assembly 100 as a whole may be slightly different (i.e., "generally match") due to the flexibility of the fluid collection assembly 100 which causes the portions of the fluid collection assembly 100 to compress or stretch instead changing the shape thereof in the same manner as the second strip 132. The surface of the fluid collection assembly 100 that the second strip 132 is attached to may depend on the which shape of the fluid collection assembly 100 assumes when the fluid collection assembly 100 exhibits the first shape and what component (e.g., fluid impermeable barrier 102, porous material 104, or conduit 110) the second strip 132 is attached to.

Referring to FIGS. 1A-1D, the fluid collection assembly 100 exhibits a substantially straight first shape and a concavely curved second shape relative to the opening 112. The fluid impermeable barrier 102 includes a front side 154 that at least partially defines the opening 112 and a back side 156 opposite the front side 154. The front and back sides 154, 156 may be substantially straight when the fluid collection assembly 100 exhibits the first shape. As shown in FIG. 1B, the front side 154 may be concavely curved and the backs side 156 may be convexly curved relative to a point P2 above (e.g., outside of the chamber 106) the opening 112 when the fluid collection assembly 100 exhibits the second shape. Due to the concavity of the second strip 132, the second strip 132 may be attached to any surface of a component of the fluid collection assembly 100 that is concave relative to the point P2 when the fluid collection assembly 100 exhibits the second shape. For example, as illustrated in FIGS. 1C and 1D, the second strip 132 is attached to the conduit 110. The conduit 110 includes a conduit top side 158 and a conduit bottom side 160. The conduit top side 158 is closer to the top side 154 of the fluid impermeable barrier 102 than the conduit bottom side 160 and the conduit bottom side 160 is closer to the back side 156 of the fluid impermeable barrier 102 than the conduit top side 158. When the fluid collection assembly 100 exhibits the second shape, the conduit top side 158 exhibits a concave curve and the conduit bottom side 160 exhibits a convex curve. As such, the second strip 132 may attached to the conduit bottom side 160. Changing the second strip 132 from the relaxed configuration to the stressed configuration causes the conduit bottom side 160 to change from being substantially straight to a convex shape that corresponds to the concave shape of the second strip 132. Changing the conduit bottom surface 160 to the convex shape causes the conduit 110, as a whole, to generally exhibit a shape that generally matches to the convex shape of the conduit bottom surface 160. Changing the shape of the conduit 110 causes the porous material 104 to also exhibit a shape change that generally matches to the shape change of the conduit 110. Similarly, changing the shape of the porous material 104 causes the fluid impermeable barrier 102 to also exhibit a shape change that generally matches to the shape change of the conduit 110.

Figure 17A:
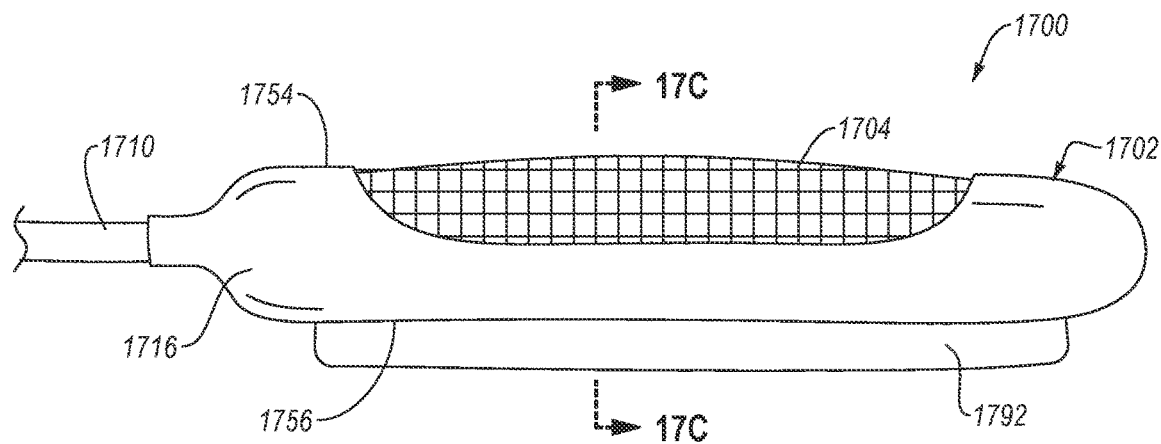
FIGS. 17A and 17B are isometric views of a fluid collection assembly with a cap and with the cap removed, respectively, according to an embodiment.
Figure 17B:
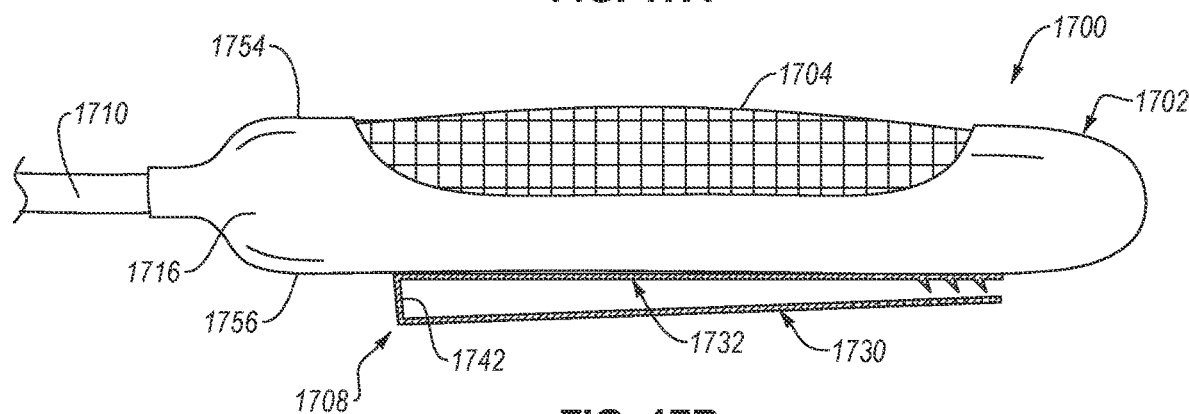
Figure 17C:
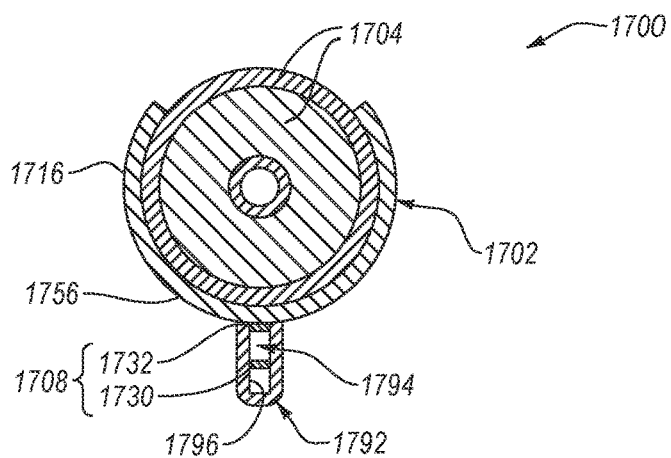
FIG. 17C is a cross-sectional schematic of the fluid collection assembly taken along plane 17C-17C as shown in FIG. 17A, according to an embodiment.

The second strip 132 may be attached to other components of the fluid collection assembly 100 other than the conduit 110. In an embodiment, the second strip 132 may be attached to the inner surface 114 of the front side 154 even though the second strip 132 may partially block the opening 112. In an embodiment, the second strip 132 may be attached to the porous material 104, such as the fluid permeable membrane 120 or the fluid permeable support 122. When the second strip 132 is attached to the fluid permeable membrane 120, the second strip 132 may be attached to a surface of the fluid permeable membrane 120 that faces the fluid permeable support 122 and is proximate to the front side 154 or to a surface of the fluid permeable membrane 120 that faces the fluid impermeable barrier 102 and is proximate to the back side 156. When the second strip 132 is attached to the fluid permeable support 122, the second strip 132 may be attached to a surface of the fluid permeable support 122 that faces the conduit 110 and is proximate to the front conduit side 158 or a surface of the fluid permeable support 122 that faces the fluid permeable membrane 120 that is proximate to the back side 156. In an embodiment, the second strip 132 may be attached to the outer surface 116 of the back side 156 of the fluid impermeable barrier 102 (as shown in FIGS. 17A-17C).

In an embodiment, at least one of at least a portion of the first strip 130 or at least a portion of the crossbeam 142 are attached to a component of the fluid collection assembly 100. In an embodiment, at least one of the first strip 130 or the crossbeam 142 is not attached to a component of the fluid collection assembly 100.

When the adjustable spine 108 is positioned within the chamber 106, the porous material 104 may define a gap 162 that is configured to have the adjustable spine 108 disposed therein. The gap 162 may be substantially unoccupied space such that the porous material 104 is not positioned between the first and second strips 130, 132. The substantially unoccupied space may facilitate insertion of the adjustable spine 108 into the gap 162 and may prevent the porous material 104 from obstructing the shape changes of the second strip 132. However, it is noted that the porous material 104 may be positioned between the first and second strips 130, 132 since the porosity and flexibility of the porous material 104 allows the porous material 104 to be easily compressible such that, except for requiring an increase in the magnitude of the force F, the porous material 104 does not impede the shape change of the second strip 132.

As previously discussed, the adjustable spine 108 changes the shape of the fluid collection assembly 100 from a first shape to a second shape. In an embodiment, as illustrated in FIGS. 1A and 1B, the first shape of the fluid collection assembly 100 is a substantially straight shape and the second shape of the fluid collection assembly 100 is a concave curve relative to point P2. However, the fluid collection assembly 100 may exhibit other shapes than the shape illustrated in FIGS. 1A and 1B. In an example, the first shape may be a substantially straight shape and the second shape may be a convex curve relative to point P2. In an example, the first shape is a curved shape (e.g., concave or convex curve relative to point P2) and the second shape is a substantially straight shape. In an example, the first shape is a first curved shape and the second shape is a second curved shape. The first curved shape is different than the second curved shape. For instance, the first curved shape may exhibit an average radius of curvature that is greater than or less than the second curved shape and/or the first curved shape may exhibit a curvature that is different than the second curved shape (e.g., the first curved shape is concave or convex relative to point P2 and the second curved shape is the other of concave or convex relative to point P2).

Figure 2A:
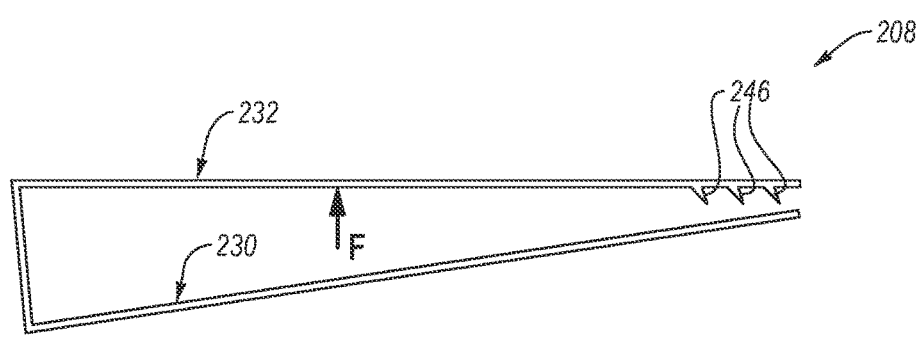
FIG. 2A is a side view of an adjustable spine that includes a second strip that is configured to convexly curve when a force is applied thereto, according to an embodiment.
Figure 2B:
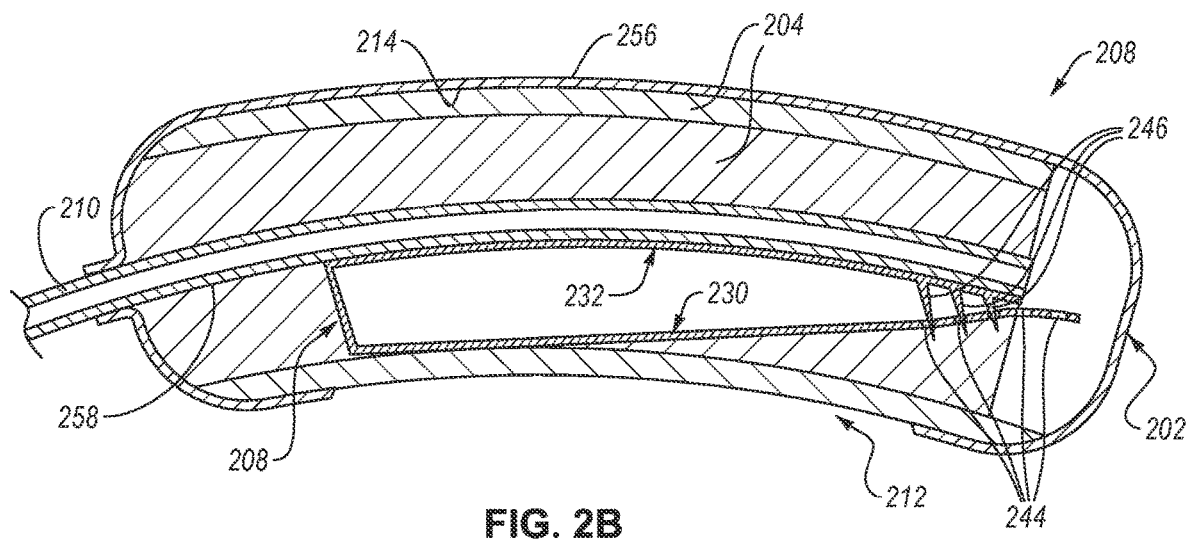
FIG. 2B is a cross-sectional schematic of a fluid collection assembly with the adjustable spine disposed therein while the second strip exhibits the stressed configuration thereof, according to an embodiment.

As previously discussed, the second strip 132 is substantially straight when the second strip 132 exhibits the relaxed configuration and the force F causes the second strip 132 to concavely curve. However, it is noted that the second strips discloses herein may be configured to be convexly curved when a force F is applied thereto. For example, FIG. 2A is a side view of an adjustable spine 208 that includes a second strip 232 that is configured to convexly curve when a force F is applied thereto, according to an embodiment. FIG. 2B is a cross-sectional schematic of a fluid collection assembly 200 with the adjustable spine 208 disposed therein while the second strip 232 exhibits the stressed configuration thereof, according to an embodiment. Except as otherwise disclosed herein, the adjustable spine 208 and the fluid collection assembly 200 are the same or substantially similar to any of the adjustable spines and fluid collection assemblies, respectively, disclosed herein. For example, the adjustable spine 208 may include first and second strips 230, 232 and the fluid collection assembly 200 may include a fluid impermeable barrier 202, at least one porous material 204, and a conduit 210. The features of the adjustable spine 208 and the fluid collection assembly 200 disclosed herein may be used in any of the embodiments disclosed herein.

A force F may be applied to the adjustable spine 208. Unlike the adjustable spine 108 illustrated in FIG. 1E, the force F is applied to the second strip 232 in a direction that causes the second strip 232 to bend (e.g., bow) away from the first strip 230. Thus, the force F causes the second strip 232 to form a convex curve when the second strip 232 is in the stressed configuration. The steps of the adjustable spine 208 may engage in any of the manners disclosed herein to maintain the second strip 232 in the stressed configuration after the force F is removed. For example, the first strip 230 may include one or more first steps 244 (FIG. 2B) that define recesses therebetween and the second strip 232 may include one or more second steps 246 that are each protrusions. The protrusions may be at least partially positioned in the recesses.

Due to the convex curve of the second strip 232, the second strip 232 may be attached to a surface of a component of the fluid collection assembly 200 that exhibits a concave curve relative to the opening 212 when the fluid collection assembly 200 exhibits the second shape. In an example, as illustrated, the second strip 232 may be attached to the conduit top surface 258. In an example, the second strip 232 may be attached to a surface of the porous material 204. In an example, the second strip 232 may be attached to the inner surface 214 of the back side 256 of the fluid impermeable barrier 202.

FIGS. 1C and 1F-2B illustrate that the steps of the adjustable spines thereof include one or more recess formed in the first strips thereof and one or more protrusions formed on the second strips thereof. However, the steps of any of the adjustable spines disclosed herein may include one or more protrusions formed on the first strip and one or more recesses formed in the second strip. For example, FIGS. 3A and 3B are side views of an adjustable spine 308 that includes one or more protrusions formed on the first strip 330 thereof and one or more recesses formed in the second strip 332 thereof, according to an embodiment. FIG. 3C is an enlarged cross-sectional schematic of the portion of the adjustable spine 308 shown in the circle 3C of FIG. 3B, according to an embodiment. Except as otherwise disclosed herein, the adjustable spine 308 may be the same or substantially similar to any of the adjustable spines disclosed herein. For example, the adjustable spine 308 includes a first strip 330, a second strip 332, and, optionally, a crossbeam 342. The features of the adjustable spine 308 may be used in any of the embodiments disclosed herein.

The first strip 330 includes one or more first steps 344 and the second strip 332 includes one or more second steps 346. The first steps 344 include one or more protrusions extending from a main surface 352 and the second steps 346 defines one or more recesses therebetween (shown in FIG. 3C). The protrusions and the recesses may be the same or substantially similar to any of the protrusions and recesses disclosed herein. For example, each of the protrusions may include a first surface 348 and a second surface 350 extending from the main surface 352. As previously discussed, the angle between the first surface 348 and the main surface 352 is obtuse and the angle between the second surface 350 and the main surface 352 is acute, perpendicular, or less obtuse than the angle between the first and main surfaces 348, 352. Such angles between the first and second surfaces 348, 350 and the main surface 352 may allow the second strip 332 to switch from the relaxed configuration to the stressed configuration while inhibiting the second strip 332 from relaxing.

Figure 4A:
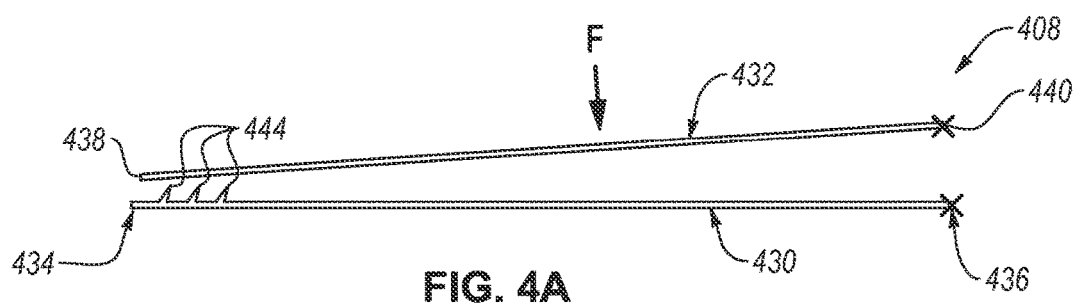
FIGS. 4A and 4B are side views of an adjustable spine is a first state and a second state, respectively, according to an embodiment.
Figure 4B:
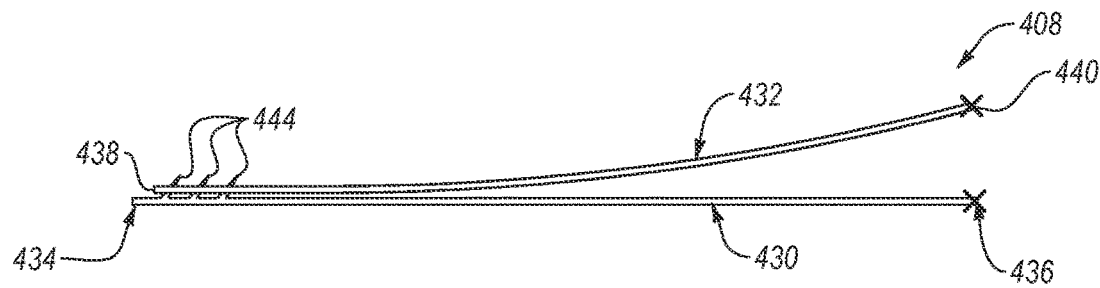

In some embodiments, the crossbeam may be omitted from the adjustable spines disclosed herein. For example, FIGS. 4A and 4B are side views of an adjustable spine 408 is a first state and a second state, respectively, according to an embodiment. Except as otherwise disclosed herein, the adjustable spine 408 is the same or substantially similar to any of the adjustable spines disclosed herein. For example, as previously discussed, the adjustable spine 408 includes a first strip 430 and a second strip 432. However, the adjustable spine 408 does not include a crossbeam. The features of the adjustable spine 408 may be used in any of the other embodiments disclosed herein.

Figure 4C:
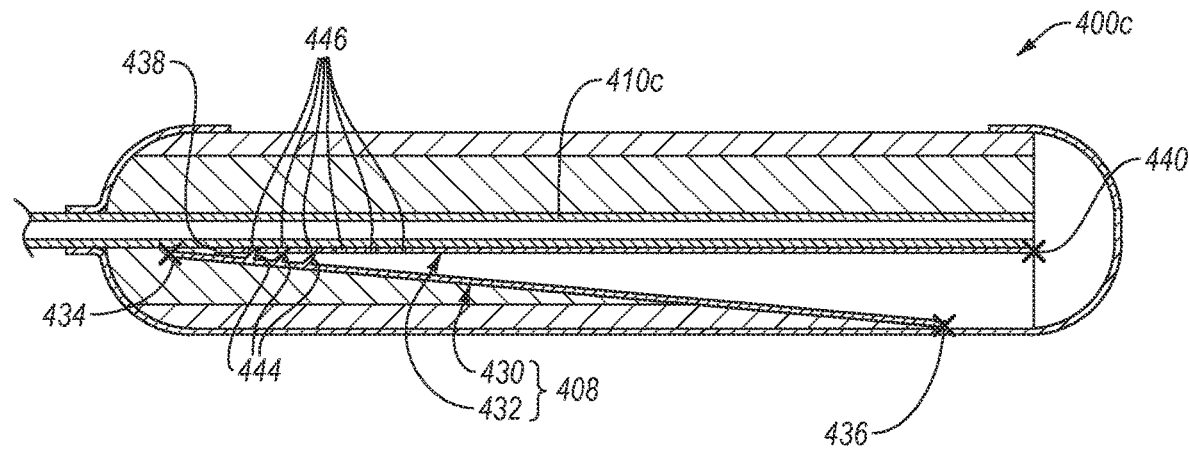
FIGS. 4C and 4D are cross-sectional schematics of different fluid collection assemblies that include the adjustable spine shown in FIGS. 4A and 4B, according to different embodiments.
Figure 4D:
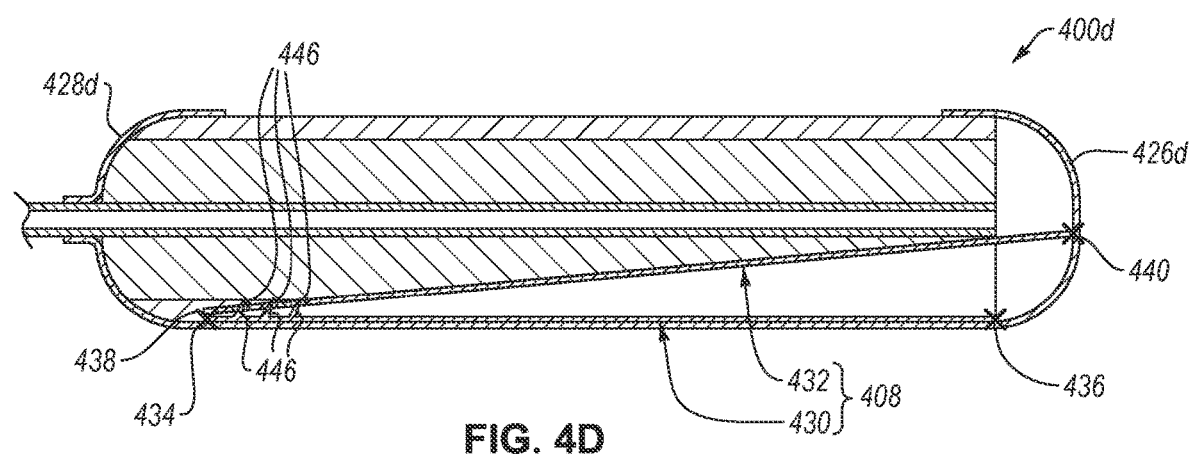

The first strip 430 includes a first terminal end 434 and a second terminal end 436 opposite the first terminal end 434. In the illustrated embodiment, the first strip 430 includes one or more first steps 444 formed in a portion of the first strip 430 at or near the first terminal end 434. The second strip 432 includes a third terminal end 438 and a fourth terminal end 440. The second strip 432 may include one or more second steps 446 (e.g., the second steps 446 defines one or more recesses therebetween as shown in FIGS. 4C and 4D) at or near the third terminal end 438. It is noted that one of the first steps 444 or the second steps 446 may be omitted from the adjustable spine 408 or may exhibit a different arrangement than what is illustrated. Generally the first terminal end 434 is proximate to the third terminal end 438 which allows the steps of the adjustable spine 408 to become engaged.

One or more of the first, second, third, or fourth terminal ends 434, 436, 438, 440 are fixedly attached to one or more components of the fluid collection assembly 400. For example, he first terminal end 434 and/or the second terminal end 436 of the first strip 430 and the fourth terminal end 440 are fixedly attached (schematically illustrated with an X) to one or more components of the fluid collection assembly 400. The first terminal end 434, the second terminal end 436, and the fourth terminal end 440, may be fixedly attached to one or more components of the fluid collection assembly 400 using any suitable technique, such as with an adhesive, welding, or a mechanical attachment.

The first and fourth terminal ends 434, 440 may be attached to different portions of the same component or different components. In an embodiment, the first and fourth terminal ends 434, 440 may be attached to or near opposing ends of the fluid collection assembly 400 which allows the adjustable spine 408 to change the shape of all or substantially all of the fluid collection assembly 400. For example, the first terminal end 434 may be attached to or near a proximal or distal end region of the fluid collection assembly while the fourth terminal end 440 may be attached to or near the other of the proximal or distal end region. For example, FIGS. 4C and 4D are cross-sectional schematics of different fluid collection assemblies that include the adjustable spine 408 shown in FIGS. 4A and 4B, according to different embodiments. Except as otherwise disclosed herein, the fluid collection assemblies illustrated in FIGS. 4C and 4D may be the same or substantially similar to any of the fluid collection assemblies disclosed herein. It is also noted that the embodiments illustrated in FIGS. 4C and 4D are provided for illustrative purposes only and should not be construed as limiting. Referring to FIG. 4C, the first terminal end 434 of the first strip 430 may be attached to the conduit 410c of the fluid collection assembly 400 at or near the proximal end region 428d of the fluid collection assembly 400. The fourth terminal end 440 of the second strip 432 is fixedly attached to the conduit 410c near the distal end region 426d of the fluid collection assembly 400c. The second terminal end 436 is illustrated as being fixedly attached to the fluid impermeable barrier 402c though the second terminal end 436 may not be fixedly attached to anything. Referring to FIG. 4D, the first terminal end 434 of the first strip 430 may be fixedly attached to the fluid impermeable barrier 402d at or near a proximal end region 428d of the fluid collection assembly 400d. The fourth terminal end 440 of the second strip 432 may be fixedly attached to the fluid impermeable barrier 402d at or near the distal end region 426d of the fluid collection assembly 400d. The second terminal end 436 may optionally be fixedly attached to the fluid impermeable barrier 402d at or near the distal end region 426d. In an embodiment, the first and fourth terminal ends 434, 440 may not be attached to or near opposing ends of the fluid collection assembly 400 which allows the adjustable spine 408 to only change the shape of a portion of the fluid collection assembly 400.

Referring back to FIG. 4A, the adjustable spine 408 and the second strip 432 are in the first state and relaxed configuration thereof, respectively. A force F is applied to the second strip 432. Because the fourth terminal end 440 and at least one of the first or second terminal ends 434, 436 are fixedly attached to one or more components of the fluid collection assembly 400, portion of the second strip 432 moves towards a portion of the first strip 430 and the steps of the adjustable spine 408 become engaged. In other words, the force F changes the adjustable spine 408 and the second strip 432 to the second state and relaxed configuration thereof.

In an embodiment, as illustrated, the force F may cause the second strip 432 to bend such that the second strip 432 changes a shape thereof when the second strip 432 changes from the relaxed configuration to the stressed configuration. The second strip 432 may be attached to a component of the fluid collection assembly 400 along at least a portion of the length of the second strip 432 such that the change in the shape of the second strip 432 changes the shape of the component to which the second strip 432 is attached, as previously discussed. However, in an embodiment, the second strip 432 is not attached to a component of the fluid collection assembly along at least a portion of the length thereof, as previously discussed. Instead, switching the second strip 432 from the relaxed configuration to the stressed configuration may force the fluid collection assembly 400 to bend to relieve at least some of the tensile forces that are applied by the first and fourth terminal ends 434, 440 when the second strip 432 is in the stressed configuration. In such an embodiment, switching the second strip 432 from the relaxed configuration to the stressed configuration may cause the second strip 432 to bend or the shape of the second strip 432 may remain at least substantially unchanged since the change in the shape of the fluid collection assembly 400 is predominately caused by the need to relieve tensile forces instead of a change in the shape of the second strip 432.

In an embodiment, a shape of the first strip 430 may remain unchanged when the adjustable spine 408 switches from the first state to the second state. In an embodiment, a shape of the first strip 430 may change when the adjustable spine 408 switches from the first state to the second state. The first strip 430 may change a shape thereof to accommodate a shape change of the fluid collection assembly 400 to prevent the first strip 430 from restricting the ability of the fluid collection assembly 400 to change a shape thereof. For example, referring to FIG. 4D, the first strip 430 is proximate to and extends along substantially all of a length of the fluid impermeable barrier 402d. If the first strip 430 did not change a shape thereof, the first strip 430 may prevent the fluid impermeable barrier 402d from exhibiting a shape change. As such, the first strip 430 may be sufficiently flexible to accommodate the shape change of the fluid impermeable barrier 402d. However, referring to FIG. 4C, the first strip 430 is spaced from a portion of the fluid impermeable barrier 402c such that the first strip 430 may not need to change a shape thereof to accommodate a shape change of the fluid impermeable barrier 402c. When the first strip 430 is configured to change a shape thereof, the first strip 430 may exhibit a rigidity that is less than or equal to the second strip 432.

Figure 5:
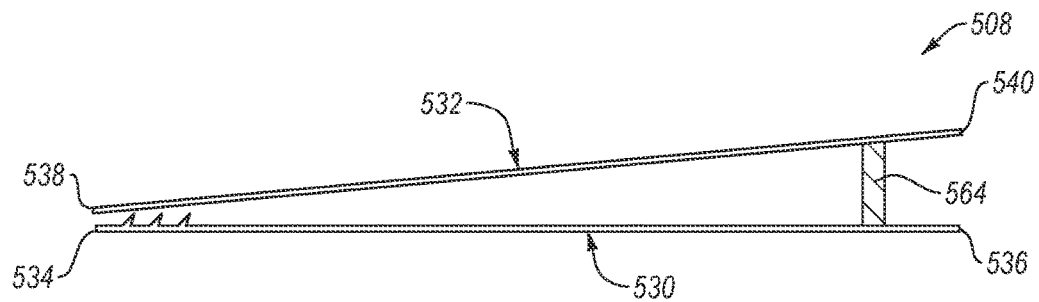
FIG. 5 is a side view of an adjustable spine, according to an embodiment.

FIG. 5 is a side view of an adjustable spine 508, according to an embodiment. Except as otherwise disclosed herein, the adjustable spine 508 may be the same or substantially similar to any of the adjustable spines 508 disclosed herein. For example, the adjustable spine 508 may include a first strip 530 having first and second terminal ends 534, 536 and a second strip 532 having third and fourth terminal ends 538, 540. The adjustable spine 508 may also exhibit at least a first state when the second strip 532 is in the relaxed configuration (as shown) and a second state when the second strip 532 is in the stressed configuration. The features of the adjustable spine 508 may be used in any of the embodiments disclosed herein.

The adjustable spine 508 does not include a crossbeam. Instead, the adjustable spine 508 includes a spacer 564 that, similar to the crossbeams disclosed herein, is configured to maintain a portion of the first strip 530 spaced from a portion of the second strip 532. However, unlike the crossbeams disclosed herein, the spacer 564 may be at least one of compressible, porous, attached directly to at most one of the first or second strip 530, 532, or spaced from the second and fourth terminal ends 536, 540. In an example, the spacer 564 may include a portion of the porous material of the fluid collection assembly that includes the adjustable spine 508 when the porous material exhibits sufficient rigidity to maintain the space between the first and second strips 530, 532. In an example, the spacer 564 includes rubber or other compressible polymer, a metal, a sponge-like structure that is distinct from the porous material, a reinforced porous material, or any other suitable material. It is noted that the spacer 564 is only positioned between a portion of the first strip 530 and a portion of the second strip 532.

The adjustable spines disclosed herein may include three or more strips, such as two or more strips that are configured change a configuration thereof. For example, FIG. 6A is a side view of an adjustable spine 608, according to an embodiment. Except as otherwise disclosed herein, the adjustable spine 608 is the same or substantially similar to any of the adjustable spines disclosed herein. Further, any of the features of the adjustable spine 608 may be used in any of the embodiments disclosed therein.

The adjustable spine 608 includes a first strip 630 that includes a first terminal end 634 and a second terminal end 636. The adjustable spine 608 also includes a second strip 632 and a third strip 666 that are each configured to switch independently from each other at least from a relaxed configuration to a stressed configuration. The second strip 632 includes a third terminal end 638 and a fourth terminal end 640 and the third strip 666 includes a fifth terminal end 668 and a sixth terminal end 670. The first, second, and third strips 630, 632, 666 may be arranged such that at least one of the first and fourth terminal ends 634, 640 are proximate to each other, the second and sixth terminal ends 636, 670 are proximate to each other, or the third and fifth terminal ends 638, 668 are proximate to a middle portion of the first strip 630 between the first and second terminal ends 634, 636. In other words, the second strip 632 may extend next to a portion of the first strip 630 and the third strip 666 may extend along another portion of the first strip 630.

In an embodiment, as shown, the fourth terminal end 640 and the sixth terminal end 670 of the second and third strips 632, 666 are fixedly secured to one or more components of the fluid collection assembly 600 (shown in FIG. 6B). At least one of the first or second terminal ends 634, 636 of the first strip 630 are also fixedly secured to one or more components of the fluid collection assembly 600. In an embodiment, not shown, the adjustable spine 608 includes at least one crossbeam extending between the first and fourth terminal ends 634, 640 and/or the second and sixth terminal ends 636, 670.

One or more of the first, second, or third strips 632, 632, 666 include one or more steps that are configured to become engaged. For example, at least one the first strip 630 may include one or more first steps 644 that are configured to engage at least one of the second or third strip 632, 666, the second strip 632 may include one or more second steps 646 (FIG. 6B) that are configured to engage the first strip 630 (e.g., engage the first steps 644), or the third strip 666 may include one or more third steps 667 (FIG. 6B) that are configured to engage the first strip 630 (e.g., engage the first steps 644). The steps may include any of the steps in any of the arrangements disclosed herein. For example, the first steps 644 may include one or more protrusions extending therefrom and, optionally, the second and third steps 646, 667 may define one or more recesses therebetween. When the first steps 644 includes one or more protrusions, the first steps 644 may include at least one first protrusion 644a that is configured to engage the second strip 632 and at least one second protrusion 644b that is configured to engage the third strip 666. The first and second protrusions 644a, 644b may be angled differently to facilitate engagement with second and third strips 632, 666, respectively. For example, the first protrusions 644a is angled towards the first terminal end 634 and the second protrusions 644b may be angled towards the second terminal end 636 since angling the first and second protrusions 644a, 644b in a different manner may prevent the first steps 644 from engaging the second and third strips 632, 666. The first protrusion 644a is angled towards the first terminal end 634 when the angle between a surface of the first protrusion that is closest to the first terminal end 634 is smaller (e.g., an acute angle) than the angle between a surface of the same first protrusion that is closer to the second terminal end 636. The second protrusion 644b is angled towards the second terminal end 636 when the angle between a surface of the second protrusion 644b that is closest to the second terminal end 636 is smaller (e.g., an acute angle) than the angle between a surface of the same second protrusion 644b that is closer to the first terminal end 634. It is noted that when at least one of the second or third strips 632, 666 include protrusions, the protrusions may be angled towards the third and fifth terminal ends 638, 668 thereof, respectively.

During use, a force (not shown) may be applied to at least one of the second or third strip 632, 666. For example, a force may be applied to only one of the second or third strip 632, 666; the same force may be applied to both of the second and third strips 632, 666; or forces having different magnitudes may be applied to the second and third strips 632, 666. In other words, the force may be applied independently to each of the second and third strips 632, 666. The forces applied to the second and third strips 632, 666 causes the second and third strips 632, 666 to engage with the first strip 630 thereby switching the second and third strips 632, 666 from the relaxed configuration to the stressed configuration.

FIG. 6B is a cross-sectional schematic of a fluid collection assembly 600 that includes the adjustable spine 608 shown in FIG. 6A, according to an embodiment. Except as otherwise disclosed herein, the fluid collection assembly 600 is the same or substantially similar to any of the fluid collection assemblies disclosed herein. For example, the fluid collection assembly 600 may include a fluid impermeable barrier 602, at least one porous material 604, and a conduit 610. The adjustable spine 608 may allow different portions of the fluid collection assembly 600 to be shape differently and/or independently of each other. For example, the fluid collection assembly 600 may include a first portion 672 and a second portion 674. The first portion 672 includes the second strip 632 and the second portion 674 includes the third strip 666. The second strip 632 is configured to at least partially control the shape of the first portion 672. For example, the first portion 672 may exhibit a first shape and a second shape that is different than the first shape thereof when the second strip 632 exhibits the relaxed configuration and the stressed configuration, respectively. Further, the second portion 674 may exhibit a first shape and a second shape that is different than the first shape thereof when the third strip 666 exhibits the relaxed configuration and the stressed configuration, respectively. Thus, the adjustable spine 608 allows for more control over the shape of the fluid collection assembly 600 that if the adjustable spine 608 did not include the third strip 666.

Figure 7:
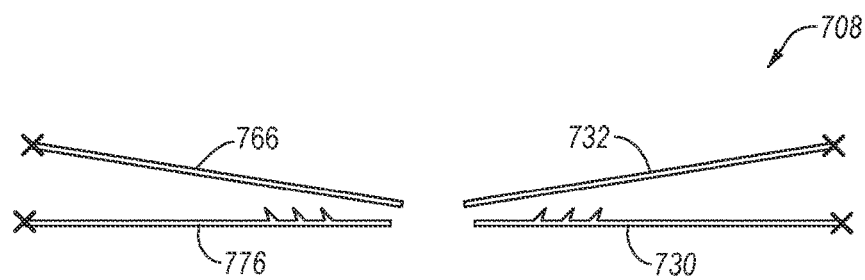
FIG. 7 is a side view of an adjustable spine, according to an embodiment.

FIG. 7 is a side view of an adjustable spine 708, according to an embodiment. Except as otherwise disclosed herein, the adjustable spine 708 is the same or substantially similar to any of the adjustable spines disclosed herein. The features of the adjustable spine 708 may be used in any of the embodiments disclosed herein.

The adjustable spine 708 is substantially the same as the adjustable spine 608 illustrated in FIGS. 6A and 6B except that the adjustable spine 708 includes a first strip 730 and a fourth strip 776 instead of a single first strip 630. For example, the adjustable spine 708 includes a second strip 732 and a third strip 766 that are substantially similar to the second and third strips 632, 666. The second strip 732 extends next to and is configured to engage with the first strip 730 and the third strip 766 extend next to and is configured to engage with the fourth strip 776. Thus, the first and second strips 730, 732 may be at least partially control the shape of a first portion of a fluid collection assembly (not shown) and the third and fourth strips 766, 776 may at least partially control the shape of a second portion of a fluid collection assembly.

Figure 8A:
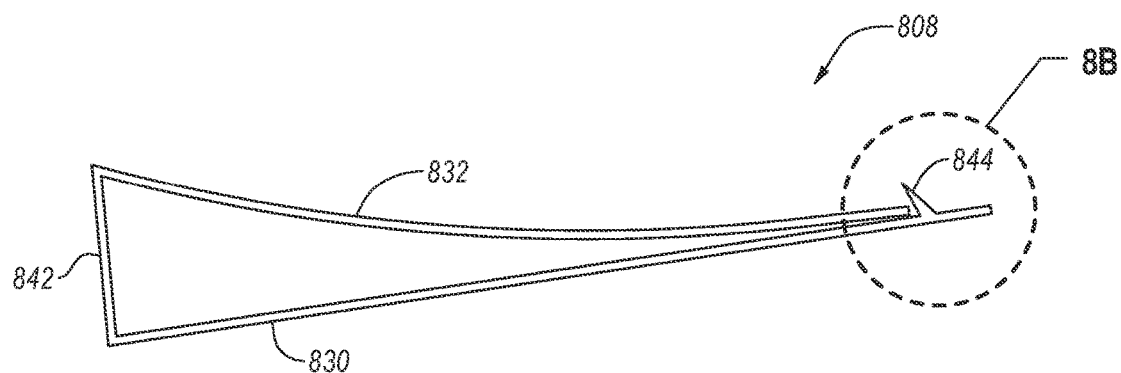
FIG. 8A is a side view of an adjustable spine in a second state, according to an embodiment.
Figure 8B:
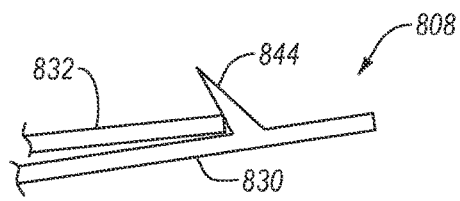
FIG. 8B is an enlarged side view of the adjustable spine within the circle 8B as shown in FIG. 8A, according to an embodiment.

In the embodiments disclosed above, the adjustable spines are mainly disclosed as including steps on each of the strips thereof. However, any of the adjustable spines disclosed herein may only include steps on one of the strips thereof. For example, FIG. 8A is a side view of an adjustable spine 808 in a second state, according to an embodiment. FIG. 8B is an enlarged side view of the adjustable spine 808 within the circle 8B as shown in FIG. 8A, according to an embodiment. Except as otherwise disclosed herein, the adjustable spine 808 may be the same or substantially similar to any of the adjustable spines disclosed herein. Further, the features of the adjustable spine 808 may be used in any of the embodiments disclosed herein.

The adjustable spine 808 includes a first strip 830 and a second strip 832 that is configured to switch at least from a relaxed configuration to a stressed configuration. In an embodiment, as illustrated, the adjustable spine 808 also includes a crossbeam 842 though it is noted that the crossbeam 842 may be omitted by fixedly attaching one or more of the terminal ends of the first and second strips 830, 832 to one or more components of the fluid collection assembly or using a spacer, as previously disclosed herein. The first strip 830 includes one or more steps 844. In an embodiment, as illustrated, the steps 844 may include one or more protrusions. In an embodiment, the one or more steps 844 may define one or more recesses therebetween that are configured to receive at least a portion of the second strip 832. In either embodiment, the second strip 832 does not include a step since the second strip 832, by itself and without any features extending therefrom or formed therein, is configured to engage with the steps 844. It is noted that the second strip 832 may include one or more steps formed therein or thereon instead of the first strip 830 when the first strip 830, by itself, may engage the step of the second strip 832.

Figure 9:
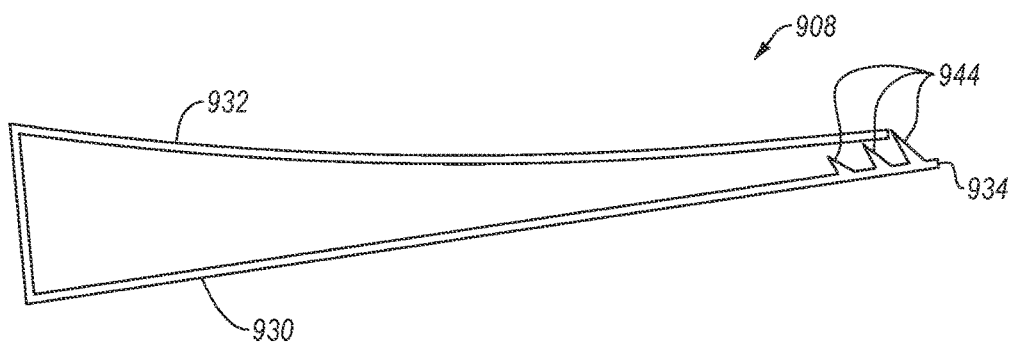
FIG. 9 is a side view of an adjustable spine, according to an embodiment.

As illustrated, the step 844 may only include a single protrusion. In some embodiments, depending on the configuration of the adjustable spine 808, the step 844 may only include a single protrusion because, without the recesses formed in the second strip 832, any additional protrusions that are the same size as the illustrated protrusion may form an obstacle that blocks the second strip 832 from engaging at least one of the protrusions, especially when the second strip 832 is concavely curved in the stressed configuration. However, such issues may be resolved by varying the heights of the protrusions or configuring the second strip 832 to convexly curve. For example, FIG. 9 is a side view of an adjustable spine 908, according to an embodiment. The adjustable spine 908 may be the same or substantially similar to any of the adjustable spines disclosed herein and the features thereof may be used in any of the embodiments disclosed herein. The adjustable spine 908 includes a first strip 930 and a second strip 932 and only the first strip 930 includes steps 944. The steps 944 includes a plurality of protrusions and the height of each of the protrusions varies. For example, the height of the protrusions may decrease with increasing distance from the first terminal end 934 of the first strip 930. Thus, none of the protrusion form obstacles.

Figure 10:
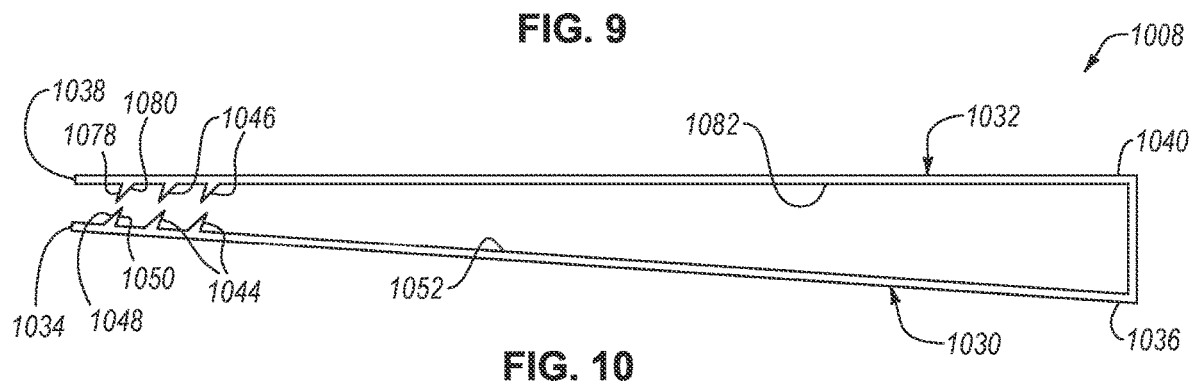
FIG. 10 is a side view of an adjustable spine, according to an embodiment.

In some of the embodiments disclosed herein, the steps of the adjustable spine are disclosed as including one or more protrusions and defining one or more recesses therebetween. However, it is noted that the steps may include protrusions formed on both the first and second strips. For example, FIG. 10 is a side view of an adjustable spine 1008, according to an embodiment. Except as otherwise disclosed herein, the adjustable spine 1008 may be the same or substantially similar to any of the adjustable spines disclosed herein. Further, the features of the adjustable spine 1008 may be used in any of the embodiments disclosed herein.

The adjustable spine 1008 includes a first strip 1030 and a second strip 1032. The first strip 1030 may include a first terminal end 1034 and a second terminal end 1036 and the second strip 1032 may include a third terminal end 1038 and a fourth terminal end 1040. The first strip 1030 also include one or more first steps 1044 and the second strip 1032 includes one or more second steps 1046. The first and second steps 1044, 1046 include one or more protrusions extending from the first and second strips 1030, 1032, respectfully.

The protrusions of the first and second steps 1044, 1046 are configured to engage with each other. For example, the protrusions of the first steps 1044 may include a first surface 1048 and a second surface 1050 that extend from a main surface 1052. The first surface 1048 is closer to the first terminal end 1034 than the second surface 1050 of the same protrusion. The angle between the first surface 1048 and the main surface 1052 may be obtuse while the angle between the second surface 1050 and the main surface 1052 is one of an acute angle, a right angle, or less obtuse than the angle between the first and main surfaces 1048, 1052. Further, the protrusions of the second steps 1046 may include a third surface 1078 and a fourth surface 1080 that extend from a main surface 1081. The third surface 1078 is closer to the third terminal end 1038 than the fourth surface 1080 of the same protrusion. The angle between the fourth surface 1078 and the main surface 1082 may be obtuse while the angle between the third surface 1078 and the main surface 1082 is one of an acute angle, a right angle, or less obtuse than the angle between the fourth and main surfaces 1078, 1082. Such angles of the protrusions of the first and second steps 1044, 1046 allows the first and second steps 1044, 1046 to engage each other while inhibiting the second strip 1032 from relaxing.

Figure 11A:
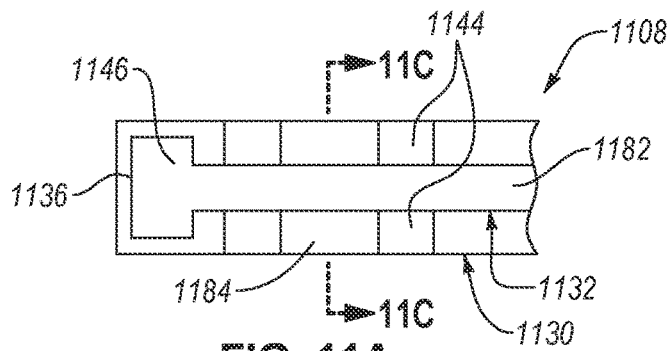
FIGS. 11A and 11B are a top plan and side view of a portion of an adjustable spine in a first state, according to an embodiment.
Figure 11B:
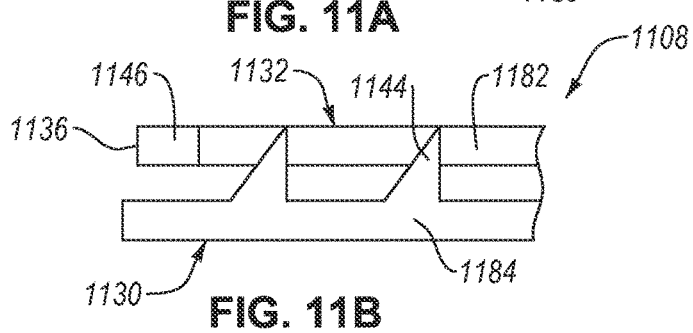
Figure 11C:
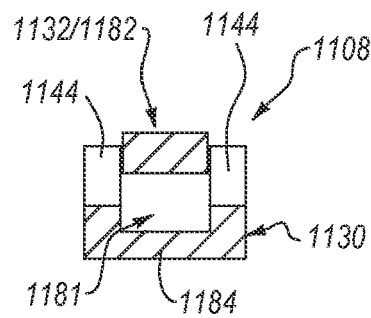
FIG. 11C is a cross-sectional schematic of the adjustable spine taken along plane 11C-11C shown in FIG. 11A, according to an embodiment.

Some of the strips disclosed herein a relatively narrow (e.g., not very wide) compared to a length thereof. The relatively narrow width of the strips may cause the second strip to slide sideways off the first strip when the force applied to the second strip is not orthogonal to the length and width of the strips. Siding the second strip off the first strip may cause the steps thereof to become disengaged or prevent the engagement of the steps. As such, at least one of the strips of any of the adjustable spines disclosed herein may include one or more features to inhibit the second strip from sliding sideways off the first strip when a force is applied to the second strip. FIGS. 11A and 11B are a top plan and side view of a portion of an adjustable spine 1108 in a first state, according to an embodiment. FIG. 11C is a cross-sectional schematic of the adjustable spine 1108 taken along plane 11C-11C shown in FIG. 11A, according to an embodiment. Except as otherwise disclosed herein, the adjustable spine 1108 may be the same or substantially similar to any of the adjustable spines disclosed herein. Further, the features of the adjustable spine 1108 may be used in any of the embodiments disclosed herein.

The adjustable spine 1108 includes a first strip 1130 and a second strip 1132. The first strip 1130 includes one or more first steps 1144 formed therein. The one or more first steps 1144 include protrusions extending from a base 1184 thereof. The protrusions of the first steps 1144 are arranged in one or more rows with each row including at least two protrusions separated by a recess 1181. The second strip 1132 includes a longitudinally extending portion 1182 exhibiting a width measured perpendicular to the longitudinal length of the second strip 1132 that is sufficient to fit within the recess 1181 (e.g., is less than a space between the protrusions of the same row). As such, the two protrusions of each row that the longitudinally extending portion 1182 is positioned between forms walls that inhibit the second strip 1132 from sliding sideways off the first strip 1130 even when the force applied to the second strip 1132 causes the longitudinally extending portion 1182 to press against one or more of the protrusions.

The second strip 1132 also include a second step 1146 formed at or near the third terminal end 1138 thereof. The second step 1146 exhibits a width measured perpendicular to the longitudinal length of the second strep 1132 that is too great to fit in the recess 1181. In other words, the width of the second step 1146 is greater than the space of the recess 1181 measured between the protrusions of the same row.

Figure 11D:
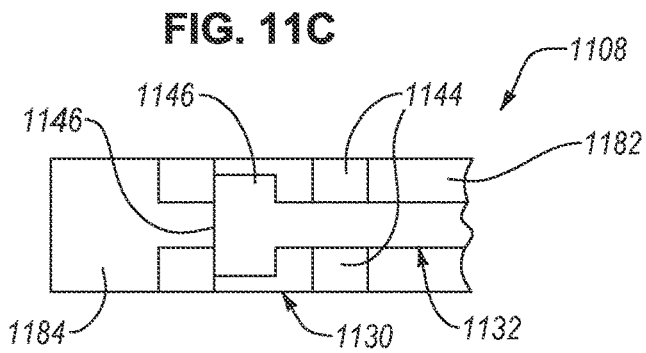
FIGS. 11D and 11E are a top plan and side views, respectively, of the adjustable spine in the second state, according to an embodiment.
Figure 11E:
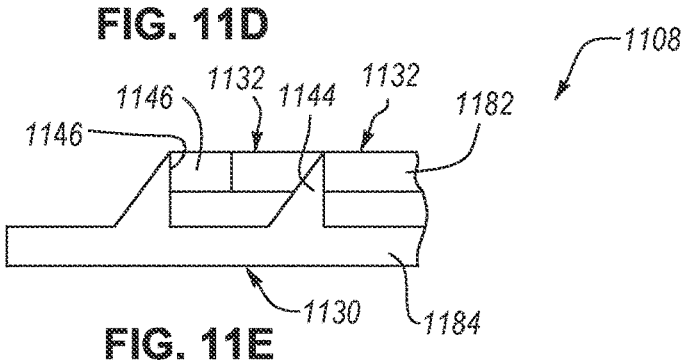

The protrusions of the first steps 1144 may include a first surface 1148 and a second surface 1150 extending from a main surface 1152 of the first strip 1130. The first surface 1148 may be closer to the first terminal end 1134 of the first strip 1130 than the second surface 1150. The angle between the first surface 1148 and the main surface 1152 may be an obtuse angle and the angle between the second surface 1150 and the main surface 1152 may be less than the angle between the first and main surfaces 1148, 1152 (e.g., an acute or right angle). The angles of the first and second surfaces 1148, 1150 and the main surface 1152 may facilitate operation of the adjustable spine 1108. For example, FIGS. 11A and 11B illustrate the adjustable spine 1108 in the first state and the second strip 1132 is in the relaxed configuration. Switching the adjustable spine 1108 and the second strip 1132 to the second state and stressed configuration thereof, respectively, includes moving the third terminal end 1138 of the second strip 1132 away from the first terminal end 1134 of the first strip 1130. The obtuse angle between the first and main surfaces 1148, 1152 allows the second step 1146 to easily move over the protrusions of the first steps 1144. FIGS. 11D and 11E are a top plan and side views, respectively, of the adjustable spine 1108 in the second state, according to an embodiment. As shown in FIGS. 11D and 11E, the second step 1146 may press against the second surface 1150 of the first steps 1144 when the second strip 1132 attempts to relax. However, the angle between the second surface 1150 and the main surface 1152 may inhibit the second strip 1132 from relaxing since the angle therebetween is less than the angle between the first and main surfaces 1148, 1152.

Figure 12A:
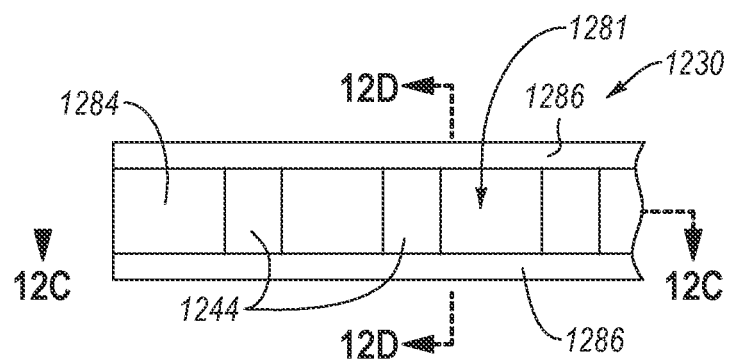
FIGS. 12A and 12B are top plan views of a first strip and a second strip, respectively, of an adjustable spine, according to an embodiment.
Figure 12B:
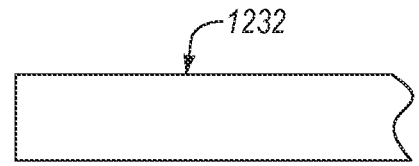
Figure 12C:
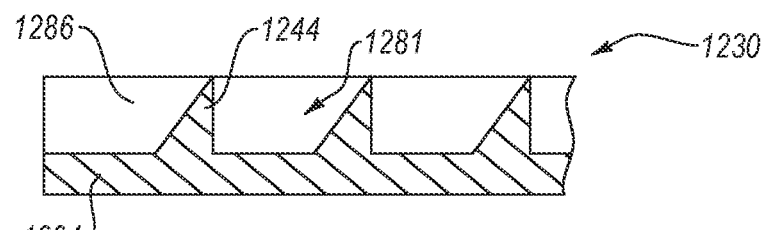
FIGS. 12C and 12D are cross-sectional schematics of the first strip taken along planes 12C-12C and 12D-12D as shown in FIG. 1A, according to an embodiment.
Figure 12D:
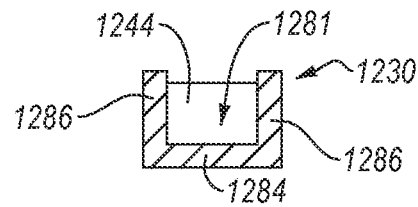

FIGS. 12A and 12B are top plan views of a first strip 1230 and a second strip 1232, respectively, of an adjustable spine, according to an embodiment. FIGS. 12C and 12D are cross-sectional schematics of the first strip 1230 taken along planes 12C-12C and 12D-12D as shown in FIG. 12A, according to an embodiment. Except as otherwise disclosed herein, the adjustable spine illustrated in FIGS. 12A-12D may be the same or substantially similar to any of the adjustable spines disclosed herein. The features of the adjustable spine illustrated in FIGS. 12A-12D may be used in any of the embodiments disclosed herein.

The first strip 1230 includes a base 1284 and two side walls 1286 extending upwardly from the longitudinally extending edges of the base 1284. The two side walls 1286 define a channel 1281 therebetween. The first strip 1230 also includes one or more steps 1244 formed in or on the base 1284 at a location between the two side walls 1286. For example, in the illustrated embodiment, the first steps 1244 include protrusions. When the first steps 1244 include protrusions, the side walls 1286 may extend further from the base 1284 than the protrusions such that the protrusions do not interrupt the channel 1281 since interrupting the channel 1281 may inhibit the function of the channel 1281. It is noted that the second strip 1232 may include one or more steps instead of or in addition to the first strip 1230.

The second strip 1232 exhibits a width that is configured to fit in the channel 1281. In other words, the width of the second strip 1232 is less than the space between the two side walls 1286. Thus, when the second strip 1232 is positioned between the side walls 1286, the side walls 1286 inhibits the second strip 1232 from sliding off the side of the first strip 1230.

Figure 13A:
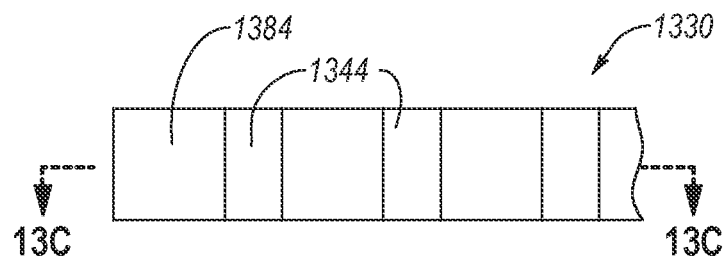
FIGS. 13A and 13B are top plan views of a first strip and a second strip, respectively, of an adjustable spine, according to an embodiment.
Figure 13B:
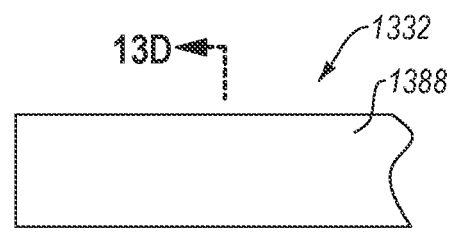
Figure 13C:
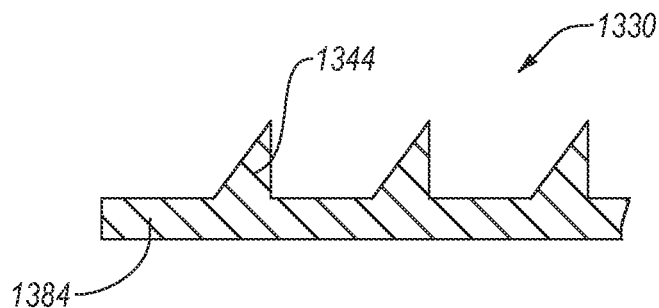
FIGS. 13C and 13D are cross-sectional schematics of the first and second strips taken along planes 13C-13C and 13D-13D as shown in FIGS. 13A and 13B, respectively, according to an embodiment.
Figure 13D:
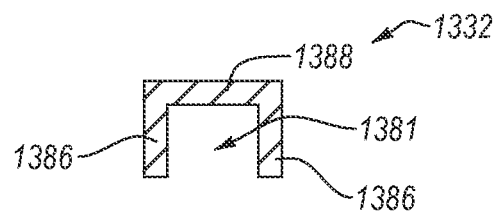

FIGS. 13A and 13B are top plan views of a first strip 1330 and a second strip 1332, respectively, of an adjustable spine, according to an embodiment. FIGS. 13C and 13D are cross-sectional schematics of the first and second strips 1330, 1332 taken along planes 13C-13C and 13D-13D as shown in FIGS. 13A and 13B, respectively, according to an embodiment. Except as otherwise disclosed herein, the adjustable spine illustrated in FIGS. 13A-13D may be the same or substantially similar to any of the adjustable spines disclosed herein. The features of the adjustable spine illustrated in FIGS. 13A-13D may be used in any of the embodiments disclosed herein.

The first and second strip 1330, 1332 illustrated in FIGS. 13A-13D may be substantially similar to the first and second strips 1230, 1232 illustrated in FIGS. 12A-12D. For example, the first strip 1330 may include a base 1384 and, optionally, one or more steps 1344 formed therein or thereon. It is noted that the second strip 1332 may include one or more steps instead of or in addition to the steps 1344. However, the second strip 1332 includes a base 1388 and two side walls 1386 extending from the longitudinal edges of the second strip 1332. The two side walls 1386 may form a channel 1381 therebetween and the first strip 1330 may be configured to be positioned within the channel 1381. The two side walls 1386 may inhibit the second strip 1332 from siding sideways off the first strip 1330 when the first strip 1330 is positioned within the channel 1381. It is noted that, as discussed herein, it is relative whether the first strip sides sideways off the seconds strip or the second strip slides sideways off the first strip.

In some of the embodiments disclosed herein, the steps of the adjustable spines disclosed herein may be configured to become disengaged by sliding the second strip off the side of the first strip. For example, the steps of the adjustable spines of FIGS. 8A-10, as illustrated, may become disengaged by sliding the second strip sideways off the first strip. This may allow a user of the fluid collection assembly to easily disengage the steps by merely applying a force that is not perpendicular to the second strip to disengage the steps. A user may want to disengage the steps of the adjustable spines disclosed herein because, for example, the shape change in the fluid collection assembly was too great and the shaping process needs to be restarted or the shape of the region about the urethral opening changed (e.g., the patient moved from a sitting to a lying position). However, in some embodiments, it may be beneficial to have one or more features that inhibit the second strip from siding off the first strip when a first force is applied to the second strip and allows the second strip to side off the first strip when a second force is applied to the second strip. FIGS. 14A-16 illustrate embodiments where that inhibit the second strip from siding off the first strip when a first force is applied to the second strip and allows the second strip to side off the first strip when a second force is applied to the second strip.

Figure 14A:
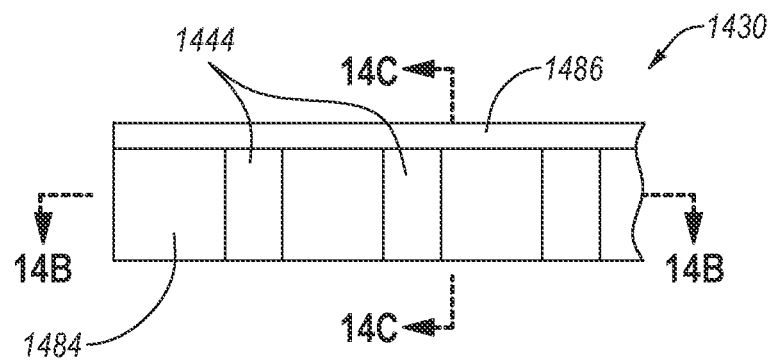
FIG. 14A is a top plan view of a strip, according to an embodiment.
Figure 14B:
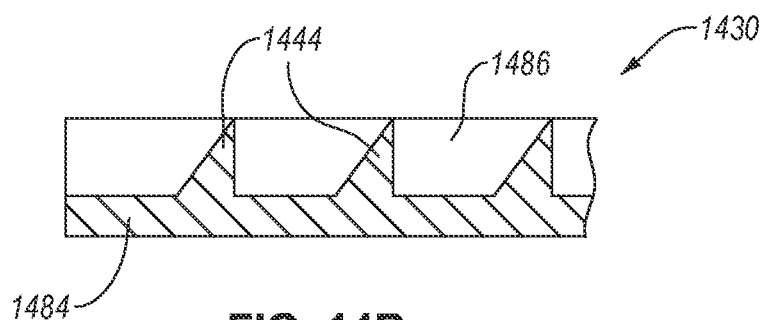
FIGS. 14B and 14C are cross-sectional schematics of the strip taken along planes 14B-14B and 14C-14C as shown in FIG. 14A, according to an embodiment.
Figure 14C:
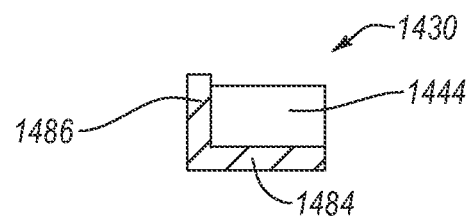

FIG. 14A is a top plan view of a strip 1430, according to an embodiment. FIGS. 14B and 14C are cross-sectional schematics of the strip 1430 taken along planes 14B-14B and 14C-14C as shown in FIG. 14A, according to an embodiment. The strip 1430 may be a first strip or a second strip. As such, the strip 1430 may be the same as or substantially similar to any of the first and second strips disclosed herein. The features of the strip 1430 may be used in any of the embodiments disclosed herein.

The strip 1430 includes a base 1484 and one side wall 1486 extending from only one longitudinal edge of the base 1484. Optionally, the strip 1430 may include one or more steps 1444, such as one or more protrusions, form in or on the base 1484. As such, the strip 1430 is substantially the same as the first strip 1230 illustrated in FIGS. 12A, 12C, and 12D or the second strip 1332 illustrated in FIG. 13B or 13C with just one side wall 1486 instead of two. The side wall 1486 inhibits an opposing strip from siding sideways when a force applied to the strip 1430 or the opposing strip causes the opposing strip to press against the side wall 1486. However, the opposing strip may side off the strip 1430 when the force applied to the strip 1430 or the opposing strip causes the opposing strip to slide away from the side wall 1486.

Figure 15:
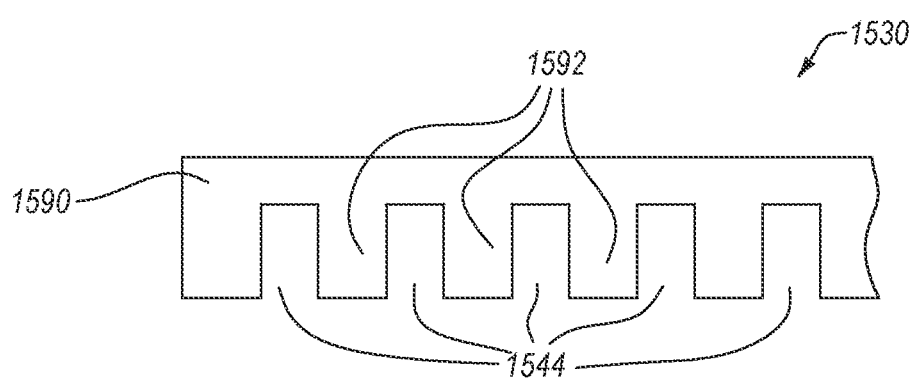
FIG. 15 is a side view of a strip, according to an embodiment.

FIG. 15 is a side view of a strip 1530, according to an embodiment. Except as otherwise disclosed herein, the strip 1530 may be the same or substantially similar to the first strip 130 illustrated in FIG. 1G. For example, the strip 1530 includes one or more recesses 1544 formed therein that, for instance, are configured to receive one or more protrusions. The strip 1530 may include a single longitudinally extending portion 1590 and a plurality of traversely extending portions 1592. The single longitudinally extending portion 1590 and the plurality of traversely extending portions 1592 define the recesses 1544. However, unlike the steps 144 illustrated in FIG. 1H, the recesses 1544 are not completely enclosed but instead include an open side. The recesses 1544 are not completely enclosed because the strip 1530 only includes a single longitudinally extending portion 1590. The longitudinally extending portion 1590 may inhibit an opposing strip from siding sideways when a force applied to the strip 1530 or the opposing strip causes one or more portions of the opposing strip (e.g., protrusions) to press against the longitudinally extending portion 1590. However, the opposing strip may side off the strip 1530 when the force applied to the strip 1530 or the opposing strip causes the opposing strip to slide away from the longitudinally extending portion 1590. It is noted that the strip 1530 may form a first strip or a second strip.

Figure 16:
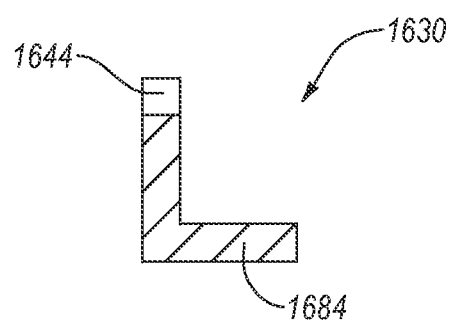
FIG. 16 is a cross-sectional schematic of a strip, according to an embodiment.

FIG. 16 is a cross-sectional schematic of a strip 1630, according to an embodiment. Except as otherwise disclosed herein, the strip 1630 may be the same as or substantially similar to the first strip 1130 illustrated in FIGS. 11A-11E. For example, the strip 1630 includes a base 1684 and a protrusion 1644 extending upwardly from a longitudinal edge of base 1684. The protrusion 1644 does not extend from the whole width of the base 1684. The protrusions 1644 may be arranged in one or more rows. However, unlike the first strip 1130, the protrusion 1644 in each row only includes a single protrusion 1644. The protrusion 1644 may inhibit an opposing strip from siding sideways when a force applied to the strip 1630 or the opposing strip causes one or more portions of the opposing strip to press against the protrusion 1644. However, the opposing strip may side off the strip 1630 when the force applied to the strip 1630 or the opposing strip causes the opposing strip to slide away from the protrusion 1644. It is noted that the strip 1630 may form a first strip or a second strip.

Some of the fluid collection assemblies discussed above disclose that the adjustable spines are disposed in a chamber defined by the fluid impermeable barrier thereof. However, it is noted that the adjustable spines disclosed herein may be disposed on an exterior of the fluid collection assembly. FIGS. 17A and 17B are isometric views of a fluid collection assembly 1700 with a cap 1792 and with the cap 1792 removed, respectively, according to an embodiment. FIG. 17C is a cross-sectional schematic of the fluid collection assembly 1700 taken along plane 17C-17C as shown in FIG. 17A, according to an embodiment. Except as otherwise disclosed herein, the fluid collection assembly 1700 is the same or substantially similar to any of the fluid collection assemblies disclosed herein. For example, the fluid collection assembly 1700 includes a fluid impermeable barrier 1702, at least one porous material 1704, and a conduit 1710. The fluid collection assembly 1700 also includes an adjustable spine 1708 (shown in FIGS. 17B and 17C). The adjustable spine 1708 is illustrated as being substantially similar to the adjustable spine 108 illustrated in FIGS. 1C-1H. However, the adjustable spine 1708 may include any of the adjustable spines disclosed herein. Regardless, the adjustable spine 1708 may include at least a first strip 1730 and a second strip 1732.

The fluid impermeable barrier 1702 includes a back side 1756 and the back side 1756 includes an outer surface 1716. The adjustable spine 1708 may be disposed on the outer surface 1716 of the back side 1756 since disposing the adjustable spine 1708 on the front side 1754 may prevent the opening 1712 from be disposed against a urethral opening of a patient.

Disposing the adjustable spine 1708 on the outer surfaced 1716 may facilitate the operation of the adjustable spine 1708. For example, disposing the adjustable spine 1708 on the outer surface 1716 may allow a user of the fluid collection assembly 1700 (e.g., the patient, a medical practitioner, etc.) to easily access the adjustable spine 1708, directly manipulate the adjustable spine 1708 (e.g., not have to manipulate the adjustable spine 1708 through the fluid impermeable barrier 1702), and allows the user to see what is happening to the adjustable spine 1708. For example, disposing the adjustable spine 1708 on the outer surface 1716 may the user to more controllably apply a force to the second strip 1732 without applying too small or too large of a force to the second strip 1732 and without causing the second strip 1732 to side sideways off the first strip 1730. Further, disposing the adjustable spine 1708 on the outer surface 1716 may facilitate disengagement of steps of the adjustable spine 1708 since the user may see how to disengage the steps, may actually see what the user is doing, and may directly manipulate the adjustable spine 1708.

When the adjustable spine 1708 is disposed on an outer surface 1716, the adjustable spine 1708 may come in contact with the skin of the patient. Contacting the adjustable spine 1708 may cause chaffing, increase patient discomfort, and may cause the steps of the adjustable spine 1708 from becoming inadvertently disengage, especially when the patient moves. As such, the fluid collection assembly 1700 may include a cap 1792. The cap 1792 includes an inner surface 1794 that defines a cavity 1796 (shown in FIG. 17C). The cavity 1796 may be sized to receive the adjustable spine 1708 therein such that the cap 1792 and the fluid impermeable barrier 1702 surrounds the adjustable spine 1708. In an embodiment, the cavity 1796 may be sized such that the inner surface 1794 of the cap 1796 abuts one or more portions of the adjustable spine 1708. When the inner surface 1794 abuts the adjustable spine 1708, the cap 1792 may be held in place via interference fit. Further, when the inner surface 1794 abuts the adjustable spine 1708, the inner surface 1794 may inhibit the second strip 1732 from sliding sideways off the first strip 1730.

The cap 1792 may be formed from any suitable material. In an example, the cap 1792 may be formed from a smooth and/or soft material to inhibit the cap 1792 from chaffing the patient. In an example, the cap 1792 may be formed from any of the fluid impermeable material(s) disclosed herein, such as the same material as the fluid impermeable barrier 1702. In an example, the cap 1792 may be formed from any of the porous material disclosed herein, such as a gauze.

In an embodiment, the cap 1792 is reversibly attached to the fluid impermeable barrier 1702 and the adjustable spine 1708. As used herein, reversibly attached means that the cap 1792 may be attached and detached to the fluid impermeable barrier 1702 and/or the adjustable spine 1708 more than once without substantially without damaging the fluid impermeable barrier 1702, the adjustable spine 1708, or the cap 1792. For example, the cap 1792 is reversibly attached to the fluid impermeable barrier 1702 and the adjustable spine 1708 when the cap 1792 exhibits an interference fit with, is magnetically attracted to, attached using a hook-and-loop fastener to, or attached with a mechanical fastener (e.g., screw, pin, etc.) to at least one of the fluid impermeable barrier 1702 or the adjustable spine 1708. Reversibly attaching the cap 1792 to the fluid impermeable barrier 1702 and the adjustable spine 1708 allows the cap 1792 to protect the adjustable spine 1708, isolate the adjustable spine 1708 from the patient such that the adjustable spine 1708 does not directly contact the skin of the patient, and allow the user of the fluid collection assembly 1700 direct access to the adjustable spine 1708. In an embodiment, the cap 1792 may be not reversibly attached to and instead permanently attached to at least one of the fluid impermeable 1702 or the adjustable spine 1708.

In an embodiment, as illustrated, the adjustable spine 1708 may include a crossbeam 1742 that attaches the first strip 1730 to the second strip 1732. In such an embodiment, at least a portion of the second strip 1732 may be attached to the fluid impermeable barrier 1702 such that the fluid impermeable barrier 1702 conforms to the shape of the second strip 1732. In an embodiment, the crossbeam 1742 may be omitted from the adjustable spine 1708. In such an embodiment, the first and second strips 1730, 1732 may be fixedly attached to one or more portions of the fluid impermeable barrier 1702 and the cap 1792. When at least one of the first or second strip 1730, 1732 is fixedly attached to the cap 1792, the cap 1792 is permanently attached to at least a portion of the adjustable spine 1708.

Figure 18:
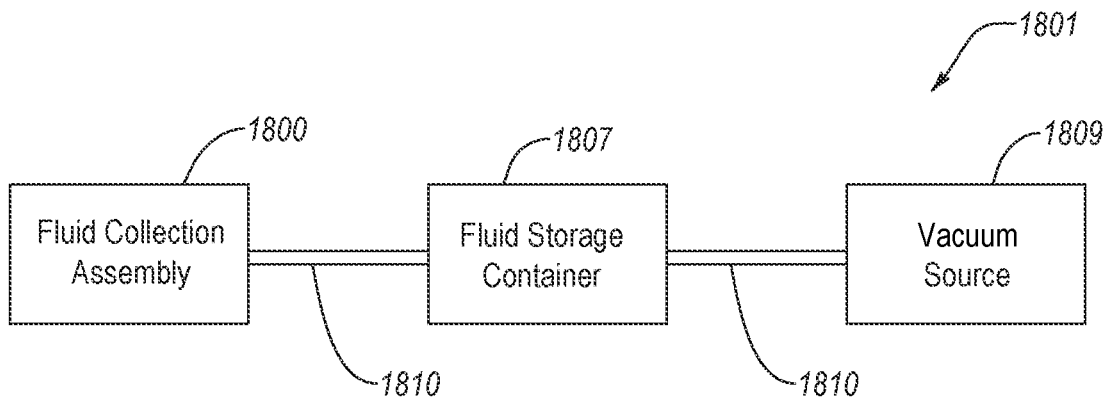
FIG. 18 is a block diagram of a fluid collection system for collecting one or more bodily fluids from a patient, according to an embodiment.

FIG. 18 is a block diagram of a fluid collection system 1801 for collecting one or more bodily fluids from a patient, according to an embodiment. The system 1801 includes a fluid collection assembly 1800, a fluid storage container 1807, and a vacuum source 1809. The fluid collection assembly 1800, the fluid storage container 1807, and the vacuum source 1809 may be fluidly coupled to each other via one or more conduits 1810. For example, fluid collection assembly 1800 may be operably coupled to one or more of the fluid storage container 1807 or the vacuum source 1809 via the conduit 1810. Bodily fluids (e.g., urine or other bodily fluids) collected in the fluid collection assembly 1800 may be removed from the fluid collection assembly 1800 via the conduit 1810 which protrudes into the fluid collection assembly 1800. For example, an inlet of the conduit 1810 may extend into the fluid collection assembly 1800, such as to a reservoir therein. The outlet of the conduit 1810 may extend into the fluid storage container 1807 or the vacuum source 1809. Suction force may be introduced into the chamber of the fluid collection assembly 1800 via the inlet of the conduit 1810 responsive to suction (e.g., vacuum) force applied at the outlet of the conduit 1810.

The suction force may be applied to the outlet of the conduit 1810 by the vacuum source 1809 either directly or indirectly. The suction force may be applied indirectly via the fluid storage container 1807. For example, the outlet of the conduit 1810 may be disposed within the fluid storage container 1807 and an additional conduit 1810 may extend from the fluid storage container 1807 to the vacuum source 1809. Accordingly, the vacuum source 1809 may apply suction to the fluid collection assembly 1800 via the fluid storage container 1807. The suction force may be applied directly via the vacuum source 1809. For example, the outlet of the conduit 1810 may be disposed within the vacuum source 1809. An additional conduit 1810 may extend from the vacuum source 1809 to a point outside of the fluid collection assembly 1800, such as to the fluid storage container 1807. In such examples, the vacuum source 1809 may be disposed between the fluid collection assembly 1800 and the fluid storage container 1807.

The fluid collection assembly 1800 may be similar or identical to any of the fluid collection assemblies disclosed herein in one or more aspects. The fluid collection assembly 1800 may be shaped and sized to be positioned adjacent to a female urethral opening. For example, the fluid collection assembly 1800 may include a fluid impermeable barrier at least partially defining a chamber (e.g., interior region) of the fluid collection assembly 1800. The fluid impermeable barrier also defines an opening extending therethrough from the external environment. The opening may be positioned adjacent to a female urethral opening. The fluid collection assembly 1800 may include at least one porous material disposed within the fluid impermeable barrier. The fluid collection assembly 1800 includes the adjustable spine disposed in the chamber or on the fluid impermeable barrier. The adjustable spine is sized, shaped, and positioned to retain a selected geometric configuration as disclosed herein. The conduit 1810 may extend into the fluid collection assembly 1800 at a first end (e.g., proximal) region, through one or more of the fluid impermeable barrier, fluid permeable membrane, or the fluid permeable support to a distal end (e.g., distal) region of the fluid collection assembly 1800. The conduit 1810 includes an inlet and an outlet, the outlet being fluidly coupled to the fluid storage container and the inlet being positioned in a portion of the chamber selected to be at a gravimetrically low point of the fluid collection assembly when worn.

The fluid storage container 1807 is sized and shaped to retain the bodily fluids therein. The fluid storage container 1807 may include a bag (e.g., drainage bag), a bottle or cup (e.g., collection jar), or any other enclosed container for storing bodily fluids such as urine. In some examples, the conduit 1810 may extend from the fluid collection assembly 1800 and attach to the fluid storage container 1807 at a first point therein. An additional conduit 1810 may attach to the fluid storage container 1807 at a second point thereon and may extend and attach to the vacuum source 1809. Accordingly, a vacuum (e.g., suction) may be drawn through fluid collection assembly 1800 via the fluid storage container 1807. Fluid, such as urine, may be drained from the fluid collection assembly 1800 using the vacuum source 1809.

The vacuum source 1809 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 1809 may provide a vacuum or suction to remove fluid from the fluid collection assembly 1800. In some examples, the vacuum source 1809 may be powered by one or more of a power cord (e.g., connected to a power socket), one or more batteries, or even manual power (e.g., a hand operated vacuum pump). In some examples, the vacuum source 1809 may be sized and shaped to fit outside of, on, or within the fluid collection assembly 1800. For example, the vacuum source 1809 may include one or more miniaturized pumps or one or more micro pumps. The vacuum sources 1809 disclosed herein may include one or more of a switch, a button, a plug, a remote, or any other device suitable to activate the vacuum source 1809.

Figure 19:
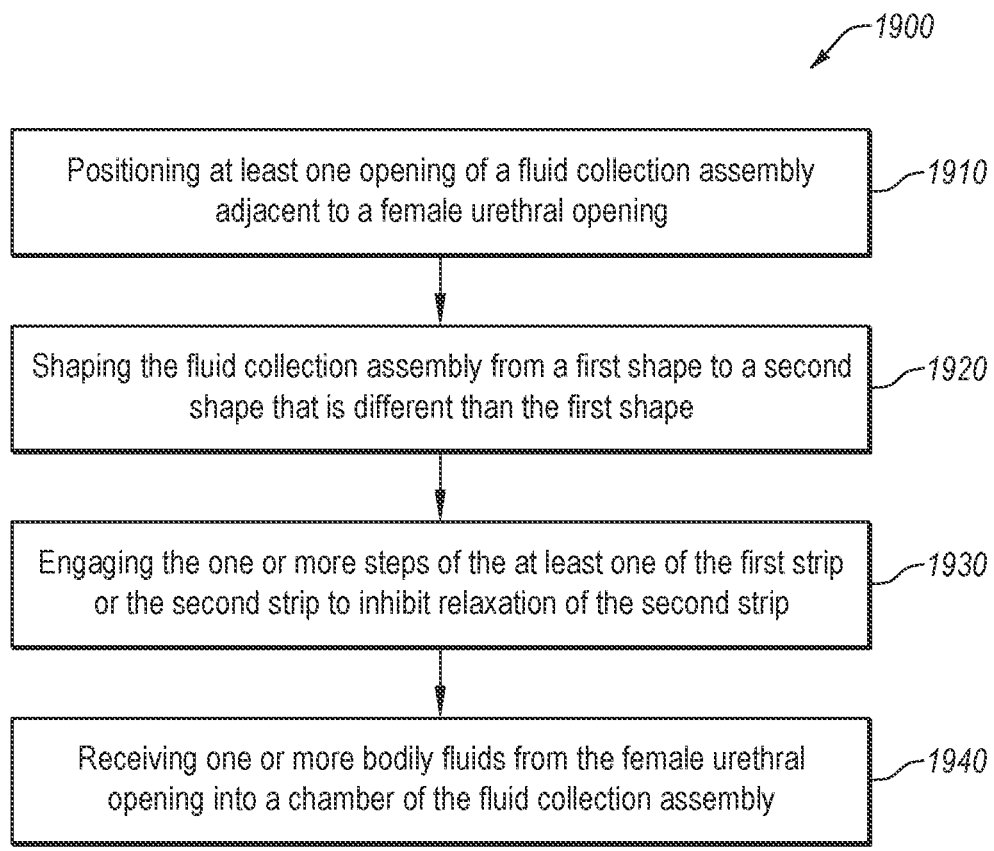
FIG. 19 is a flow diagram of a method to collect fluid, according to an embodiment.

FIG. 19 is a flow diagram of a method 1900 to collect fluid, according to an embodiment. The method 1900 of collecting fluid may utilize use any of the fluid collection assemblies and/or fluid collection systems disclosed herein. The method 1900 may include act 1910, which recites "positioning at least one opening of a fluid collection assembly adjacent to a female urethral opening." Act 1910 may be followed by act 1920, which recites "shaping the fluid collection assembly from a first shape to a second shape that is different than the first shape." Act 1920 may be followed by act 1930, which recites "engaging the one or more steps of the at least one of the first strip or the second strip to inhibit relaxation of the second strip." Act 1930 may be followed by act 1940, which recites "receiving one or more bodily fluids from the female urethral opening into a chamber of the fluid collection assembly."

Acts 1910, 1920, 1930, 1940 of the method 1900 are for illustrative purposes. For example, the acts 1910, 1920, 1930, 1940 of the method 1900 may be performed in different orders, split into multiple acts, modified, supplemented, or combined. In an example, one or more of the acts 1910, 1920, 1930, 1940 of the method 1900 may be omitted from the method 1900. Any of the acts 1910, 1920, 1930, 1940 may include using any of the fluid collection assemblies or systems disclosed herein.

Act 1910 recites "positioning at least one opening of a fluid collection assembly adjacent to a female urethral opening." The act 1910 may include utilizing any of the fluid collection assemblies or systems disclosed herein. In some examples, act 1910 may include positioning the opening of a fluid collection assembly such that the fluid permeable membrane of the female fluid collection assembly abuts or is positioned proximate to the female urethral opening. In some examples, act 1910 may include positioning the opening over the female urethral opening, such as positioning a longitudinally extending opening of the fluid collection assembly over the female urethra.

Act 1920 recites "shaping the fluid collection assembly from a first shape to a second shape that is different than the first shape." Shaping the fluid collection assembly into the selected geometric configuration may include shaping the fluid collection assembly to contour to the anatomy around the urethral opening of a female patient. In some embodiments, act 1920 includes forming the (e.g., a longitudinal shape of the) fluid collection assembly into an arcuate shape conforming to the perineal region of the patient, such as the vaginal and perineal region of a patient. In some embodiments, act 1920 includes flattening or rounding a lateral cross-section of the fluid collection assembly.

Act 1920 may include applying a force to the second strip of the adjustable spine. When the adjustable spine is positioned within the chamber, applying the force to the second strip may include bending the fluid collection assembly as a whole and/or pressing into the fluid collection assembly. For example, the force may be applied to the second strip by gripping the fluid collection assembly at or near the terminal ends thereof while one or more fingers press into a portion of the fluid collection assembly that is between the terminal ends of the fluid collection assembly. When the adjustable spine is positioned on an exterior of the fluid impermeable barrier, the force may be applied directly to the second strip. For example, when the fluid collection assembly includes a cap, the force may be applied to the second strip by removing the cap and applying the force, though it is noted that the may be applied to the second strip indirectly through the cap. The force may cause a portion of the second strip to move towards a portion of the first strip. Applying the force to the second strip may switch the second strip to the stressed configuration from a relaxed configuration.

Act 1930 recites, "engaging the one or more steps of the at least one of the first strip or the second strip to inhibit relaxation of the second strip." For example, as previously discussed, the force applied to the second strip may cause a portion of the second strip to move closer to the first strip. Such movements of the second strip may cause the steps of the shape memory material to become engaged. For example, when the first strip includes one or more steps, the one or more steps of the first strip may engage one or more steps of the second strip or the second strip itself. When the second strip includes the one or more steps, the one or more steps of the second strip may engage one or more steps of the first strip or the first strip itself.

Act 1940 recites, "receiving one or more bodily fluids from the female urethral opening into a chamber of the fluid collection assembly." In some examples, act 1940 includes receiving the bodily fluids through the opening of the fluid collection assembly. Act 1940 may include flowing the bodily fluids away from the opening using porous material, such as via a fluid permeable membrane and a fluid permeable support. Act 1940 may include flowing the bodily fluids towards a portion of the chamber that is fluidly coupled to an inlet of a conduit in fluid communication a vacuum source. For instance, act 1940 may include flowing the bodily fluids to a substantially unoccupied portion of the chamber (e.g., a reservoir), to a gravimetrically low point of the chamber, etc., such as via gravity, porous, or suction force. In some examples, porous the fluid into the chamber via the fluid permeable membrane and fluid permeable support may include porous urine into a reservoir in the fluid collection assembly.

The method 1900 may include applying suction with a vacuum source effective to suction the bodily fluids from the chamber via a conduit disposed therein and fluidly coupled to the vacuum source may include using any of the vacuum sources disclosed herein. Applying suction with a vacuum source may include activating the vacuum source (e.g., suction device) in fluid communication with the inlet of the conduit in the fluid collection assembly. In some examples, activating the vacuum source in fluid communication with the inlet of the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the bodily fluids from the chamber via the conduit disposed therein that is fluidly coupled to the vacuum source.

In some examples, applying suction with a vacuum source effective to suction the bodily fluids from the chamber via a conduit disposed therein and fluidly coupled to the vacuum source may be effective to remove at least some bodily fluids (e.g., urine) from the chamber (e.g., interior region) of the fluid collection assembly. In some examples, applying suction with a vacuum source effective to suction the bodily fluids from the chamber via a conduit disposed therein and fluidly coupled to the vacuum source may be effective to transfer at least some of the fluid from the chamber to a fluid storage container (e.g., a bottle or bag), such as from one or more of a reservoir, fluid permeable support, or fluid permeable membrane.

In some examples, the vacuum source (e.g., suction device) may be disposed on or within the fluid collection assembly and applying suction with the vacuum source may include activating the vacuum source. In some examples, the vacuum source may be spaced from the fluid collection assembly and applying suction with the vacuum source may include activating the vacuum source.

In some examples, applying suction with a vacuum source effective to suction the bodily fluids from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of fluid from the chamber of the fluid collection assembly. In the latter case, a user may receive the indication (e.g., from the controller) and activate the vacuum pump manually.

In an example, the method 1900 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

The fluid collection assemblies disclosed herein are configured to collect one or more bodily fluids from a female urethral opening. However, it is noted that any of the concepts disclosed herein may be used in fluid collection assemblies configured to collect bodily fluids from a male urethral opening (e.g., penis). For example, the adjustable spines disclosed herein may be used in fluid collection assemblies configured to collect bodily fluids from a male urethral opening. Examples of fluid collection assemblies that are configured to collected bodily fluids from a male urethral opening and methods of using such fluid collection assemblies are disclosed in International Application No. PCT/US2020/042262 filed on Jul. 14, 2020, U.S. patent application Ser. No. 16/433,773 filed on Apr. 3, 2020, U.S. Provisional Patent Application No. 63/047,374 filed on Jul. 2, 2020, and U.S. Provisional Patent Application No. 63/067,542 filed on Aug. 19, 2020, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A fluid collection assembly, comprising:
   a fluid impermeable barrier including at least one outer surface and at least one inner surface opposite the at least one outer surface, the fluid impermeable barrier defining at least a chamber, at least one opening, and a fluid outlet;
   at least one porous material disposed in the chamber; and
   an adjustable spine disposed in the chamber or attached to the at least one outer surface of the fluid impermeable barrier, the adjustable spine including:
      a first strip; and
      a second strip configured to switch at least from a relaxed configuration to a stressed configuration;
      wherein at least one of the first strip or the second strip includes one or more steps, the one or more steps configured to inhibit relaxation of the second strip when the second strip is in the stressed configuration;
   wherein at least a portion of the fluid collection assembly exhibits a first shape when the second strip exhibits the relaxed configuration and a second shape when the second strip exhibits the stressed configuration, wherein the first shape is different than the second shape.

2. The fluid collection assembly of claim 1, wherein the at least one porous material defines a gap that is substantially unoccupied between the first strip and the second strip.

3. The fluid collection assembly of claim 1, wherein the fluid impermeable barrier includes a front side that defines the at least one opening and a back side that is opposite the front side, at least a portion of the front side exhibits a concave curve and at least a portion of the back side exhibits a convex curve relative to a point above the at least one opening when the at least a portion of the fluid collection assembly exhibits the second shape.

4. The fluid collection assembly of claim 3, wherein:
   the second strip is concavely curved when the second strip is in the stressed configuration; and
   the second strip is attached to the at least one outer surface of the back side.

5. The fluid collection assembly of claim 4, further comprising a cap that at least partially encloses the adjustable spine.

6. The fluid collection assembly of claim 3, further comprising a conduit disposed in the chamber, the conduit including a front conduit side and a back conduit side, the front conduit side closer to the front side of the fluid impermeable barrier than the back conduit side, the back conduit side closer to the back side of the fluid impermeable barrier than the front conduit region;
   the second strip attached to the back conduit side.

7. The fluid collection assembly of claim 3, further comprising a conduit disposed in the chamber, the conduit including a front conduit side and a back conduit side, the front conduit side closer to the front side of the fluid impermeable barrier than the back conduit side, the back conduit side closer to the back side of the fluid impermeable barrier than the front conduit side;
   the second strip attached to the front conduit side.

8. The fluid collection assembly of claim 1, wherein the one or more steps defines one or more recesses therebetween.

9. The fluid collection assembly of claim 1, wherein the one or more steps include one or more protrusions.

10. The fluid collection assembly of claim 9, wherein:
    the one or more protrusions includes a plurality of protrusions, the plurality of protrusions arranged in one or more rows, wherein each of the one or more rows includes two protrusions separated by a recess; and
    at least a portion of the first strip or the second strip that does not include the one or more steps configured to fit within the recess.

11. The fluid collection assembly of claim 1, wherein the one or more protrusions includes a plurality of protrusions and a height that at least some of the plurality of protrusions decreases with distance from a terminal end of the first strip or the second strip that includes the plurality of protrusions.

12. The fluid collection assembly of claim 1, wherein the first strip includes the one or more steps.

13. The fluid collection assembly of claim 1, wherein the one or more steps include one or more first steps and one or more second steps, the first strip includes the one or more first steps and the second strip includes the one or more second steps.

14. The fluid collection assembly of claim 13, wherein one of the one or more first steps or the one or more second steps includes one or more protrusions and the other of the one or more first steps or the one or more second steps defines one or more recesses therebetween configured to receive at least a portion of the one or more protrusions.

15. The fluid collection assembly of claim 13, each of the one or more first steps and the one or more second steps includes one or more protrusions.

16. The fluid collection assembly of claim 1, wherein the one or more steps includes one or more protrusions, and wherein:
    when the first strip includes the one or more protrusions, the one or more protrusions are angled away from a terminal end of the first strip that is closest to the one or more protrusions; and
    when the second strips includes the one or more protrusions, the one or more protrusions are angled towards a terminal and of the second strip that is closest to the one or more protrusions.

17. The fluid collection assembly of claim 1, wherein one of the first strip or the second strip includes the one or more steps and the other of the first strip or the second strip does not include the one or more steps.

18. The fluid collection assembly of claim 1, wherein one of the first strip or the second strip includes a base and at least one sidewall extending from the base.

19. The fluid collection assembly of claim 1, wherein the second strip is:
substantially straight when the second strip is in the relaxed configuration; and
concavely curved when the second strip is in the stressed configuration.

20. The fluid collection assembly of claim 1, wherein:
the first strip includes a first terminal end and a second terminal end spaced from the first terminal end; and
the second strip includes a third terminal end and a fourth terminal end spaced from the third terminal end;
wherein the first terminal end and the fourth terminal end are fixedly attached to one or more other components of the fluid collection assembly.

21. The fluid collection assembly of claim 1, wherein the first strip is more rigid than the second strip.

22. The fluid collection assembly of claim 1, wherein:
the first strip includes the one or more steps;
the adjustable spine further includes a third strip configured to switch at least from a relaxed configuration to a stressed configuration that is different than the relaxed configuration; and
the one or more steps are configured to engage the third strip.

23. The fluid collection assembly of claim 1, wherein the adjustable spine further includes a crossbeam attached to and extending between the first strip and the second strip.

24. The fluid collection assembly of claim 1, wherein the adjustable spine include a space extending between the first strip and the second strip.

25. The fluid collection assembly of claim 1, wherein the adjustable spine further includes:
a third strip; and
a fourth strip configured to switch at least from a relaxed configuration to a stressed configuration;
wherein at least one of the third strip or the fourth strip includes one or more additional steps, the one or more additional steps configured to inhibit relaxation of the fourth strip when the fourth strip exhibits the relaxed configuration thereof.

26. A fluid collection system, comprising:
a fluid storage container configured to hold one or more bodily fluids therein;
a fluid collection assembly including:
a fluid impermeable barrier including at least one outer surface and at least one inner surface opposite the at least one outer surface, the fluid impermeable barrier defining at least a chamber, at least one opening, and a fluid outlet;
at least one porous material disposed in the chamber; and
an adjustable spine disposed in the chamber or attached to the at least one outer surface of the fluid impermeable barrier, the adjustable spine including:
a first strip; and
a second strip configured to switch at least from a relaxed configuration to a stressed configuration;
wherein at least one of the first strip or the second strip includes one or more steps, the one or more steps configured to inhibit relaxation of the second strip when the second strip is in the stressed configuration;
wherein at least a portion of the fluid collection assembly exhibits a first shape when the second strip exhibits the relaxed configuration and a second shape when the second strip exhibits the stressed configuration, wherein the first shape is different than the second shape; and
a vacuum source in fluid communication with the fluid storage container and the fluid collection assembly, the vacuum source configured to draw the one or more bodily fluids from the fluid collection assembly and deposit the one or more bodily fluids in the fluid storage container via one or more conduits.

* * * * *